(12) United States Patent
Martin et al.

(10) Patent No.: US 10,745,395 B2
(45) Date of Patent: Aug. 18, 2020

(54) COMPOUNDS FOR THEIR USE AS DRUGS FOR THE TREATMENT AND/OR THE PREVENTION OF INFECTION(S) CAUSED BY BIOFILM-FORMING BACTERIA

(71) Applicants: CENTRE NATIONAL DE LA RECHERCHE SCIENTIFIQUE, Paris (FR); UNIVERSITE D'ORLEANS, Orleans Cede (FR); JAGIELLONIAN UNIVERSITY, Cracow (PL)

(72) Inventors: Olivier Martin, Saint-Hilaire-Saint-Mesmin (FR); Estelle Gallienne-Boivineau, Lingny le Ribault (FR); Cyril Nicolas, Nouan-le-fuzlier (FR); Piotr B. Heczko, Cracow (PL); Grazyna Stochel, Cracow (PL); Magdalena Strus, Cracow (PL); Agnieszka Kyziol, Cracow (PL); Diana Mikolajczyk, Cracow (PL); Agnieszka Machul, Cracow (PL)

(73) Assignees: CENTRE NATIONAL DE LA RECHERCHE SCIENTIFIQUE, Paris (FR); UNIVERSITE D'ORLEANS, Orleans (FR); JAGIELLONIAN UNIVERSITY, Cracow (PL)

( * ) Notice: Subject to any disclaimer, the term of this patent is extended or adjusted under 35 U.S.C. 154(b) by 87 days.

(21) Appl. No.: 15/507,028

(22) PCT Filed: Aug. 26, 2015

(86) PCT No.: PCT/EP2015/069571
§ 371 (c)(1),
(2) Date: Feb. 27, 2017

(87) PCT Pub. No.: WO2016/030434
PCT Pub. Date: Mar. 3, 2016

(65) Prior Publication Data
US 2018/0030047 A1 Feb. 1, 2018

(30) Foreign Application Priority Data
Aug. 26, 2014 (EP) .................................... 14306315

(51) Int. Cl.
| C07D 207/12 | (2006.01) |
| C07D 471/04 | (2006.01) |
| C07D 211/46 | (2006.01) |
| A01N 43/36 | (2006.01) |
| A01N 43/40 | (2006.01) |
| A01N 43/90 | (2006.01) |
| A61K 31/40 | (2006.01) |
| A61K 31/437 | (2006.01) |
| A61K 31/445 | (2006.01) |
| A61K 31/551 | (2006.01) |
| C07D 211/40 | (2006.01) |
| C07D 487/04 | (2006.01) |

(52) U.S. Cl.
CPC .......... *C07D 471/04* (2013.01); *A01N 43/36* (2013.01); *A01N 43/40* (2013.01); *A01N 43/90* (2013.01); *A61K 31/40* (2013.01); *A61K 31/437* (2013.01); *A61K 31/445* (2013.01); *A61K 31/551* (2013.01); *C07D 207/12* (2013.01); *C07D 211/40* (2013.01); *C07D 211/46* (2013.01); *C07D 487/04* (2013.01)

(58) Field of Classification Search
CPC ................................................. C07D 47/104
See application file for complete search history.

(56) References Cited

FOREIGN PATENT DOCUMENTS

WO 2012-112061 A1 8/2012

OTHER PUBLICATIONS

Malladi et al., Bio.Org. & Med. Chem., vol. 19,(18), 5500-5510, (2011).*
Maladi et al. Bioorganic & Med. Chem. 19(18)2001pp. 5500-5506 (2011).*
Bosco et al. Tetrahendron Letters, Pergamon, 48(1)(2006) pp. 153-157.*
Maddry et all, Bioorganic & Med. Chem. Letters, Pergamon 8(3) (1998) pp. 237-242.*
Venkata L.A. Malladi, et al., "Substituted lactam and cyclic azahemiacetals modulate Pseudomonas aeruginosa quorum sensing", Bioorganic & Medicinal Chemistry, 2011, pp. 5500-5506, vol. 19, No. 18 (2011), Elsevier Ltd.

(Continued)

*Primary Examiner* — Paul V Ward
(74) *Attorney, Agent, or Firm* — Young & Thompson

(57) ABSTRACT

The present invention relates to compounds of the following formula (I), wherein: m represents an integer being equal to 0, 1, 2, 3, 4, 5 or 6, X represents a simple bond or a radical —CHR$_1$ wherein R$_1$ represents:—a hydrogen atom, or—a linear or branched, possibly interrupted by up to 3 heteroatoms selected from O, S or N and/or possibly substituted, (C$_1$-C$_{12}$)-alkyl, R$_2$, R$_3$ and R$_4$ represent independently from each other:—a hydrogen atom, or—a linear or branched (C$_1$-C$_{12}$)-alkyl or (C$_1$-C$_{12}$)-acyl R5 represents:—a hydrogen atom, or—a linear or branched, possibly substituted, (C$_1$-C$_{13}$)-alkyi possibly substituted and possibly interrupted by up to 3 heteroatoms selected from O, S or N, R$_6$ represents:—a hydrogen atom, or—a linear or branched possibly substituted (C$_1$-C$_{12}$)-alkyl, possibly substituted and possibly interrupted by up to 3 heteroatoms selected from O, S or N, for their use as antibacterial drugs for the treatment and/or the prevention of infection(s) caused by biofilm-forming bacteria.

18 Claims, 4 Drawing Sheets

(56) References Cited

OTHER PUBLICATIONS

Venkata L.A. Malladi, et al. "Inhibition of LuxS by S-Ribosylhomocysteine Analogues Containing a [4-Aza]Ribose Ring", Bioorganic & Medicinal Chemistry, Sep. 15, 2011, pp. 5507-5519, vol. 19, No. 18 (2011), Elsevier Ltd.

Robert C. Reynolds, et al., "Ethambutol-sugar hybrids as potential inhibitors of mycobacterial cell-wall biosynthesis", Carbohydrate Research, Apr. 30, 1999, pp. 164-179, vol. 317, Issues 1-4, Elsevier Science Ltd., Great Britain.

Michaël Bosco, et al., "Synthesis of 2',3'-dihydrosolanesyl analogues of β-d-arabinofuranosyl-1-monophosphoryldecaprenol with promising antimycobacterial activity", Tetrahedron Letters, Nov. 30, 2006, pp. 153-157, vol. 48, No. 1, Elsevier Ltd., Great Britain.

Livia Gomez, et al., "Chemoenzymatic synthesis, structural study and biological activity of novel indolizidine and quinolizidine iminocyclitols", Organic & Biomolecular Chemistry, Oct. 31, 2012, pp. 6309-6321, Issue 31.

Joseph A. Maddry, et al., "Homologated aza analogs of arabinose as antimycobacterial agents", Bioorganic & Medicinal Chemistry Letters, Feb. 3, 1998, pp. 237-242, vol. 8, No. 3, Pergamon, Amsterdam, Netherlands.

Hao-Wei Shih, et al., "Combinatorial approach toward synthesis of small molecule libraries as bacterial transglycosylase inhibitors", Organic & Biomolecular Chemistry, Jun. 7, 2010, pp. 2586-2593, vol. 8, Issue 11.

Atsushi Kato, et al., "Isolation of Glycosidase-Inhibiting Hyacinthacines and Related Alkaloids from Scilla socialis", Journal of Natural Products, May 31, 2007, pp. 993-997, vol. 70, Issue 6.

Naoki Asano, et al., "Glycosidase-inhibiting pyrrolidines and pyrrolizidines with a long side chain in Scilla peruviana", Journal of Natural Products, Apr. 29, 2004, pp. 846-850, vol. 67, Issue 5.

Naoki Asano, et al. "Nitrogen-containing furanose and pyranose analogues from Hyacinthus orientalis", Journal of Natural Products, Apr. 24, 1998, pp. 625-628, vol. 61, Issue 5.

Jordi Calveras, et al., "Dihydroxyacetone Phosphate Aldolase Catalyzed Synthesis of Structurally Diverse Polyhydroxylated Pyrrolidine Derivatives and Evaluation of their Glycosidase Inhibitory Properties", Chemistry—A European Journal, Jul. 27, 2009, pp. 7310-7328, vol. 15, Issue 30.

Hera Vlamakis, et al., "Sticking together: building a biolfilm the Bacillus subtilis way", Nature Reviews Microbiology, Mar. 1, 2013, pp. 157-168, vol. 11, No. 3, Macmillan Publishers Limited.

Kathleen Kulka, et al., "Growth of *Mycobacterium tuberculosis* Biofilms", Journal of Visualized Experiments, Feb. 15, 2012, pp. 1-6, Issue 60.

International Search Report issued for related International Application No. PCT/EP2015/069571 dated Feb. 1, 2016.

\* cited by examiner

COMPOUNDS FOR THEIR USE AS DRUGS FOR THE TREATMENT AND/OR THE PREVENTION OF INFECTION(S) CAUSED BY BIOFILM-FORMING BACTERIA

The present invention relates to compounds for their use as antibacterial drugs for the treatment and/or the prevention of infection(s) caused by biofilm-forming bacteria.

Biofilm is a group of microorganisms in which cells stick to each other on a surface. These adherent cells are frequently embedded within a self-produced matrix of extracellular polymeric substance (EPS). That is why a biofilm is also usually defined as surface-associated microbial communities, surrounded by an extracellular polymeric substance (EPS)-matrix. A biofilm comprises mainly polysaccharides, proteins, nucleic acids, and metabolites produced by microorganisms which compose the said biofilm.

Biofilm is produced by microorganisms, notably by bacteria, in response to reduction of nutrients, increased levels of reactive oxygen species, change in pH, or under the influence of immune cells or the influence of antibiotics. For example, biofilm can be produced by Pseudomonas aeruginosa. Pseudomonas aeruginosa is a well-recognized opportunistic pathogen responsible for various infections, from acute, life-threatening ventilator-related pneumonias in intubated patients and cystic fibrosis patients to chronic wound infections in diabetic patients.

Biofilm cells show much greater resistance to environmental challenges including antimicrobial agents than their free-living counterparts (planktonic cells). Thus, the biofilm mode of life is believed to significantly contribute to successful microbial survival in hostile environment. Indeed, the biofilm produced by microorganisms enables acquisition of new ecological niches and can survive in harsh environments.

Biofilm can grow on any type of natural or artificial surface, whether mineral (rock, air-liquid interfaces . . . ) or organic (skin, digestive tract of animals, roots and leaves of plants), industrial (pipes, ship hulls) or medical (protheses, catheters).

Biofilm is considered as one of the most important and difficult to cure form of microbial pathogenicity. Indeed, conventional methods that would otherwise lead to eradication of planktonic microbes (microbes which do not form a biofilm) are often ineffective to the microbial populations inside the biofilms due to their particular physiology and physical matrix barrier. Notably, since P. aeruginosa embedded in biofilm matrix are much more resistant to antibiotics, disinfectants and surfactants, treatment of P. aeruginosa infections is extremely difficult and often unsuccessful (see Bose S, Ghosh A K. Biofilms: a challenge to medical science. *J Clin Diagn Res* 5(1), 127-130 (2011) and Costerton J W, Stewart P S, Greenberg E P. Bacterial biofilms: a common cause of persistent infections. *Science* 284, 1318-1322 (1999)). Therefore, many efforts have been made to prevent P. aeruginosa biofilm formation in vitro and in vivo.

That is why the biofilms are considered since a long time as an important public health problem. Consequently they have been the subject of several studies in order to determine how to combat them.

Thus, some strategies to treat or prevent the biofilm formation are already known.

For example, some strategies have tried to inhibit the microbial attachment because microbial attachment is essential for biofilm formation. With these approaches, antimicrobial agents such as antimicrobial peptides are immobilized on surfaces in order to inhibit the development of biofilms. However, surfaces coated with such antimicrobials are considered short term protection.

Some other strategies have tried to kill biofilms cells, for example with antimicrobial peptides. However, the antimicrobial peptides have undesirable properties such as non-specific toxicity and low stability, which limit their application.

The most important strategies already known are detailed in the minireview "Strategies to control biofilms", *FEMS Immunol Med Microbiol* 65 (2012) 146-157.

The international application WO 2008/142094 describes also triazole compounds for treating biofilm formation.

Moreover, most of the studies on inhibition of biofilm formation by P. aeruginosa focused on substances which may interact with cell-to-cell signaling (quorum-sensing) or on gene regulation of biofilm synthesizing enzymes (see Vu B, Chen M, Crawford R J, Ivanova E P. Bacterial extracellular polysaccharides involved in biofilm formation. *Molecules* 14, 2535-2554 (2009)).

It has also been mentioned that 1-deoxynojirimycin (DNJ) has an inhibitory action on *Streptococcus mutans* biofilm formation (*J Antimicrob Chemother* 62, 751-757 (2008)). However, it is clear from NMR data that the purified and tested compound is not DNJ, despite what it is stated in the article. According to this article, the $^1$H-NMR spectrum of purified compound showed peaks at $\delta=5.4$ (dd, NH), 5.1 (broad singlet), 4.7 (dd), 4.4 (m), 4.2 (dd), 4.0 (dd), 3.6 (dd) and 3.4 (dd). However, the $^1$H-NMR spectrum of DNJ in $D_2O$ (400 MHz) shows peak at $\delta=3.83$ (dd, H6b), 3.63 (dd, H6a), 3.52 (dt, H2), 3.34 (t, H3), 3.26 (t, H4), 3.15 (dd, H1b), 2.59 (ddd, H5), and 2.49 (t, H1a) and the $^{13}$C-NMR spectrum in $D_2O$ (400 MHz) shows peaks at d=78.69 (C3), 71.73 (C4), 71.09 (C2), 61.70 (C6), 60.08 (C5) and 49.02 (C1). These data unambiguously establish that the reported compound in the aforementionned article is not DNJ.

Thus, until now, no method has been proved to be efficient to treat and/or prevent the infections caused by biofilm-forming bacteria.

Besides, until now, no method has been proved to be efficient to treat and/or prevent the biofilm formation of bacteria.

A lack of an effective method to treat and/or prevent the infections caused by such biofilm-forming bacteria and/or a lack of an effective method to treat and/or prevent the biofilm formation by such bacteria is a major problem, both in medical and economical terms.

Indeed, the absence of an effective way to treat and/or prevent the infections caused by such biofilm-forming bacteria and/or the absence of an effective way to treat and/or prevent the biofilm formation by such bacteria lead for example to a significant prolongation of the treatment time. Literature data indicate that the killing dose for any given antibiotic is more than 1000 times higher for biofilm bacteria than for planktonic bacteria of the same strain. The poor efficacy of antibiotics against bacteria contained in the biofilm is associated with inefficient penetration of the antibiotic through the biofilm matrix either due to specific adsorption by matrix or to physical barriers (see for example *Appl. Environ. Microbiol.* 60, 4339-4344 (1994), and *Antimicrob. Agents Chemother.* 38, 2125-2133 (1994)).

Thus, there is an urgent need to develop novel strategies to treat and/or prevent the infections caused by biofilm-forming bacteria.

There is also an urgent need to develop novel strategies to treat and/or prevent the biofilm formation by bacteria.

That is why, one of the aims of the present invention is to provide iminosugars for their use as antibacterial drugs for the treatment and/or the prevention of infection(s) caused by biofilm-forming bacteria.

Another aim of the present invention is also to provide iminosugars for their use for the treatment and/or the prevention of biofilm formation by bacteria.

The present invention also relies on the unexpected experimental results from the Inventors according to which iminosugars can be used as antibacterial drugs for the treatment and/or the prevention of infection(s) caused by biofilm-forming bacteria.

The present invention also relies on the unexpected experimental results from the Inventors according to which iminosugars can prevent and/or treat the formation of biofilm formation by bacteria. Thus, by lowering or suppressing the formation of biofilms, iminosugars can contribute to an increased sensitivity of the microorganism to antibiotics or disinfecting agents.

That is why the present invention concerns iminosugars for their use as antibacterial drugs for the treatment and/or the prevention of infection(s) caused by biofilm-forming bacteria.

The present invention also concerns iminosugars for their use for the treatment or the prevention of biofilm formation by bacteria.

The present invention also concerns novel iminosugars and novel pharmaceutical compositions.

The present invention also concerns novel compositions comprising at least one iminosugar, in combination with one or several antibiotics, and their use as antibacterial drugs for the treatment and/or the prevention of infection(s) caused by biofilm-forming bacteria, or their use for the treatment and/or the prevention of biofilm formation by bacteria.

The present invention also concerns novel compositions comprising at least one iminosugar, in combination with one or several disinfecting agent, and their use as antibacterial for the treatment and/or the prevention of infection(s) caused by biofilm-forming bacteria, or their use for the treatment and/or the prevention of biofilm formation by bacteria.

The present invention also concerns the use of iminosugars as disinfectants.

The present invention also concerns the use of iminosugars for the preparation of polymers, and polymers containing the said iminosugars.

Thus, the compounds of the invention can be used alone, because they have indirect antibacterial properties, or the compounds of the invention can be used in combination with antibiotics or disinfecting agents, because they can improve the effect of such antibiotics or disinfecting agents. Compounds of the present invention can provide a synergistic effect when used with antibiotics or disinfecting agents.

Thus, in a first embodiment the present invention relates to compounds of the following formula I:

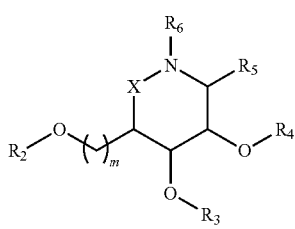

wherein:
m represents an integer being equal to 0, 1, 2, 3, 4, 5 or 6,
X represents a simple bond or a radical —$CHR_1$— wherein
$R_1$ represents:
  a hydrogen atom, or
  a linear or branched, possibly interrupted by up to 3 heteroatoms selected from O, S or N and/or possibly substituted, ($C_1$-$C_{12}$)-alkyl,
$R_2$, $R_3$ and $R_4$ represent independently from each other:
  a hydrogen atom, or
  a linear or branched ($C_1$-$C_{12}$)-alkyl, or
  a linear or branched ($C_1$-$C_{12}$)-acyl,
$R_5$ represents:
  a hydrogen atom, or
  a linear or branched, possibly substituted, ($C_1$-$C_{13}$)-alkyl, or
  a linear or branched, possibly substituted ($C_1$-$C_{13}$)-alkyl interrupted by up to 3 heteroatoms selected from O, S or N,
$R_6$ represents:
  a hydrogen atom, or
  a linear or branched possibly substituted ($C_1$-$C_{12}$)-alkyl, or
  a linear or branched possibly substituted ($C_1$-$C_{12}$)-acyl, or
  a linear or branched, possibly substituted ($C_1$-$C_{12}$)-alkyl interrupted by up to 3 heteroatoms selected from O, S or N, or
  a linear or branched, possibly substituted ($C_1$-$C_{12}$)-acyl interrupted by up to 3 heteroatoms selected from O, S or N,
or $R_5$ and $R_6$ represent together with the N atom to which $R_6$ is bound and the carbon atom to which $R_5$ is bound an alkylene radical Z having 2 to 5 carbon atoms which is possibly substituted and/or possibly interrupted by up to 3 heteroatoms selected from O, S, N and/or terminated by an heteroatom selected from O, S, N,
and the pharmaceutically acceptable salts, enantiomers, diastereoisomers of same, as well as mixture of same, for their use as antibacterial drugs for the treatment and/or the prevention of infection(s) caused by biofilm-forming bacteria.

The expression "X represents a simple bond" means that X does not represent an atom. Thus, in this case, the heterocyclic ring is a 5 heterocyclic ring.

The expression "possibly interrupted by up to 3 heteroatoms" means that the alkyl group and/or the acyl group can have supplementary heteroatoms selected from O, S, N. It means also that if the alkyl group and/or the acyl group is/are interrupted by up to 3 heteroatoms, these heteroatoms are necessarily selected from O, S, N. Consequently, the alkyl group and/or the acyl group according to the present invention cannot be interrupted by an heteroatom P. O and N are the preferred heteroatoms which interrupted the alkyl group and/or the acyl group. In a preferred embodiment, O, S, N have to be understood as the heteroatom per se, and do not embrace bonds, for example NH.

The expression "interrupted by up to 3 heteroatoms" means interrupted by one, two or three heteroatoms. For example the alkyl group or the acyl group can contain one, two or three heteroatoms, which are one heteroatom O, two heteroatoms O, three heteroatoms O, one heteroatom O and one heteroatom S, one heteroatom O and two heteroatoms S, but also one heteroatom O and one heteroatom S and one heteroatom N or one heteroatom S and one heteroatom N . . . . . This list is not exhaustive.

An acyl group contains always one heteroatom O, however this heteroatom O is not considered as a supplementary heteroatom according to the present invention. Thus, if the acyl group is interrupted by three heteroatoms O, four heteroatoms O will be present in the group considered in its entirety.

The term "alkyl" refers to a linear or branched chain, saturated hydrocarbon having the indicated number of carbon atoms. Thus a $(C_1-C_{12})$-alkyl or a $(C_1-C_{13})$-alkyl means an alkyl with 1, 2, 3, 4, 5, 6, 7, 8, 9, 10, 11, 12 or 13 carbon atoms. A $(C_1-C_{12})$ alkyl or a $(C_1-C_{13})$ alkyl is meant to include but is not limited to methyl, ethyl, propyl, isopropyl, butyl, sec-butyl, tert-butyl, pentyl, hexyl, octyle, nonyle, decyle, undecyle, dodecyl. An alkyl group can be unsubstituted or optionally substituted with one or more substituents.

The term "acyl" refers to a carbonyl group attached to an alkyl or aryl group with the indicated number of carbon atoms. An acyl has the formula RCO, where R represents an alkyl group or an aryl group that is attached to the CO group with a single bond. Thus, a $(C_1-C_{12})$-acyl means an acyl with 1, 2, 3, 4, 5, 6, 7, 8, 9, 10, 11 or 12 carbon atoms. An acyl group can be unsubstituted or optionally substituted with one or more substituents.

The expression "$R_5$ and $R_6$ represent together with the N atom to which $R_6$ is bound and the carbon atom to which $R_5$ is bound an alkylene radical Z having 2 to 5 carbon atoms which is possibly substituted and/or possibly interrupted by up to 3 heteroatoms selected from O, S, N and/or terminated by an heteroatom selected from O, S, N" means also that $R_5$ and $R_6$ represent together with the N atom to which $R_6$ is bound and the carbon atom to which $R_5$ is bound a possibly substituted 5 to 7 membered heterocyclic ring having one N atom and possibly 1 or 2 other heteroatoms selected from O, S or N.

The term "alkylene radical" means a bivalent saturated aliphatic radical regarded as derived from an alkene by opening of the double bond or from an alkane by removal of two hydrogen atoms from different carbon atoms. An alkylene radical can also be defined as a $-(CH_2)x-$ group, x having a value of an integer 2, 3, 4, 5. Thus, an alkylene radical according to the present invention can be $-CH_2-CH_2-$ or $-CH_2-CH_2-CH_2-$ or $-CH_2-CH_2-CH_2-CH_2-$ or $-CH_2-CH_2-CH_2-CH_2-CH_2-$ ..... This list is not exhaustive. An alkylene radical can be unsubstituted or optionally substituted with one or more substituents.

The expression "an alkylene radical Z having 2 to 5 carbon atoms" means an alkylene radical having 2, 3, 4 or 5 carbon atoms.

According to the present invention, if the radical alkylene Z is not interrupted or terminated by 1, 2 or 3 heteroatoms selected from O, S, N, thus the alkylen radical Z contains always 3, 4 or 5 carbon atoms.

According to the present invention, if the radical alkylene Z is interrupted or terminated by 1 heteroatom selected from O, S, N, thus the alkylen radical Z contains always 2, 3 or 4 carbon atoms.

According to the present invention, if the radical alkylene Z is interrupted or terminated by 2 heteroatoms selected from O, S, N, thus the alkylen radical Z contains always 2 or 3 carbon atoms.

According to the present invention, if the radical alkylene Z is interrupted or terminated by 3 heteroatoms selected from O, S, N, thus the alkylen radical Z contains always 2 carbon atoms.

The expression "interrupted by up to 3 heteroatoms selected from O, S, N" means that the alkylene radical can be defined as a $-(CH_2)x$-heteroatom-$CH_2$ group, x having a value of an integer 1, 2, 3, for example a $-CH_2-O-CH_2-$ group, $-CH_2-S-CH_2-$ group, $-CH_2-N-CH_2-$ group, $-(CH_2)_2-O-CH_2-$ group, $-(CH_2)_3-O-CH_2-$ or a $-CH_2$-heteroatom-$CH_2$-heteroatom-$CH_2$ group, for example $-CH_2-N-CH_2-O-CH_2-$ group .... This list is not exhaustive.

The expression "terminated by an heteroatom selected from O, S, N" means that the alkylene radical can be defined as a $-(CH_2)x$-heteroatom group, x having a value of an integer 1, 2, 3, 4, for example $-(CH_2)x-O-$ group; $-(CH_2)x-S-$group; $-(CH_2)x-N$ group .... This list is not exhaustive.

The expression "a pharmaceutically acceptable salt" is a pharmaceutically acceptable, organic or inorganic acid or base salt of a compound of the invention.

The term "enantiomer" means one of a pair of molecular entities which are mirror images of each other and non-superposable.

The term "diastereoisomer" means stereoisomers which are not related as mirror images. The term "stereoisomers" means isomeric molecules that have the same molecular formula and sequence of bonded atoms (constitution), but that differ only in the three-dimensional orientations of their atoms in space (configuration).

The expression "the treatment and/or the prevention of infection(s) caused by biofilm-forming bacteria" means also "the treatment and/or the prevention of infection(s) involving the formation of biofilm by bacteria".

The expressions "infection(s) caused by biofilm-forming bacteria" and "the treatment and/or the prevention of infection(s) involving the formation of biofilm by bacteria" are for example dental caries, gingivitis, pneumonia complicating, cystic fibrosis, otitis media (especially in children), osteomyelitis, prostatitis, pneumonia, chronic skin wounds, infections related to transplantation, implantation of medical devices and long-dwelling catheterization. All these infections are related to the formation of biofilm by the pathogens, notably by biofilm-forming bacteria.

As previously explained, the term <<biofilm>> means a matrix which contains mainly exopolysaccharides, proteins, nucleic acids and metabolites produced by bacteria. Exopolysaccharide chain determines the stability of the biofilm structure.

Literature shows that bacterial EPS (extracellular polymeric substance) are high molecular weight biopolymers composed of repeating units linked by carbohydrate α and β-glycosidic bonds. These biopolymers are associated with the surface of the bacterial cells creating capsular exopolysaccharide or are secreted outside the cell in the form of slime exopolysaccharide. Bacterial exopolysaccharides, owing to the composition of sugar, can be divided into two groups: homopolysaccharides (HoPS) and heteropolysaccharides (HePS). Homopolysaccharides are made of one type of monosaccharide, while heteropolysaccharides are composed of various monosaccharides. As an example of homopolysaccharides, dextrans are synthesized by extracellular glycansucrases belonging to the transferases. These enzymes catalyze the transfer of a glucosyl residue from sucrose and the addition of one of the resulting monosaccharide residues to the growing chain. The catalytic mechanism of the enzyme activity has been thoroughly investigated by Robyt et al. (see Dextransucrase and the mechanism for dextran biosynthesis. *Carbohydr Res* 343 (18), 3039-48 (2008)).

In the present invention, the term "bacteria" means all the bacteria, notably bacteria of the genus *Pseudomonas*, preferably *Pseudomonas aeruginosa*.

Such bacterias can be sensitive or resistant bacterias (notably against antibiotics or disinfecting agents).

In other embodiment, the present invention relates to compounds of the following formula I:

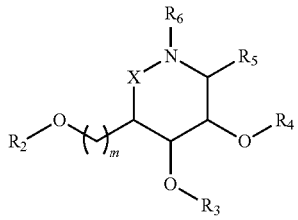

wherein:
m represents an integer being equal to 0, 1, 2, 3, 4, 5 or 6,
X represents a simple bond or a radical —CHR$_1$— wherein R$_1$ represents:
 a hydrogen atom, or
 a linear or branched (C$_1$-C$_{12}$)-alkyl, preferably a (C$_1$-C$_6$)-alkyl, possibly interrupted by up to 3 heteroatoms selected from O, S or N and/or possibly substituted by up to 3 radicals selected from:
  —OH,
  —O-linear (C$_1$-C$_{12}$)-alkyl, preferably a (C$_1$-C$_6$)-alkyl,
  —O-linear (C$_1$-C$_{12}$)-acyl, preferably a (C$_1$-C$_6$)-acyl,
  a halogen atom chosen among Br, Cl, I, F, preferably F,
  a possibly salified or esterified carboxy,
  an oxo group,
  an aromatic or heteroaromatic aryl possibly substituted by:
   —OH,
   —O-linear (C$_1$-C$_{12}$)-alkyl, preferably a (C$_1$-C$_6$)-alkyl,
   —O-linear (C$_1$-C$_{12}$)-acyl, preferably a (C$_1$-C$_6$)-acyl,
   a halogen atom chosen among Br, Cl, I, F, preferably F,
   a possibly salified or esterified carboxy,
   a possibly salified or esterified carboxy (C$_1$-C$_{12}$)-alkyl, preferably a (C$_1$-C$_6$)-alkyl,
R$_2$, R$_3$ and R$_4$ represent independently from each other:
 a hydrogen atom, or
 a linear or branched (C$_1$-C$_{12}$)-alkyl, preferably a (C$_1$-C$_6$)-alkyl, or
 a linear or branched (C$_1$-C$_{12}$)-acyl, preferably a (C$_1$-C$_6$)-acyl,
R$_5$ represents:
 a hydrogen atom, or
 a linear or branched (C$_1$-C$_{13}$)-alkyl, preferably a (C$_1$-C$_6$)-alkyl, possibly substituted by up to 3 radicals selected from:
  —OH,
  —O-linear (C$_1$-C$_{12}$)-alkyl, preferably a (C$_1$-C$_6$)-alkyl, possibly substituted by an oxo group,
  a halogen atom chosen among Br, Cl, I, F, preferably F,
  a possibly salified or esterified carboxy,
  an oxo group,
  an aromatic or heteroaromatic aryl possibly substituted by:
   —OH,
   —O-linear (C$_1$-C$_{12}$)-alkyl, preferably a (C$_1$-C$_6$)-alkyl,
   a halogen atom chosen among Br, Cl, I, F, preferably F,
   a possibly salified or esterified carboxy,
   a possibly salified or esterified carboxy (C$_1$-C$_{12}$)-alkyl, preferably a (C$_1$-C$_6$)-alkyl,
and R$_5$ can be possibly interrupted by up to 3 heteroatoms selected from O, S or N,
R$_6$ represents:
 a hydrogen atom, or
 a linear or branched (C$_1$-C$_{12}$)-alkyl, preferably a (C$_1$-C$_6$)-alkyl, possibly substituted by up to 3 radicals selected from:
  —OH,
  —O-linear (C$_1$-C$_{12}$)-alkyl, preferably a (C$_1$-C$_6$)-alkyl,
  a halogen atom chosen among Br, Cl, I, F, preferably F,
  a possibly salified or esterified carboxy,
  an oxo group,
  an aromatic or heteroaromatic aryl possibly substituted by:
   —OH,
   —O-linear (C$_1$-C$_{12}$)-alkyl, preferably a (C$_1$-C$_6$)-alkyl,
   a halogen atom chosen among Br, Cl, I, F, preferably F,
   a possibly salified or esterified carboxy,
   a possibly salified or esterified carboxy (C$_1$-C$_{12}$)-alkyl, preferably a (C$_1$-C$_6$)-alkyl, or
 a linear or branched (C$_1$-C$_{12}$)-acyl, preferably a (C$_1$-C$_6$)-acyl, possibly substituted by up to 3 radicals selected from:
  —OH,
  —O-linear (C$_1$-C$_{12}$)-alkyl, preferably a (C$_1$-C$_6$)-alkyl,
  a halogen atom chosen among Br, Cl, I, F, preferably F,
  a possibly salified or esterified carboxy,
  an oxo group,
  an aromatic or heteroaromatic aryl possibly substituted by:
   —OH,
   —O-linear (C$_1$-C$_{12}$)-alkyl, preferably a (C$_1$-C$_6$)-alkyl,
   a halogen atom chosen among Br, Cl, I, F, preferably F,
   a possibly salified or esterified carboxy,
   a possibly salified or esterified carboxy (C$_1$-C$_{12}$)-alkyl, preferably a (C$_1$-C$_6$)-alkyl,
and R$_6$ can be possibly interrupted by up to 3 heteroatoms selected from O, S or N,
or R$_5$ and R$_6$ represent together with the N atom to which R$_6$ is bound and the carbon atom to which R$_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
 —OH,
 —O-linear (C$_1$-C$_{12}$)-alkyl, preferably a (C$_1$-C$_6$)-alkyl,
 a halogen atom chosen among Br, Cl, I, F, preferably F,
 a possibly salified or esterified carboxy,
 an oxo group,
 an aromatic or heteroaromatic aryl possibly substituted by:
  —OH,
  —O-linear (C$_1$-C$_{12}$)-alkyl, preferably a (C$_1$-C$_6$)-alkyl,
  a halogen atom chosen among Br, Cl, I, F, preferably F,
  a possibly salified or esterified carboxy,
  a possibly salified or esterified carboxy (C$_1$-C$_{12}$)-alkyl, preferably a (C$_1$-C$_6$)-alkyl,
and the pharmaceutically acceptable salts, enantiomers, diastereoisomers of same, as well as mixture of same, for their use as antibacterial drugs for the treatment and/or the prevention of infection(s) caused by biofilm-forming bacteria.

The term "carboxy" means a carboxylic acid or a carboxyl group of formula —COOH, the group —COOH being linked to a carbon atom or another element. The group carboxy can be a ($C_1$-$C_{12}$) carboxy, which means that a ($C_1$-$C_{12}$) carboxy contains 1, 2, 3, 4, 5, 6, 7, 8, 9, 10, 11 or 12 carbon atoms. ($C_1$-$C_{12}$) carboxy are for example methanoic acid, acetic acid, propionic acid, butyric acid, valeric acid, caproic acid, enanthic acid, caprylic acid, pelargonic acid, capric acid, undecylic acid, and lauric acid.

The term "salified" means in the form of a salt.

The term "esterified" means that the group carboxy is combined or condensed with an alcohol. For example, an esterified carboxy can be an ethyl ester.

The term "oxo group" means a group containing an oxygen atom, =O, doubly bonded to a carbon atom or another element. The term embraces aldehydes, carboxylic acids, ketones, amides and esters.

The term "aryl" refers to a 6- to 18-membered monocyclic, bicyclic, tricyclic, or polycyclic aromatic or heteroaromatic ring system. Examples of an aryl group include phenyl, benzyl, tolyle, xylyle, benzoyle, benzyliden, naphthyl, pyrenyl, anthracyl, quinolyl, and isoquinolyl . . . . This list is not exhaustive. An aryl group can be unsubstituted or optionally substituted with one or more substituents.

In another embodiment, the present invention relates to compounds of the following formula I:

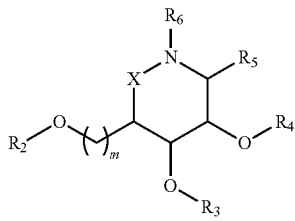

wherein:
m represents an integer being equal to 0, 1, 2,
X represents a simple bond or a radical —$CHR_1$— wherein $R_1$ represents:
  a hydrogen atom, or
  a linear or branched ($C_1$-$C_{12}$)-alkyl, preferably a ($C_1$-$C_6$)-alkyl, possibly interrupted by up to 3 heteroatoms selected from O and/or possibly substituted by up to 3 radicals selected from:
    —OH,
    —O-linear ($C_1$-$C_{12}$)-alkyl, preferably a ($C_1$-$C_6$)-alkyl,
    —O-linear ($C_1$-$C_{12}$)-acyl, preferably a ($C_1$-$C_6$)-acyl,
    a halogen atom F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl, more preferably a ($C_1$-$C_2$)-alkyl,
      a halogen atom F,
      a possibly salified or esterified carboxy,
$R_2$, $R_3$ and $R_4$ represent independently from each other:
  a hydrogen atom, or
  a linear or branched ($C_1$-$C_{12}$)-alkyl, preferably a ($C_1$-$C_6$)-alkyl, more preferably a ($C_1$-$C_3$)-alkyl, or
  a linear or branched ($C_1$-$C_{12}$)-acyl, preferably a ($C_1$-$C_6$)-acyl, more preferably a ($C_1$-$C_3$)-acyl, $R_5$ represents:
  a hydrogen atom, or
  a linear or branched ($C_1$-$C_{13}$)-alkyl, preferably a ($C_1$-$C_6$)-alkyl, possibly substituted by up to 3 radicals selected from:
    —OH,
    —O-linear ($C_1$-$C_{12}$)-alkyl, preferably a ($C_1$-$C_6$)-alkyl, possibly substituted by an oxo group,
    a halogen atom F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl, more preferably a ($C_1$-$C_2$)-alkyl,
      a halogen atom F,
      a possibly salified or esterified carboxy,
and $R_5$ can be possibly interrupted by up to 2 heteroatoms selected from O or N,
$R_6$ represents:
  a hydrogen atom, or
  a linear or branched ($C_1$-$C_{12}$)-alkyl, preferably a ($C_1$-$C_6$)-alkyl, possibly substituted by up to 3 radicals selected from:
    —OH,
    —O-linear ($C_1$-$C_{12}$)-alkyl, preferably a ($C_1$-$C_6$)-alkyl,
    a halogen atom F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl, more preferably ($C_1$-$C_2$)-alkyl,
      a halogen atom F,
      a possibly salified or esterified carboxy, or
  a linear or branched ($C_1$-$C_{12}$)-acyl, preferably a ($C_1$-$C_6$)-acyl, possibly substituted by up to 3 radicals selected from:
    —OH,
    —O-linear ($C_1$-$C_{12}$)-alkyl, preferably a ($C_1$-$C_6$)-alkyl,
    a halogen atom F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl, more preferably ($C_1$-$C_2$)-alkyl,
      a halogen atom F,
      a possibly salified or esterified carboxy,
and $R_6$ can be possibly interrupted by up to 3 heteroatoms selected from O or N,
or $R_5$ and $R_6$ represent together with the N atom to which $R_4$ is bound and the carbon atom to which $R_5$ is bound an alkylene radical Z having 2 to 5 carbon atoms which is possibly interrupted by 1 or 2 heteroatoms selected from O and N and/or terminated by an heteroatom selected from O and N and/or possibly substituted by up to three radicals selected from:
  —OH,
  —O-linear ($C_1$-$C_{12}$)-alkyl, preferably a ($C_1$-$C_6$)-alkyl,
  a halogen atom F,
  a possibly salified or esterified carboxy,
  an oxo group,
  an aromatic or heteroaromatic aryl possibly substituted by:

—OH,
—O-linear $(C_1-C_{12})$-alkyl, preferably a $(C_1-C_6)$-alkyl, more preferably a $(C_1-C_2)$-alkyl,
a halogen atom F,
a possibly salified or esterified carboxy,
and the pharmaceutically acceptable salts, enantiomers, diastereoisomers of same, as well as mixture of same, for their use as antibacterial drugs for the treatment and/or the prevention of infection(s) caused by biofilm-forming bacteria.

In another embodiment, the present invention relates to compounds of formula I for their use as antibacterial drugs in the treatment and/or the prevention of infection(s) caused by the formation of biofilm by biofilm-forming bacteria.

There are five stages of biofilm development:
1. Initial attachment
2. Irreversible attachment
3. Maturation I
4. Maturation II
5. Dispersion Initial attachment is the adsorption of the mobiles microorganisms in solution liquid or inert surface. This is a fast phenomenon.

Irreversible attachment is characterized by the adhesion of microorganisms as a result of physico-chemical interactions of forces attraction (Van der Waals) and repulsive (electrostatic and acid-base). The first fixed microorganisms increase the ability to anchor other microorganisms by increasing and varying the anchoring surfaces.

Maturation I is the step where the microorganisms multiply and stimulates the synthesis of polysaccharides entering into the composition of the biofilm exocellular polymers: the exopolymers. The production of these exopolymers leads to the formation of a matrix of exocellular and extracellular polymeric substances (EPS).

Maturation II is the step where the biofilm grows and matures. The biofilm thickens and can become macroscopic or giant with optimal conditions.

Dispersion is the last step and constitutes the dissolution of the biofilm. This can appear, for example with changes in nutrient intake of the biofilm, fluctuations in local concentrations of oxygen or the increase of nitric oxide. After dispersion the microorganisms return to the planktonic state. However, this last step rarely occur with pathogenic biofilms.

More information about the biofilm formation is available in a book entitled Bacterial Biofilms, Springer, Series: *Current Topics in Microbiology and Immunology*, Vol. 322. Romeo, Tony (Ed.) 2008 and also in recent review articles: *Pseudomonas* biofilms: possibilities of their control. Masák J, Cejková A, Schreiberová O, Rezanka T., FEMS Microbiol Ecol. 2014 July; 89(1):1-14 and Biofilm formation and persistence on abiotic surfaces in the context of food and medical environments. Abdallah M, Benoliel C, Drider D, Dhulster P, Chihib N E. *Arch Microbiol.* 2014 July; 196(7): 453-72.

Determination of the biofilm formation stages can be done experimentally by comparing data obtained from scanning microscopy with optical density of the biofilm stained with different methods.

Early biofilm corresponds to the step of described here as maturation I. It corresponds to the development of the biofilm, from 0 hour to 48 hours, starting from the initial attachment. Thus, 48 hours starting from the initial attachment corresponds to the step of maturation I.

The expression "from 0 hour to 48 hours" means each hour between 0 and 48, that is to say, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 and 48.

Mature Biofilm corresponds to the step described here as maturation II. It corresponds to the development of the biofilm, from 48 hours to 96 hours, starting from the initial attachment. In fact, mature biofilm is a biofilm which is fully formed.

The expression "from 48 hours to 96 hours" means each hour between 48 and 96, that is to say, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 and 96.

In fact, early biofilm stage ends at 48 hours from the initial attachment and mature biofilm stage starts at 48 hours from the initial attachment.

In a preferred embodiment of the present invention, the term "biofilm" means an "early biofilm".

More preferably, the early biofils is at the step described here as maturation I.

Experiments performed in in vitro conditions indicate that iminosugars according to the present invention inhibit early biofilm formation when exopolysaccharide chains are synthesized by already attached bacteria. Thus iminosugars according to the present invention do not interact neither with attachment phase nor with maturation II step. They also do not interfere with bacterial multiplication.

In another embodiment, the present invention relates to compounds of formula I for their above-mentioned use, wherein the bacteria are of the genus *Pseudomonas*, in particular *Pseudomonas aeruginosa* species. *Pseudomonas* is a genus of gram-negative bacteria.

In a preferred embodiment, the bacteria of the present invention are gram-negative bacteria.

In a second embodiment, the present invention relates to compounds of the following formula I:

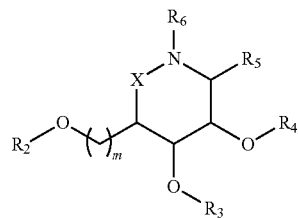

wherein:
m represents an integer being equal to 0, 1, 2, 3, 4, 5 or 6,
X represents a simple bond or a radical —$CHR_1$— wherein $R_1$ represents:
  a hydrogen atom, or
  a linear or branched, possibly interrupted by up to 3 heteroatoms selected from O, S or N and/or possibly substituted, $(C_1-C_{12})$-alkyl,
$R_2$, $R_3$ and $R_4$ represent independently from each other:
  a hydrogen atom, or
  a linear or branched $(C_1-C_{12})$-alkyl, or
  a linear or branched $(C_1-C_{12})$-acyl,
$R_5$ represents:
  a hydrogen atom, or
  a linear or branched, possibly substituted, $(C_1-C_{13})$-alkyl, or
  a linear or branched, possibly substituted $(C_1-C_{13})$-alkyl interrupted by up to 3 heteroatoms selected from O, S or N, $R_6$ represents:
 a hydrogen atom, or
 a linear or branched possibly substituted $(C_1\text{-}C_{12})$-alkyl, or
 a linear or branched possibly substituted $(C_1\text{-}C_{12})$-acyl, or
 a linear or branched, possibly substituted $(C_1\text{-}C_{12})$-alkyl interrupted by up to 3 heteroatoms selected from O, S or N, or
 a linear or branched, possibly substituted $(C_1\text{-}C_{12})$-acyl interrupted by up to 3 heteroatoms selected from O, S or N,
or $R_5$ and $R_6$ represent together with the N atom to which $R_6$ is bound and the carbon atom to which $R_5$ is bound an alkylene radical Z having 2 to 5 carbon atoms which is possibly substituted and/or possibly interrupted by up to 3 heteroatoms selected from O, S, N and/or terminated by an heteroatom selected from O, S, N,
and the pharmaceutically acceptable salts, enantiomers, diastereoisomers of same, as well as mixture of same, for their use for the treatment and/or the prevention of biofilm formation.

The expression "the treatment and/or the prevention of biofilm formation" means the inhibition of the biofilm formation. It can also mean the reduction of the biofilm formation or the reduction of the biofilm growth.

The expression "the treatment and/or the prevention of biofilm formation" means also indirect antibacterial properties. This means that the compounds of the invention do no kill directly the bacterias, but prevent them to create or develop their biofilm.

The expression "the treatment and/or the prevention of biofilm formation" means also the treatment and/or the prevention of infections involving the biofilm formation by bacteria, notably bacteria of the genus *Pseudomonas*, more particularly *Pseudomonas aeruginosa*.

According to the present invention, the prevention of biofilm formation means an action on early biofilm, and no action on mature biofilm. On the contrary, the treatment of biofilm formation means an action on mature biofilm, and no action on early biofilm.

In a preferred embodiment, the compounds of formula I according to the present invention inhibit the biofilm formation at the step described here as maturation I.

In a preferred embodiment, the compounds of formula I according to the present invention inhibit the formation of the early biofilm.

In another embodiment, the present invention relates to compounds of formula I, for their use for the treatment and/or the prevention of biofilm formation by bacteria of the genus *Pseudomonas*, preferably *Pseudomonas aeruginosa*.

In another embodiment, the present invention relates to compounds of the following formula I:

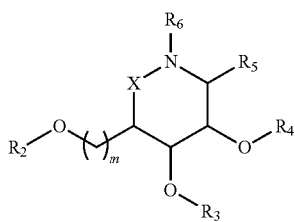

wherein:
m represents an integer being equal to 0, 1, 2, 3, 4, 5 or 6,
X represents a simple bond or a radical —$CHR_1$— wherein $R_1$ represents:
 a hydrogen atom, or
 a linear or branched $(C_1\text{-}C_{12})$-alkyl, preferably a $(C_1\text{-}C_6)$-alkyl, possibly interrupted by up to 3 heteroatoms selected from O, S or N and/or possibly substituted by up to 3 radicals selected from:
  —OH,
  —O-linear $(C_1\text{-}C_{12})$-alkyl, preferably a $(C_1\text{-}C_6)$-alkyl,
  —O-linear $(C_1\text{-}C_{12})$-acyl, preferably a $(C_1\text{-}C_6)$-acyl,
  a halogen atom chosen among Br, Cl, I, F, preferably F,
  a possibly salified or esterified carboxy,
  an oxo group,
  an aromatic or heteroaromatic aryl possibly substituted by:
   —OH,
   —O-linear $(C_1\text{-}C_{12})$-alkyl, preferably a $(C_1\text{-}C_6)$-alkyl,
   —O-linear $(C_1\text{-}C_{12})$-acyl, preferably a $(C_1\text{-}C_6)$-acyl,
   a halogen atom chosen among Br, Cl, I, F, preferably F,
   a possibly salified or esterified carboxy,
   a possibly salified or esterified carboxy $(C_1\text{-}C_{12})$-alkyl, preferably a $(C_1\text{-}C_6)$-alkyl,
$R_2$, $R_3$ and $R_4$ represent independently from each other:
 a hydrogen atom, or
 a linear or branched $(C_1\text{-}C_{12})$-alkyl, preferably a $(C_1\text{-}C_6)$-alkyl, or
 a linear or branched $(C_1\text{-}C_{12})$-acyl, preferably a $(C_1\text{-}C_6)$-acyl,
$R_5$ represents:
 a hydrogen atom, or
 a linear or branched $(C_1\text{-}C_{13})$-alkyl, preferably a $(C_1\text{-}C_6)$-alkyl, possibly substituted by up to 3 radicals selected from:
  —OH,
  —O-linear $(C_1\text{-}C_{12})$-alkyl, preferably a $(C_1\text{-}C_6)$-alkyl, possibly substituted by an oxo group,
  a halogen atom chosen among Br, Cl, I, F, preferably F,
  a possibly salified or esterified carboxy,
  an oxo group,
  an aromatic or heteroaromatic aryl possibly substituted by:
   —OH,
   —O-linear $(C_1\text{-}C_{12})$-alkyl, preferably a $(C_1\text{-}C_6)$-alkyl,
   a halogen atom chosen among Br, Cl, I, F, preferably F,
   a possibly salified or esterified carboxy,
   a possibly salified or esterified carboxy $(C_1\text{-}C_{12})$-alkyl, preferably a $(C_1\text{-}C_6)$-alkyl,
and $R_5$ can be possibly interrupted by up to 3 heteroatoms selected from O, S or N,
$R_6$ represents:
 a hydrogen atom, or
 a linear or branched $(C_1\text{-}C_{12})$-alkyl, preferably a $(C_1\text{-}C_6)$-alkyl, possibly substituted by up to 3 radicals selected from:
  —OH,
  —O-linear $(C_1\text{-}C_{12})$-alkyl, preferably a $(C_1\text{-}C_6)$-alkyl,
  a halogen atom chosen among Br, Cl, I, F, preferably F,
  a possibly salified or esterified carboxy,
  an oxo group, an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, or
a linear or branched ($C_1$-$C_{12}$)-acyl, preferably a ($C_1$-$C_6$)-acyl, possibly substituted by up to 3 radicals selected from:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl,
and $R_6$ can be possibly interrupted by up to 3 heteroatoms selected from O, S or N,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl,
and the pharmaceutically acceptable salts, enantiomers, diastereoisomers of same, as well as mixture of same, for their use in the treatment and/or the prevention of biofilm formation in particular the treatment and/or the prevention of biofilm formation by bacteria of the genus *Pseudomonas*, preferably *Pseudomonas aeruginosa*.

In another embodiment, the present invention relates to compounds of the following formula I:

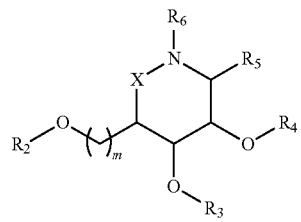

wherein:
m represents an integer being equal to 0, 1, 2,
X represents a simple bond or a radical —$CHR_1$— wherein
$R_1$ represents:
a hydrogen atom, or
a linear or branched ($C_1$-$C_{12}$)-alkyl, preferably a ($C_1$-$C_6$)-alkyl, possibly interrupted by up to 3 heteroatoms selected from O and/or possibly substituted by up to 3 radicals selected from:
—OH,
—O-linear ($C_1$-$C_{12}$)-alkyl, preferably a ($C_1$-$C_6$)-alkyl,
—O-linear ($C_1$-$C_{12}$)-acyl, preferably a ($C_1$-$C_6$)-acyl,
a halogen atom F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl, more preferably a ($C_1$-$C_2$)-alkyl,
—O-linear ($C_1$-$C_{12}$)-acyl, preferably a ($C_1$-$C_6$)-acyl, more preferably a ($C_1$-$C_2$)-acyl,
a halogen atom F,
a possibly salified or esterified carboxy,
$R_2$, $R_3$ and $R_4$ represent independently from each other:
a hydrogen atom, or
a linear or branched ($C_1$-$C_{12}$)-alkyl, preferably a ($C_1$-$C_6$)-alkyl, more preferably a ($C_1$-$C_3$)-alkyl, or
a linear or branched ($C_1$-$C_{12}$)-acyl, preferably a ($C_1$-$C_6$)-acyl, more preferably a ($C_1$-$C_3$)-acyl,
$R_5$ represents:
a hydrogen atom, or
a linear or branched ($C_1$-$C_{13}$)-alkyl, preferably a ($C_1$-$C_6$)-alkyl, possibly substituted by up to 3 radicals selected from:
—OH,
—O-linear ($C_1$-$C_{12}$)-alkyl, preferably a ($C_1$-$C_6$)-alkyl, possibly substituted by an oxo group,
a halogen atom F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl, more preferably a ($C_1$-$C_2$)-alkyl,
a halogen atom F,
a possibly salified or esterified carboxy,
and $R_5$ can be possibly interrupted by up to 2 heteroatoms selected from O or N,
$R_6$ represents:
a hydrogen atom, or
a linear or branched ($C_1$-$C_{12}$)-alkyl, preferably a ($C_1$-$C_6$)-alkyl, possibly substituted by up to 3 radicals selected from:

—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably $(C_1-C_2)$-alkyl,
a halogen atom F,
a possibly salified or esterified carboxy, or
a linear or branched $(C_1-C_{12})$-acyl, preferably a $(C_1-C_6)$-acyl, possibly substituted by up to 3 radicals selected from:
—OH,
—O-linear $(C_1-C_{12})$alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably $(C_1-C_2)$-alkyl,
a halogen atom F,
a possibly salified or esterified carboxy,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O and N and/or terminated by an heteroatom selected from O and N and/or possibly substituted by up to three radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably a $(C_1-C_2)$-alkyl
a halogen atom F,
a possibly salified or esterified carboxy,
and the pharmaceutically acceptable salts, enantiomers, diastereoisomers of same, as well as mixture of same, for their use for the treatment and/or the prevention of biofilm formation.

In a third embodiment, the present invention relates to compounds of formula I for their above-mentioned uses, the said compounds corresponding to compounds of the following formula II:

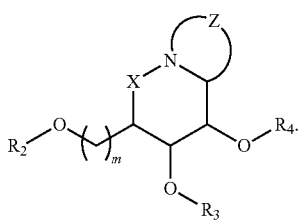

wherein:
m represents an integer being equal to 0, 1, 2, 3, 4, 5 or 6,
X represents a simple bond or a radical —$CHR_1$— wherein $R_1$ represents:
a hydrogen atom, or
a linear or branched, possibly interrupted by up to 3 heteroatoms selected from O, S or N and/or possibly substituted, $(C_1-C_{12})$-alkyl,
$R_2$, $R_3$ and $R_4$ represent independently from each other:
a hydrogen atom, or
a linear or branched $(C_1-C_{12})$-alkyl, or
a linear or branched $(C_1-C_{12})$-acyl,
Z represents an alkylene radical having 2 to 5 carbon atoms which is possibly substituted and/or possibly interrupted by up to 3 heteroatoms selected from O, S, N and/or terminated by an heteroatom selected from O, S, N,
and the pharmaceutically acceptable salts, enantiomers, diastereoisomers of same, as well as mixture of same.

Thus, the compounds of formula II can be used as antibacterial drugs for the treatment and/or the prevention of infection(s) caused by biofilm-forming bacteria.

The compounds of formula II can also be used for the treatment and/or the prevention of biofilm formation.

In another embodiment, the present invention relates to compounds of formula I for their above-mentioned uses, the said compounds corresponding to compounds of the following formula II:

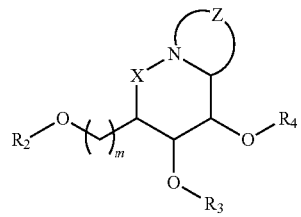

wherein:
m represents an integer being equal to 0, 1, 2, 3, 4, 5 or 6,
X represents a simple bond or a radical —$CHR_1$— wherein $R_1$ represents:
a hydrogen atom, or
a linear or branched $(C_1-C_{12})$-alkyl, preferably a $(C_1-C_6)$-alkyl, possibly interrupted by up to 3 heteroatoms selected from O, S or N and/or possibly substituted by up to 3 radicals selected from:
—OH,
—O-linear $(C_1-C_{12})$-alkyl, preferably a $(C_1-C_6)$-alkyl,
—O-linear $(C_1-C_{12})$-acyl, preferably a $(C_1-C_6)$-acyl,
a halogen atom chosen among Br, Cl, I, F, preferably F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl,
—O-linear $(C_1-C_{12})$-acyl, preferably a $(C_1-C_6)$-acyl,
a halogen atom chosen among Br, Cl, I, F, preferably F,
a possibly salified or esterified carboxy,
a possibly salified or esterified carboxy $(C_1-C_{12})$-alkyl, preferably a $(C_1-C_6)$-alkyl, R$_2$, R$_3$ and R$_4$ represent independently from each other:
  a hydrogen atom, or
  a linear or branched (C$_1$-C$_{12}$)-alkyl, preferably a (C$_1$-C$_6$)-alkyl, or
  a linear or branched (C$_1$-C$_{12}$)-acyl, preferably a (C$_1$-C$_6$)-acyl,
Z represents an alkylene radical having 2 to 5 carbon atoms which is possibly interrupted by 1 or 2 heteroatoms selected from O, S, N and/or terminated by an heteroatom selected from O, S, N and/or possibly substituted by up to three radicals selected from:
  —OH,
  —O-linear (C$_1$-C$_{12}$)-alkyl, preferably a (C$_1$-C$_6$)-alkyl,
  a halogen atom chosen among Br, Cl, I, F, preferably F,
  a possibly salified or esterified carboxy,
  an oxo group,
  an aromatic or heteroaromatic aryl possibly substituted by:
    —OH,
    —O-linear (C$_1$-C$_{12}$)-alkyl, preferably a (C$_1$-C$_6$)-alkyl,
    a halogen atom chosen among Br, Cl, I, F, preferably F,
    a possibly salified or esterified carboxy,
    a possibly salified or esterified carboxy (C$_1$-C$_{12}$)-alkyl, preferably a (C$_1$-C$_6$)-alkyl,
and the pharmaceutically acceptable salts, enantiomers, diastereoisomers of same, as well as mixture of same.

In another embodiment, the present invention relates to compounds of formula I for their above-mentioned uses, the said compounds corresponding to compounds of the following formula II:

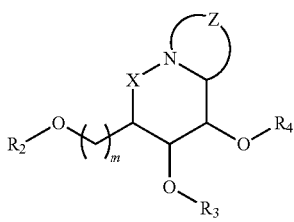

wherein:
m represents an integer being equal to 0, 1, 2,
X represents a simple bond or a radical —CHR$_1$— wherein R$_1$ represents:
  a hydrogen atom, or
  a linear or branched (C$_1$-C$_{12}$)-alkyl, preferably a (C$_1$-C$_6$)-alkyl, possibly interrupted by up to 3 heteroatoms selected from O and/or possibly substituted by up to 3 radicals selected from:
    —OH,
    —O-linear (C$_1$-C$_{12}$)-alkyl, preferably a (C$_1$-C$_6$)-alkyl,
    —O-linear (C$_1$-C$_{12}$)-acyl, preferably a (C$_1$-C$_6$)-acyl,
    a halogen atom F,
    a possibly salified or esterified carboxy,
    an oxo group,
    an aromatic or heteroaromatic aryl possibly substituted by:
      —OH,
      —O-linear (C$_1$-C$_{12}$)-alkyl, preferably a (C$_1$-C$_6$)-alkyl, more preferably a (C$_1$-C$_2$)-alkyl,
      —O-linear (C$_1$-C$_{12}$)-acyl, preferably a (C$_1$-C$_6$)-acyl, more preferably a (C$_1$-C$_2$)-acyl,
      a halogen atom F,
      a possibly salified or esterified carboxy, R$_2$, R$_3$ and R$_4$ represent independently from each other:
  a hydrogen atom, or
  a linear or branched (C$_1$-C$_{12}$)-alkyl, preferably a (C$_1$-C$_6$)-alkyl, more preferably a (C$_1$-C$_3$)-alkyl,
  a linear or branched (C$_1$-C$_{12}$)-acyl, preferably a (C$_1$-C$_6$)-acyl, more preferably a (C$_1$-C$_3$)-acyl,
Z represents an alkylene radical having 2 to 5 carbon atoms which is possibly interrupted by 1 or 2 heteroatoms selected from O and N and/or terminated by an heteroatom selected from O and N and/or possibly substituted by up to three radicals selected from:
  —OH,
  —O-linear (C$_1$-C$_{12}$)-alkyl, preferably a (C$_1$-C$_6$)-alkyl,
  a halogen atom F,
  a possibly salified or esterified carboxy,
  an oxo group,
  an aromatic or heteroaromatic aryl possibly substituted by:
    —OH,
    —O-linear (C$_1$-C$_{12}$)-alkyl, preferably a (C$_1$-C$_6$)-alkyl, more preferably a (C$_1$-C$_2$)-alkyl
    a halogen atom F,
    a possibly salified or esterified carboxy,
and the pharmaceutically acceptable salts, enantiomers, diastereoisomers of same, as well as mixture of same.

In another embodiment, the present invention also relates to compounds of formula I for their above-mentioned uses, the said compounds corresponding to compounds of the following formula V:

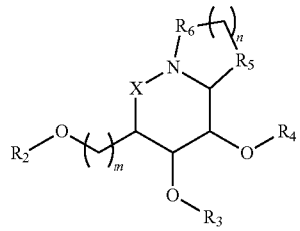

wherein X, m, R2, R3, R4, R5 and R6 are as previously defined, and n being an integer being equal to 1, 2, 3,
and the pharmaceutically acceptable salts, enantiomers, diastereoisomers of same, as well as mixture of same.

In another embodiment, the present invention also relates to compounds of formula I for their above-mentioned uses, the said compounds corresponding to compounds of the following formula VII:

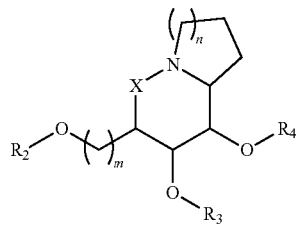

wherein X, m, R2, R3 and R4 are as previously defined, and n being an integer being equal to 1, 2, 3,
and the pharmaceutically acceptable salts, enantiomers, diastereoisomers of same, as well as mixture of same.

In another embodiment, the present invention also relates to compounds of formula I for their above-mentioned uses, the said compounds corresponding to compounds of the following formula IX:

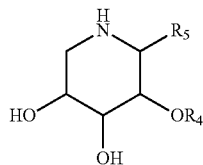

wherein R4 and R5 is as previously defined,
and the pharmaceutically acceptable salts, enantiomers, diastereoisomers of same, as well as mixture of same.

In another embodiment, the present invention also relates to compounds of formula I for their above-mentioned uses, the said compounds corresponding to compounds of the following formula X:

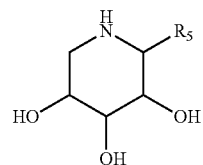

wherein R5 is as previously defined,
and the pharmaceutically acceptable salts, enantiomers, diastereoisomers of same, as well as mixture of same.

In another embodiment, the present invention also relates to compounds of formula I for their above-mentioned uses, the said compounds corresponding to compounds of the following formula XI:

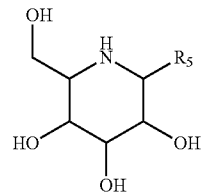

wherein R5 is as previously defined,
and the pharmaceutically acceptable salts, enantiomers, diastereoisomers of same, as well as mixture of same.

In another embodiment, the present invention also relates to compounds of formula I for their above-mentioned uses, the said compounds corresponding to compounds of the following formula XII:

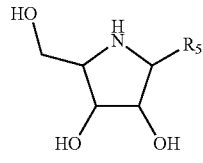

wherein R5 is as previously defined,
and the pharmaceutically acceptable salts, enantiomers, diastereoisomers of same, as well as mixture of same.

In a preferred embodiment, in the compounds of the present invention, notably for the above-mentioned uses, m represents 1 if X is a simple bond and m represents 0 if X is —$CHR_1$—, and $R_2$, $R_3$, $R_4$ and $R_6$ represent a hydrogen atom.

In another embodiment, the present invention also relates to compounds of formula I for their above-mentioned uses, the said compounds corresponding to compounds of the following formula XII:

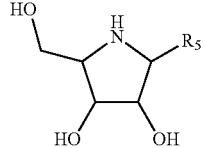

wherein R5 represents:
a linear or branched $(C_1-C_{13})$-alkyl, preferably a $(C_1-C_6)$-alkyl, possibly substituted by up to 3 radicals selected from:
a possibly salified or esterified carboxy,
an aromatic or heteroaromatic aryl possibly substituted by:
—O-linear $(C_1-C_{12})$ alkyl, preferably a $(C_1-C_6)$-alkyl
and $R_5$ can be possibly interrupted by up to 3 heteroatoms selected from O, S or N, notably N preferably, with the proviso that $R_5$ cannot be a linear $C_4$-alkyl if $R_2$, $R_3$ and $R_4$ are hydrogen atom,
and the pharmaceutically acceptable salts, enantiomers, diastereoisomers of same, as well as mixture of same.

In another embodiment, the present invention also relates to compounds of formula I for their above-mentioned uses, the said compounds corresponding to compounds of the following formula II:

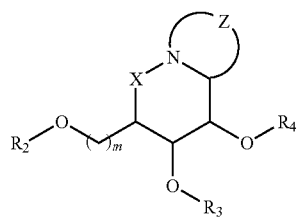

wherein:
m represents 1,
X represents a simple bond,
$R_2$, $R_3$ and $R_4$ represent a hydrogen atom,
$R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N, notably N, and/or terminated by an heteroatom selected from O, S, N and/or possibly substituted by up to three radicals selected from:
a possibly salified or esterified carboxy,
an oxo group,
an aromatic or heteroaromatic aryl possibly substituted by:
O-linear $(C_1-C_{12})$-alkyl, preferably a $(C_1-C_6)$-alkyl,
and the pharmaceutically acceptable salts, enantiomers, diastereoisomers of same, as well as mixture of same.

Thus, the compounds of formula V, VII, IX, X, XI, XII as defined in the present invention can be used as antibacterial drugs for the treatment and/or the prevention of infection(s) caused by biofilm-forming bacteria.

The compounds of formula V, VII, IX, X, XI, XII as defined in the present invention can also be used for the treatment and/or the prevention of biofilm formation.

The compounds of formula III, IV, VI, VIII as defined in the present invention can be used as antibacterial drugs for the treatment and/or the prevention of infection(s) caused by biofilm-forming bacteria.

The compounds of formula III, IV, VI, VIII as defined in the present invention can also be used for the treatment and/or the prevention of biofilm formation.

In another embodiment, the present invention also relates to compounds of formula I, II, III, IV, V, VI, VII, VIII, IX, X, XI or XII for their above-mentioned uses, wherein:

m represents an integer being equal to 0 or 1,

X represents a simple bond or a radical —$CHR_1$— wherein $R_1$ represents:
- a hydrogen atom, or
- a linear or branched ($C_1$-$C_{12}$)-alkyl, preferably a ($C_1$-$C_6$)-alkyl, possibly interrupted by up to 3 heteroatoms selected from O, S or N and/or possibly substituted by —OH, $R_2$, $R_3$ and $R_4$ represent independently from each other:
- a hydrogen atom, or
- a linear or branched ($C_1$-$C_{12}$)-alkyl, preferably a ($C_1$-$C_6$)-alkyl, or $R_5$ represents:
- a hydrogen atom, or
- a linear or branched ($C_1$-$C_{13}$)-alkyl, preferably a ($C_1$-$C_6$)-alkyl, possibly substituted by up to 3 radicals selected from:
  - —OH,
  - —O-linear ($C_1$-$C_{12}$)-alkyl, preferably a ($C_1$-$C_6$)-alkyl, possibly substituted by an oxo group,
  - a possibly salified or esterified carboxy,
  - an oxo group,
  - an aromatic or heteroaromatic aryl possibly substituted by:
    - —OH,
    - —O-linear ($C_1$-$C_{12}$)-alkyl, preferably a ($C_1$-$C_6$)-alkyl, and $R_5$ can be possibly interrupted by up to 3 heteroatoms selected from O, S or N, $R_6$ represents a hydrogen atom, or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
- a possibly salified or esterified carboxy,
- an oxo group,
- an aromatic or heteroaromatic aryl possibly substituted by
  - —O-linear ($C_1$-$C_{12}$)-alkyl, preferably a ($C_1$-$C_6$)-alkyl, and the pharmaceutically acceptable salts, enantiomers, diastereoisomers of same, as well as mixture of same.

In another embodiment, the present invention also relates to compounds of formula I, II, III, IV, V, VI, VII, VIII, IX, X, XI or XII for their above-mentioned uses, wherein:

$R_5$ represents:
- a linear or branched ($C_1$-$C_{13}$)-alkyl, preferably a ($C_1$-$C_6$)-alkyl, possibly substituted by up to 3 radicals selected from:
  - —OH,
  - —O-linear ($C_1$-$C_{12}$)-alkyl, preferably a ($C_1$-$C_6$)-alkyl, possibly substituted by an oxo group,
  - a possibly salified or esterified carboxy,
  - an oxo group,
  - an aromatic or heteroaromatic aryl possibly substituted by:
    - —O-linear ($C_1$-$C_{12}$)-alkyl, preferably a ($C_1$-$C_6$)-alkyl, and $R_5$ can be possibly interrupted by up to 3 heteroatoms selected from O, S or N, notably O and N, $R_6$ represents a hydrogen atom, or or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
- a possibly salified or esterified carboxy,
- an oxo group,
- an aromatic or heteroaromatic aryl possibly substituted by:
  - O-linear ($C_1$-$C_{12}$)-alkyl, preferably a ($C_1$-$C_6$)-alkyl, and the pharmaceutically acceptable salts, enantiomers, diastereoisomers of same, as well as mixture of same.

In another embodiment, the present invention also relates to compounds of formula I, II, III, IV, V, VI, VII, VIII, IX, X, XI or XII for their above-mentioned uses, wherein:

$R_5$ represents:
- a linear or branched ($C_1$-$C_{13}$)-alkyl, preferably a ($C_1$-$C_6$)-alkyl, possibly substituted by up to 3 radicals selected from:
  - —O-linear ($C_1$-$C_{12}$)-alkyl, preferably a ($C_1$-$C_6$)-alkyl, possibly substituted by an oxo group,
  - a possibly salified or esterified carboxy,
  - an oxo group,
  - an aromatic or heteroaromatic aryl possibly substituted by:
    - —O-linear ($C_1$-$C_{12}$)-alkyl, preferably a ($C_1$-$C_6$)-alkyl, and $R_5$ can be possibly interrupted by up to 3 heteroatoms selected from O or N, notably with the proviso that $R_5$ cannot be a linear $C_4$-alkyl if $R_2$, $R_3$ and $R_4$ are hydrogen atom, $R_6$ represents a hydrogen atom, or or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and substituted by up to three radicals selected from:
- a possibly salified or esterified carboxy,
- an oxo group,
- an aromatic or heteroaromatic aryl possibly substituted by:
  - O-linear ($C_1$-$C_{12}$)-alkyl, preferably a ($C_1$-$C_6$)-alkyl, and the pharmaceutically acceptable salts, enantiomers, diastereoisomers of same, as well as mixture of same.

In another embodiment, the present invention also relates to compounds of formula I, II, III, IV, V, VI, VII, VIII, IX, X, XI or XII for their above-mentioned uses, wherein:

$R_5$ represents:
- a linear or branched ($C_1$-$C_{13}$)-alkyl, preferably a ($C_1$-$C_6$)-alkyl, possibly substituted by up to 3 radicals selected from:

—OH,
—O-linear ($C_1$-$C_{12}$)-alkyl, preferably a ($C_1$-$C_6$)-alkyl, possibly substituted by an oxo group,
an oxo group,
and the pharmaceutically acceptable salts, enantiomers, diastereoisomers of same, as well as mixture of same.
In another embodiment, the present invention relates to compounds for their above-mentioned uses, the said compounds having the following formula:
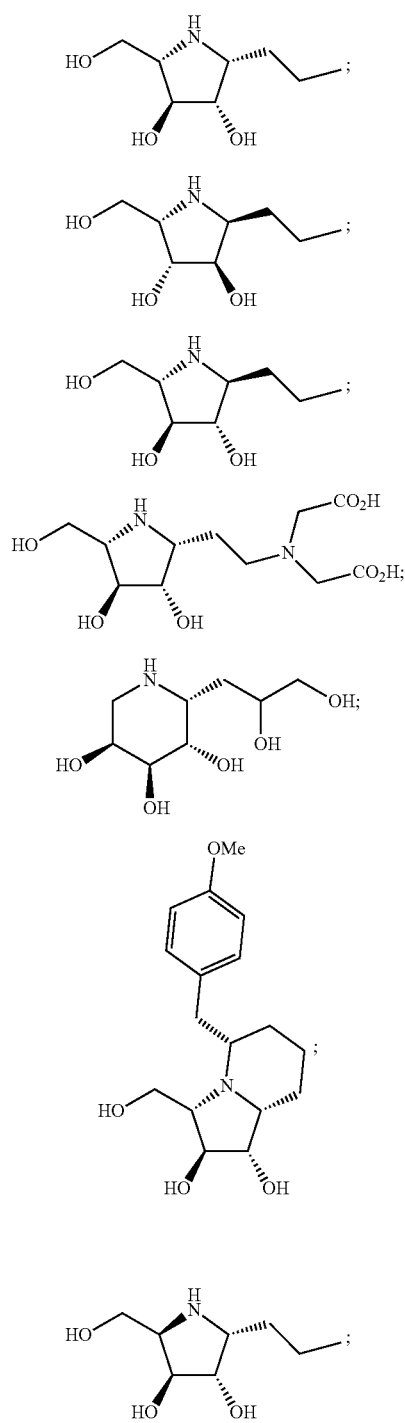
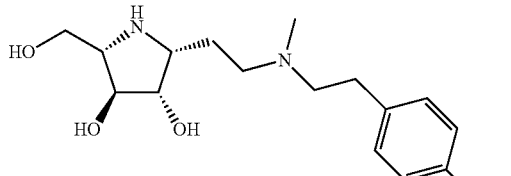
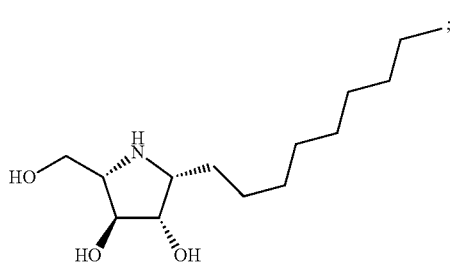
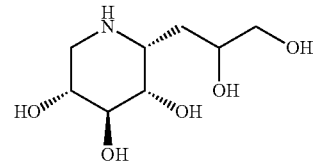
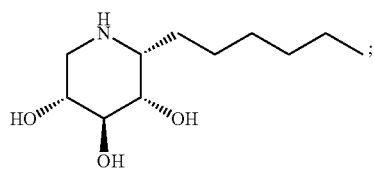
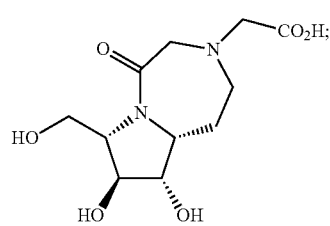
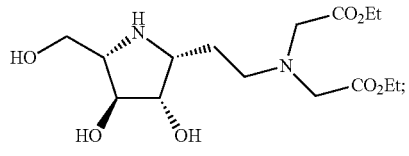
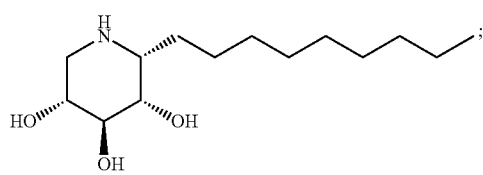
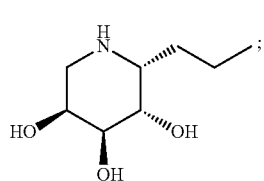

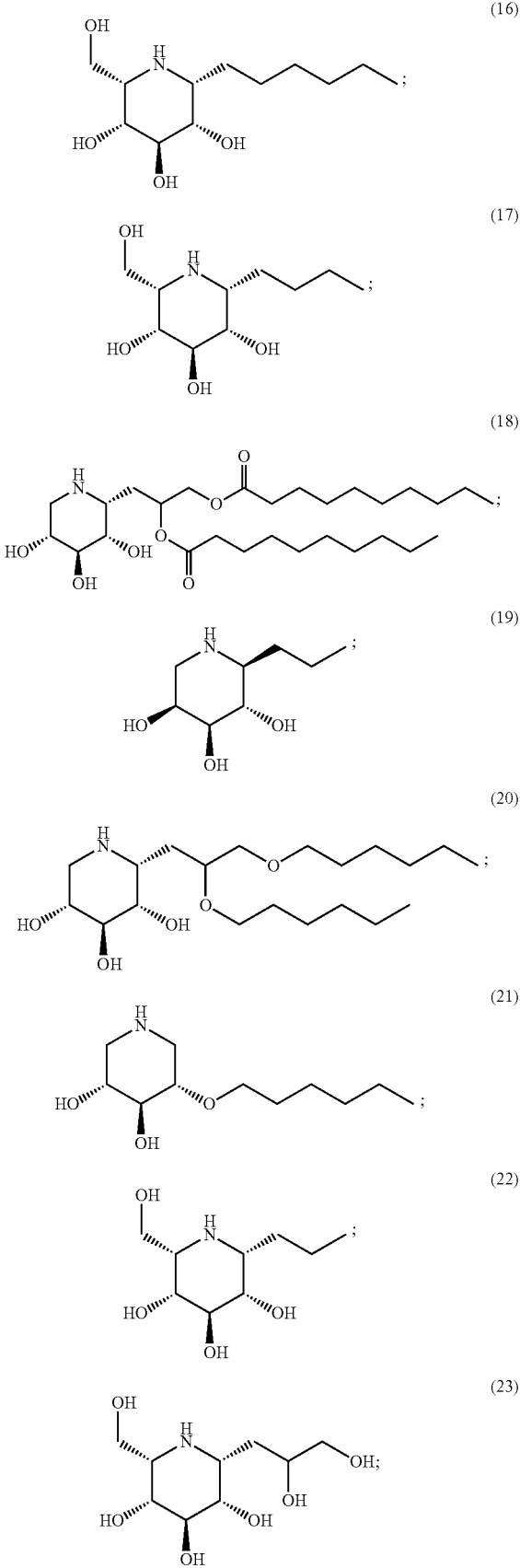

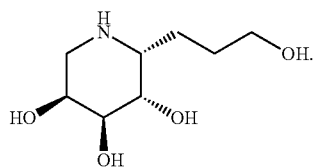

In a fourth embodiment, the present invention relates to compounds of the following formula III:

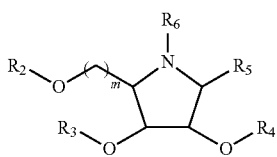

wherein:

m represents an integer being equal to 0, 1, 2, 3, 4, 5 or 6, $R_2$, $R_3$ and $R_4$ represent independently from each other:
- a hydrogen atom, or
- a linear or branched ($C_1$-$C_{12}$)-alkyl, or
- a linear or branched ($C_1$-$C_{12}$)-acyl, $R_5$ represents:
- a hydrogen atom, or
- a linear or branched, possibly substituted, ($C_1$-$C_{13}$)-alkyl, or
- a linear or branched, possibly substituted ($C_1$-$C_{13}$)-alkyl interrupted by up to 3 heteroatoms selected from O, S or N, $R_6$ represents:
- a hydrogen atom, or
- a linear or branched possibly substituted ($C_1$-$C_{12}$)-alkyl, or
- a linear or branched possibly substituted ($C_1$-$C_{12}$)-acyl, or
- a linear or branched, possibly substituted ($C_1$-$C_{12}$)-alkyl interrupted by up to 3 heteroatoms selected from O, S or N, or
- a linear or branched, possibly substituted ($C_1$-$C_{12}$)-acyl interrupted by up to 3 heteroatoms selected from O, S or N, or $R_5$ and $R_6$ represent together with the N atom to which $R_6$ is bound and the carbon atom to which $R_5$ is bound an alkylene radical Z having 2 to 5 carbon atoms which is possibly substituted and/or possibly interrupted by up to 3 heteroatoms selected from O, S, N and/or terminated by an heteroatom selected from O, S, N, and the pharmaceutically acceptable salts, enantiomers, diastereoisomers of same, as well as mixture of same, with the proviso that the following compounds are excluded:

(6)

In another embodiment, the present invention relates to compounds of the following formula III:

wherein:
m represents an integer being equal to 0, 1, 2, 3, 4, 5 or 6,
$R_2$, $R_3$ and $R_4$ represent independently from each other:
  a hydrogen atom, or
  a linear or branched ($C_1$-$C_{12}$)-alkyl, preferably a ($C_1$-$C_6$)-alkyl, or
  a linear or branched ($C_1$-$C_{12}$)-acyl, preferably a ($C_1$-$C_6$)-acyl,
$R_5$ represents:
  a hydrogen atom, or
  a linear or branched ($C_1$-$C_{13}$)-alkyl, preferably a ($C_1$-$C_6$)-alkyl, possibly substituted by up to 3 radicals selected from:
    —OH,
    —O-linear ($C_1$-$C_{12}$)-alkyl, preferably a ($C_1$-$C_6$)-alkyl, possibly substituted by an oxo group,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl,
      a halogen atom chosen among Br, Cl, I, F, preferably F,
      a possibly salified or esterified carboxy,
      a possibly salified or esterified carboxy ($C_1$-$C_{12}$)-alkyl, preferably a ($C_1$-$C_6$)-alkyl,
and $R_5$ can be possibly interrupted by up to 3 heteroatoms selected from O, S or N, $R_6$ represents:
  a hydrogen atom, or
  a linear or branched ($C_1$-$C_{12}$)-alkyl, preferably a ($C_1$-$C_6$)-alkyl, possibly substituted by up to 3 radicals selected from:
    —OH,
    —O-linear ($C_1$-$C_{12}$)-alkyl, preferably a ($C_1$-$C_6$)-alkyl,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl,
      a halogen atom chosen among Br, Cl, I, F, preferably F,
      a possibly salified or esterified carboxy,
      a possibly salified or esterified carboxy ($C_1$-$C_{12}$)-alkyl, preferably a ($C_1$-$C_6$)-alkyl, or
  a linear or branched ($C_1$-$C_{12}$)-acyl, preferably a ($C_1$-$C_6$)-acyl, possibly substituted by up to 3 radicals selected from:
    —OH,
    —O-linear ($C_1$-$C_{12}$)-alkyl, preferably a ($C_1$-$C_6$)-alkyl,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl,
      a halogen atom chosen among Br, Cl, I, F, preferably F,
      a possibly salified or esterified carboxy,
      a possibly salified or esterified carboxy ($C_1$-$C_{12}$)-alkyl, preferably a ($C_1$-$C_6$)-alkyl,
and $R_6$ can be possibly interrupted by up to 3 heteroatoms selected from O, S or N,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
  —OH,
  —O-linear ($C_1$-$C_{12}$)-alkyl, preferably a ($C_1$-$C_6$)-alkyl,
  a halogen atom chosen among Br, Cl, I, F, preferably F,
  a possibly salified or esterified carboxy,
  an oxo group,
  an aromatic or heteroaromatic aryl possibly substituted by:
    —OH,
    —O-linear ($C_1$-$C_{12}$)-alkyl, preferably a ($C_1$-$C_6$)-alkyl,
    a halogen atom chosen among Br, Cl, I, F, preferably F,
    a possibly salified or esterified carboxy,
    a possibly salified or esterified carboxy ($C_1$-$C_{12}$)-alkyl, preferably a ($C_1$-$C_6$)-alkyl,
and the pharmaceutically acceptable salts, enantiomers, diastereoisomers of same, as well as mixture of same, with the proviso that the following compounds are excluded:

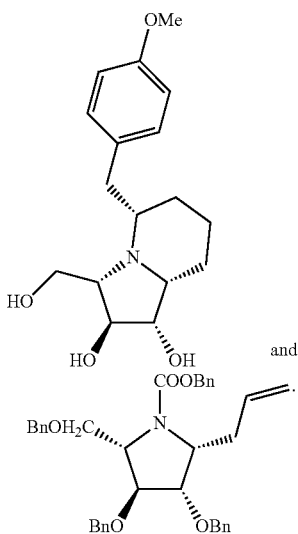
(6)

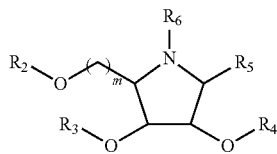

In another embodiment, the present invention relates to compounds of the following formula III:

$$\underset{R_3\diagdown O}{\overset{R_2\diagdown O\diagdown}{\bigcirc}}\overset{R_6}{\underset{N}{\bigcirc}}\overset{R_5}{\underset{O\diagup R_4}{\bigcirc}}$$

wherein:

m represents an integer being equal to 0, 1, 2, $R_2$, $R_3$ and $R_4$ represent independently from each other:
- a hydrogen atom, or
- a linear or branched $(C_1-C_{12})$-alkyl, preferably a $(C_1-C_6)$-alkyl, more preferably a $(C_1-C_3)$-alkyl, or
- a linear or branched $(C_1-C_{12})$-acyl, preferably a $(C_1-C_6)$-acyl, more preferably a $(C_1-C_3)$-acyl, $R_5$ represents:
- a hydrogen atom, or
- a linear or branched $(C_1-C_{13})$-alkyl, preferably a $(C_1-C_6)$-alkyl, more preferably a $(C_1-C_2)$-alkyl, possibly substituted by up to 3 radicals selected from:
  —OH,
  —O-linear $(C_1-C_{12})$-alkyl, preferably a $(C_1-C_6)$-alkyl, possibly substituted by an oxo group,
  a halogen atom F,
  a possibly salified or esterified carboxy,
  an oxo group,
  an aromatic or heteroaromatic aryl possibly substituted by:
    —OH,
    —O-linear $(C_1-C_{12})$-alkyl, preferably a $(C_1-C_6)$-alkyl, more preferably a $(C_1-C_2)$-alkyl,
    a halogen atom F,
    a possibly salified or esterified carboxy, and $R_5$ can be possibly interrupted by up to 2 heteroatoms selected from O or N, $R_6$ represents:
- a hydrogen atom, or
- a linear or branched $(C_1-C_{12})$-alkyl, preferably a $(C_1-C_6)$-alkyl, possibly substituted by up to 3 radicals selected from:
  —OH,
  —O-linear $(C_1-C_{12})$-alkyl, preferably a $(C_1-C_6)$-alkyl,
  a halogen atom F,
  a possibly salified or esterified carboxy,
  an oxo group,
  an aromatic or heteroaromatic aryl possibly substituted by:
    —OH,
    —O-linear $(C_1-C_{12})$-alkyl, preferably a $(C_1-C_6)$-alkyl, more preferably $(C_1-C_2)$-alkyl,
    a halogen atom F,
    a possibly salified or esterified carboxy, or
- a linear or branched $(C_1-C_{12})$-acyl, preferably a $(C_1-C_6)$-acyl, possibly substituted by up to 3 radicals selected from:
  —OH,
  —O-linear $(C_1-C_{12})$-alkyl, preferably a $(C_1-C_6)$-alkyl,
  a halogen atom F,
  a possibly salified or esterified carboxy,
  an oxo group,
  an aromatic or heteroaromatic aryl possibly substituted by:
    —OH,
    —O-linear $(C_1-C_{12})$-alkyl, preferably a $(C_1-C_6)$-alkyl, more preferably $(C_1-C_2)$-alkyl,
    a halogen atom F,
    a possibly salified or esterified carboxy, and $R_6$ can be possibly interrupted by up to 3 heteroatoms selected from O or N, or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O and N and/or terminated by an heteroatom selected from O and N and/or possibly substituted by up to three radicals selected from:
  —OH,
  —O-linear $(C_1-C_{12})$-alkyl, preferably a $(C_1-C_6)$-alkyl, more preferably a $(C_1-C_2)$-alkyl
  a halogen atom F,
  a possibly salified or esterified carboxy,
  an oxo group,
  an aromatic or heteroaromatic aryl possibly substituted by:
    —OH,
    —O-linear $(C_1-C_{12})$-alkyl, preferably a $(C_1-C_6)$-alkyl, more preferably a $(C_1-C_2)$-alkyl
    a halogen atom F,
    a possibly salified or esterified carboxy, and the pharmaceutically acceptable salts, enantiomers, diastereoisomers of same, as well as mixture of same, with the proviso that the following compounds are excluded:

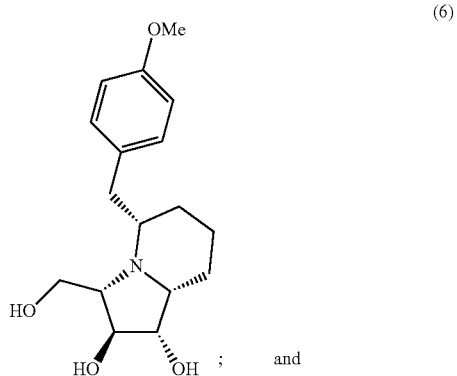
(6)

-continued

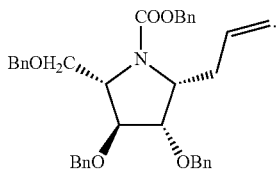

In another embodiment, the present invention relates to compounds of the following formula III:

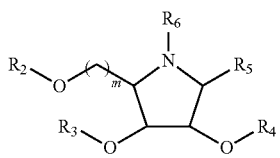

wherein:

m represents an integer being equal to 1, $R_2$, $R_3$ and $R_4$ are as defined previously, $R_5$ represents:

a linear or branched $(C_1-C_{13})$-alkyl, preferably a $(C_1-C_6)$-alkyl, possibly substituted by up to 3 radicals selected from:

—O-linear $(C_1-C_{12})$-alkyl, preferably a $(C_1-C_6)$-alkyl, possibly substituted by an oxo group, a possibly salified or esterified carboxy, an oxo group, an aromatic or heteroaromatic aryl possibly substituted by:

—O-linear $(C_1-C_{12})$-alkyl, preferably a $(C_1-C_6)$-alkyl, and $R_5$ can be possibly interrupted by up to 3 heteroatoms selected from O or N, with the proviso that $R_5$ cannot be a linear $C_4$-alkyl if $R_2$, $R_3$ and $R_4$ are hydrogen atom, $R_6$ represents a hydrogen atom, or or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and substituted by up to three radicals selected from:

a possibly salified or esterified carboxy, an oxo group, an aromatic or heteroaromatic aryl possibly substituted by:

—O-linear $(C_1-C_{12})$-alkyl, preferably a $(C_1-C_6)$-alkyl, and the pharmaceutically acceptable salts, enantiomers, diastereoisomers of same, as well as mixture of same, with the proviso that the following compounds is excluded:

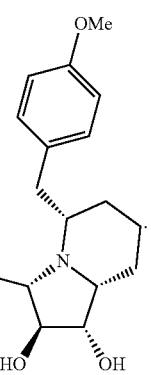

(6)

In a fifth embodiment, the present invention relates to compounds of the following formula IV:

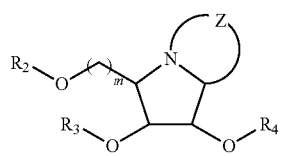

wherein:

m represents an integer being equal to 0, 1, 2, 3, 4, 5 or 6, $R_2$, $R_3$ and $R_4$ represent independently from each other:

a hydrogen atom, or a linear or branched $(C_1-C_{12})$-alkyl, or a linear or branched $(C_1-C_{12})$-acyl, Z represents an alkylene radical having 2 to 5 carbon atoms which is possibly substituted and/or possibly interrupted by up to 3 heteroatoms selected from O, S, N and/or terminated by an heteroatom selected from O, S, N, and the pharmaceutically acceptable salts, enantiomers, diastereoisomers of same, as well as mixture of same, with the proviso that the following compound is excluded:

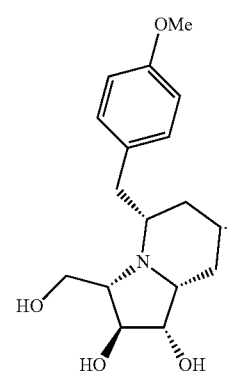

(6)

In another embodiment, the present invention relates to compounds of the following formula IV:

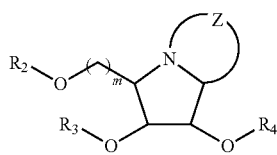

wherein:
m represents an integer being equal to 0, 1, 2, 3, 4, 5 or 6,
$R_2$, $R_3$ and $R_4$ represent independently from each other:
 a hydrogen atom, or
 a linear or branched ($C_1$-$C_{12}$)-alkyl, preferably a ($C_1$-$C_6$)-alkyl, or
 a linear or branched ($C_1$-$C_{12}$)-acyl, preferably a ($C_1$-$C_6$)-acyl,
Z represents an alkylene radical having 2 to 5 carbon atoms which is possibly interrupted by 1 or 2 heteroatoms selected from O, S, N and/or terminated by an heteroatom selected from O, S, N and/or possibly substituted by up to three radicals selected from:
 —OH,
 —O-linear ($C_1$-$C_{12}$)-alkyl, preferably a ($C_1$-$C_6$)-alkyl,
 a halogen atom chosen among Br, Cl, I, F, preferably F,
 a possibly salified or esterified carboxy,
 an oxo group,
 an aromatic or heteroaromatic aryl possibly substituted by:
  —OH,
  —O-linear ($C_1$-$C_{12}$)-alkyl, preferably a ($C_1$-$C_6$)-alkyl,
  a halogen atom chosen among Br, Cl, I, F, preferably F,
  a possibly salified or esterified carboxy,
  a possibly salified or esterified carboxy ($C_1$-$C_{12}$)-alkyl, preferably a ($C_1$-$C_6$)-alkyl,
and the pharmaceutically acceptable salts, enantiomers, diastereoisomers of same, as well as mixture of same,
with the proviso that the following compound is excluded:

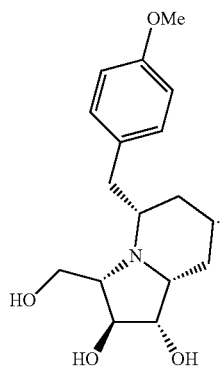

(6)

In another embodiment, the present invention relates to compounds of the following formula IV:

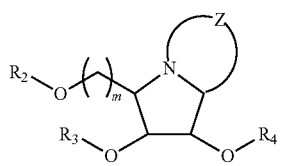

wherein:
m represents an integer being equal to 0, 1, 2,
$R_2$, $R_3$ and $R_4$ represent independently from each other:
 a hydrogen atom, or
 a linear or branched ($C_1$-$C_{12}$)-alkyl, preferably a ($C_1$-$C_6$)-alkyl, more preferably a ($C_1$-$C_3$)-alkyl, or
 a linear or branched ($C_1$-$C_{12}$)-acyl, preferably a ($C_1$-$C_6$)-acyl, more preferably a ($C_1$-$C_3$)-acyl,
Z represents an alkylene radical having 2 to 5 carbon atoms which is possibly interrupted by 1 or 2 heteroatoms selected from O and N and/or terminated by an heteroatom selected from O and N and/or possibly substituted by up to three radicals selected from:
 —OH,
 —O-linear ($C_1$-$C_{12}$)-alkyl, preferably a ($C_1$-$C_6$)-alkyl,
 a halogen atom F,
 a possibly salified or esterified carboxy,
 an oxo group,
 an aromatic or heteroaromatic aryl possibly substituted by:
  —OH,
  —O-linear ($C_1$-$C_{12}$)-alkyl, preferably a ($C_1$-$C_6$)-alkyl, more preferably a ($C_1$-$C_2$)-alkyl
  a halogen atom F,
  a possibly salified or esterified carboxy,
and the pharmaceutically acceptable salts, enantiomers, diastereoisomers of same, as well as mixture of same,
with the proviso that the following compound is excluded:

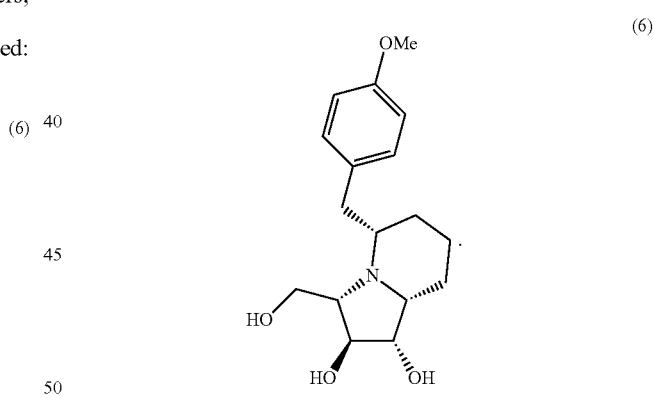

(6)

In another embodiment, the present invention relates to compounds of the following formula VI:

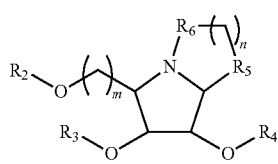

wherein X, m, R2, R3, R4, R5 and R6 are as previously defined, and n being an integer being equal to 1, 2, 3,
and the pharmaceutically acceptable salts, enantiomers, diastereoisomers of same, as well as mixture of same, with the proviso that the following compound is excluded:

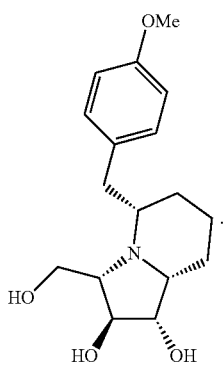
(6)

In another embodiment, the present invention relates to compounds of the following formula VIII:

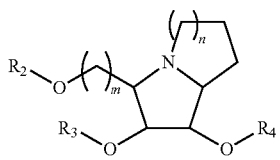

wherein X, m, R2, R3, R4, R5 and R6 are as previously defined, and n being an integer being equal to 1, 2, 3, and the pharmaceutically acceptable salts, enantiomers, diastereoisomers of same, as well as mixture of same, with the proviso that the following compound is excluded:

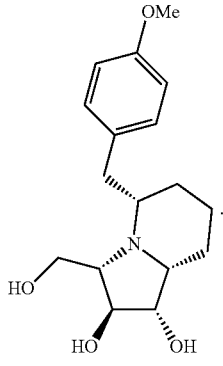
(6)

In another embodiment, the present invention also relates to compounds of the following formula XII:

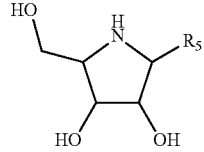

wherein R5 is as previously defined,
and the pharmaceutically acceptable salts, enantiomers, diastereoisomers of same, as well as mixture of same.

In another embodiment, the present invention also relates to compounds of formulas III, IV, VI, VII, VIII or XII, wherein:

m represents an integer being equal to 0 or 1,
X represents a simple bond,
$R_2$, $R_3$ and $R_4$ represent independently from each other:
  a hydrogen atom, or
  a linear or branched ($C_1$-$C_{12}$)-alkyl, preferably a ($C_1$-$C_6$)-alkyl, or
$R_5$ represents:
  a hydrogen atom, or
  a linear or branched ($C_1$-$C_{13}$)-alkyl, preferably a ($C_1$-$C_6$)-alkyl, possibly substituted by up to 3 radicals selected from:
    —OH,
    —O-linear ($C_1$-$C_{12}$)-alkyl, preferably a ($C_1$-$C_6$)-alkyl, possibly substituted by an oxo group,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl,
and $R_5$ can be possibly interrupted by up to 3 heteroatoms selected from O, S or N,
$R_6$ represents a hydrogen atom,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
  a possibly salified or esterified carboxy,
  an oxo group,
  an aromatic or heteroaromatic aryl possibly substituted by
    —O-linear ($C_1$-$C_{12}$)-alkyl, preferably a ($C_1$-$C_6$)-alkyl,
and the pharmaceutically acceptable salts, enantiomers, diastereoisomers of same, as well as mixture of same,
with the proviso that the following compounds are excluded:

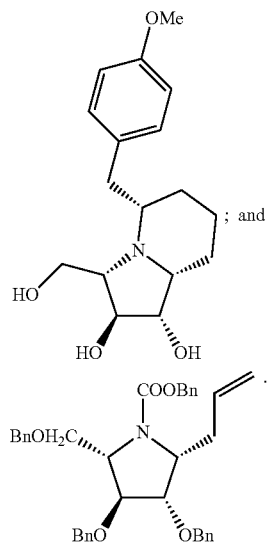
(6)

In another embodiment, the present invention also relates to compounds of formulas III, IV, VI, VIII or XII, wherein:

$R_5$ represents;
  a linear or branched $(C_1-C_{13})$-alkyl, preferably a $(C_1-C_6)$-alkyl, possibly substituted by up to 3 radicals selected from:
    —OH,
    —O-linear $(C_1-C_{12})$-alkyl, preferably a $(C_1-C_6)$-alkyl, possibly substituted by an oxo group,
    a possibly salified or esterified carboxy,
    an oxo group,
    an aromatic or heteroaromatic aryl possibly substituted by:
      —O-linear $(C_1-C_{12})$-alkyl, preferably a $(C_1-C_6)$-alkyl, and $R_5$ can be possibly interrupted by up to 3 heteroatoms selected from O, S or N, notably O and N,
$R_6$ represents a hydrogen atom,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
  a possibly salified or esterified carboxy,
  an oxo group,
  an aromatic or heteroaromatic aryl possibly substituted by:
    O-linear $(C_1-C_{12})$-alkyl, preferably a $(C_1-C_6)$-alkyl.
and the pharmaceutically acceptable salts, enantiomers, diastereoisomers of same, as well as mixture of same.

In another embodiment, the present invention also relates to compounds of formulas III, IV, VI, VIII or XII, wherein:
m represents 1
$R_5$ represents:
  a linear or branched $(C_1-C_{13})$-alkyl, preferably a $(C_1-C_6)$-alkyl, possibly substituted by up to 3 radicals selected from:
    —O-linear $(C_1-C_{12})$-alkyl, preferably a $(C_1-C_6)$-alkyl, possibly substituted by an oxo group,
    a possibly salified or esterified carboxy,
    an oxo group,
    an aromatic or heteroaromatic aryl possibly substituted by:
      —O-linear $(C_1-C_{12})$-alkyl, preferably a $(C_1-C_6)$-alkyl,
and $R_5$ can be possibly interrupted by up to 3 heteroatoms selected from O or N,
with the proviso that $R_5$ cannot be a linear $C_4$-alkyl, if $R_2$, $R_3$ and $R_4$ are hydrogen atom,
$R_6$ represents a hydrogen atom, or
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and substituted by up to three radicals selected from:
  a possibly salified or esterified carboxy,
  an oxo group,
  an aromatic or heteroaromatic aryl possibly substituted by:
    O-linear $(C_1-C_{12})$-alkyl, preferably a $(C_1-C_6)$-alkyl,
and the pharmaceutically acceptable salts, enantiomers, diastereoisomers of same, as well as mixture of same.

In another embodiment, the present invention also relates to compounds of the following formula XII:

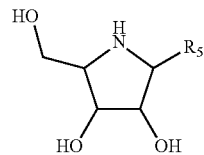

wherein R5 represents:
$R_5$ represents:
  a linear or branched $(C_1-C_{13})$-alkyl, preferably a $(C_1-C_6)$-alkyl, possibly substituted by up to 3 radicals selected from:
    —O-linear $(C_1-C_{12})$-alkyl, preferably a $(C_1-C_6)$-alkyl, possibly substituted by an oxo group,
    a possibly salified or esterified carboxy,
    an oxo group,
    an aromatic or heteroaromatic aryl possibly substituted by:
      —O-linear $(C_1-C_{12})$-alkyl, preferably a $(C_1-C_6)$-alkyl,
and $R_5$ can be possibly interrupted by up to 3 heteroatoms selected from O or N,
with the proviso that $R_5$ cannot be a linear $C_4$-alkyl if $R_2$, $R_3$ and $R_4$ are hydrogen atom,
and the pharmaceutically acceptable salts, enantiomers, diastereoisomers of same, as well as mixture of same.

In another embodiment, the present invention also relates to compounds of formula I, the said compounds corresponding to compounds of the following formula XII:

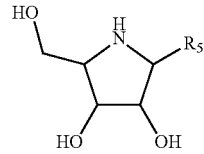

wherein R5 represents:
  a linear or branched $(C_1-C_{13})$-alkyl, preferably a $(C_1-C_6)$-alkyl, possibly substituted by up to 3 radicals selected from:
    a possibly salified or esterified carboxy,
    an aromatic or heteroaromatic aryl possibly substituted by:
      —O-linear $(C_1-C_{12})$ alkyl, preferably a $(C_1-C_6)$-alkyl
and $R_5$ can be possibly interrupted by up to 3 heteroatoms selected from O, S or N, notably N preferably, with the proviso that $R_5$ cannot be a linear $C_4$-alkyl if $R_2$, $R_3$ and $R_4$ are hydrogen atom,
and the pharmaceutically acceptable salts, enantiomers, diastereoisomers of same, as well as mixture of same.

In another embodiment, the present invention also relates to compounds of formula I, the said compounds corresponding to compounds of the following formula IV:

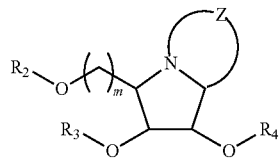

wherein:

m represents 1,

X represents z simple bond, $R_2$, $R_3$ and $R_4$ represent a hydrogen atom, $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N, notably N, and/or terminated by an heteroatom selected from O, S, N and/or possibly substituted by up to three radicals selected from:

a possibly salified or esterified carboxy, an oxo group, an aromatic or heteroaromatic aryl possibly substituted by:

O-linear ($C_1$-$C_{12}$)-alkyl, preferably a ($C_1$-$C_6$)-alkyl, and the pharmaceutically acceptable salts, enantiomers, diastereoisomers of same, as well as mixture of same.

In another embodiment, the present invention relates to compounds having the following formula:

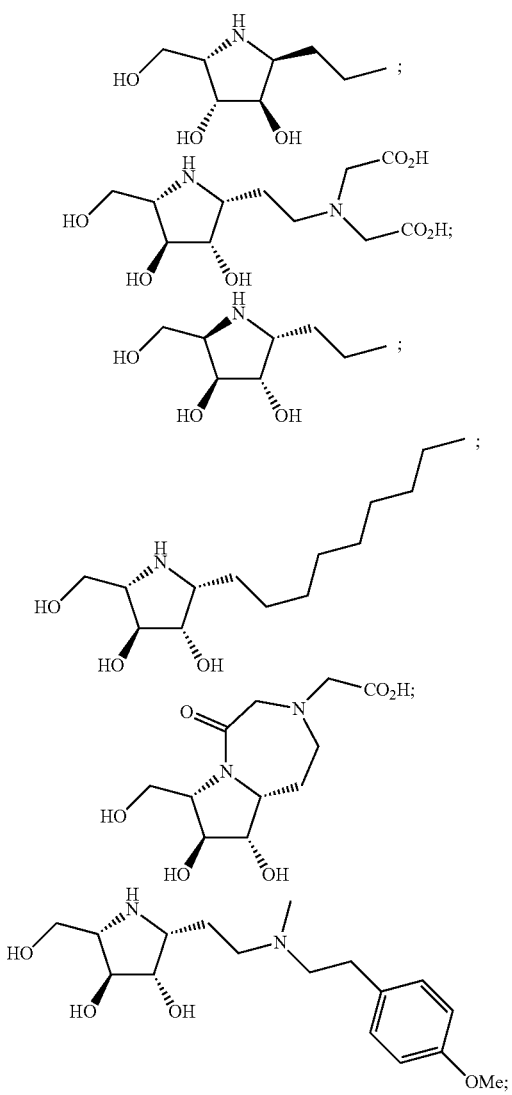

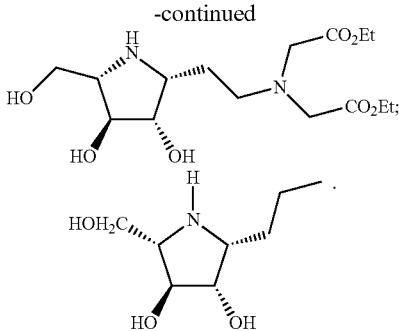

In a sixth embodiment, the present invention relates to a pharmaceutical composition comprising as active ingredient one or more of the compounds of the following formula Ill:

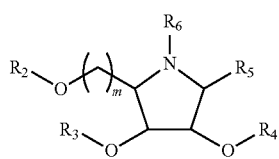

wherein m, R2, R3, R4, R5 and R6 are as defined previously, in combination with excipients and/or pharmaceutically acceptable diluents or carriers.

Any conventional carrier material can be utilized. The carrier material can be an organic or inorganic inert carrier material, for example one that is suitable for oral administration. Suitable carriers include water, gelatin, gum arabic, lactose, starch, magnesium stearate, talc, vegetable oils, polyalkylene-glycols, glycerine and petroleum jelly. Furthermore, the pharmaceutical preparations may also contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional form including a solid form for oral administration such as tablets, capsules, pills, powders, granules, and rectal suppositories. The pharmaceutical preparations may be sterilized and/or may contain adjuvants such as preservatives, stabilizers, wetting agents, emulsifiers, salts for varying the osmotic pressure and/or buffers.

The compounds of the invention can also be administered to a patient in accordance with the invention by topical (including transdermal, buccal or sublingual), or parenteral (including intraperitoneal, subcutaneous, intravenous, intradermal or intramuscular injection) routes.

In another embodiment, the present invention relates to a pharmaceutical composition comprising as active ingredient one or more of the compounds of the following formula IV:

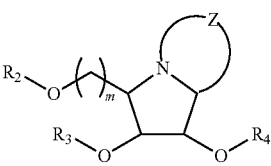

wherein m, R2, R3, R4 and Z are as defined previously, in combination with excipients and/or pharmaceutically acceptable diluents or carriers.

In another embodiment, the present invention relates to a pharmaceutical composition comprising as active ingredient one or more of the compounds of the formula VI, VII or XII as previously defined.

In another embodiment, the present invention relates to a above-mentioned pharmaceutical composition, further comprising an antibiotic selected from the group consisting of aminoglycosides, quinolones, cephalosporins, ureidopenicillines, carbapenems, polymyxins and monobactams.

In another embodiment, the present invention relates to a above-mentioned pharmaceutical composition, further comprising a disinfecting agent selected from the group consisting of antioxidants, phosphates, colouring agents, EDTA, or a combination thereof.

Disinfectants are notably antimicrobial/antibacterial agents that are applied to non-living objects (such as surface, floor, medical device, . . . ) to destroy microorganisms that are living on them.

In another embodiment, the present invention relates to a composition comprising as active ingredient one or more of the compounds of the formula I, II, III, IV, V, VI, VII, VIII, IX, X, XI or XII as previously defined.

In another embodiment, the present invention relates to a composition comprising as active ingredient one or more of the compounds of the formula I, II, III, IV, V, VI, VII, VIII, IX, X, XI or XII as previously defined, and further comprising a disinfecting agent selected from the group consisting of antioxidants, phosphates, colouring agents, EDTA, or a combination thereof.

In another embodiment, the present invention relates to a above-mentioned pharmaceutical composition, comprising one or more of the following compounds:

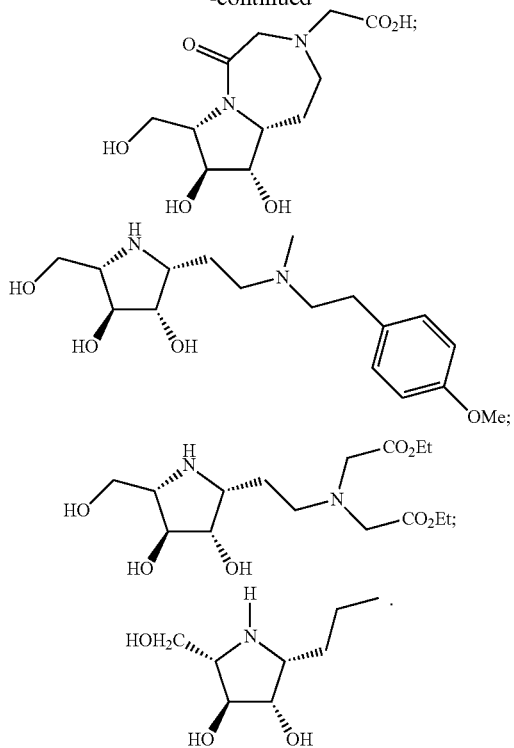

In another embodiment, the present invention relates to a composition, comprising one or more of the following compounds:

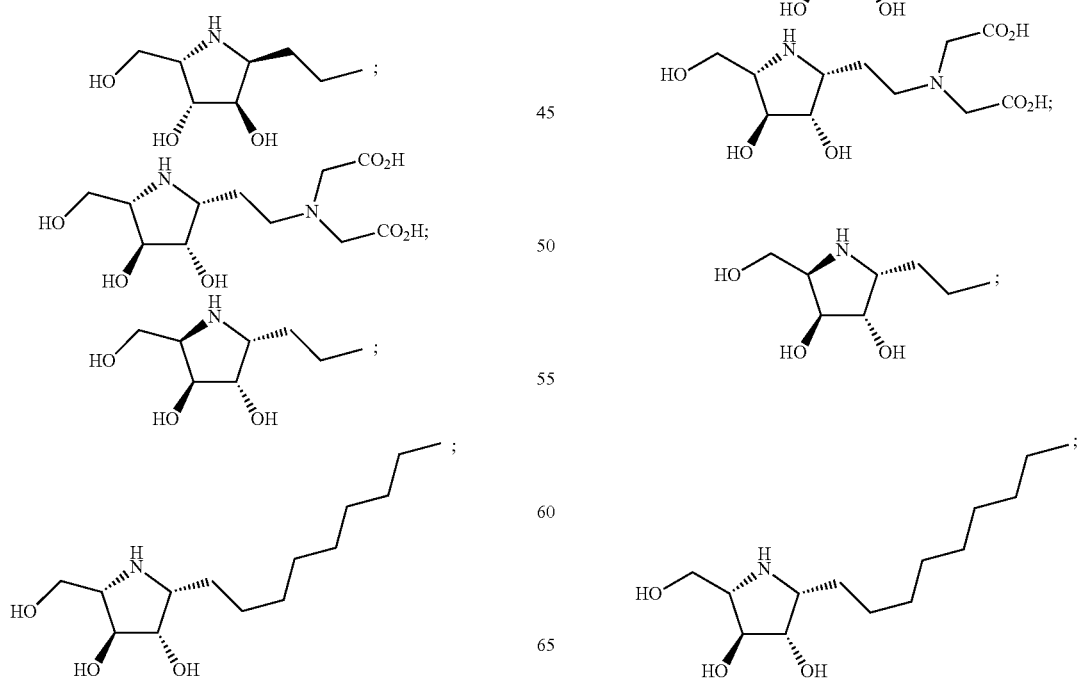

-continued

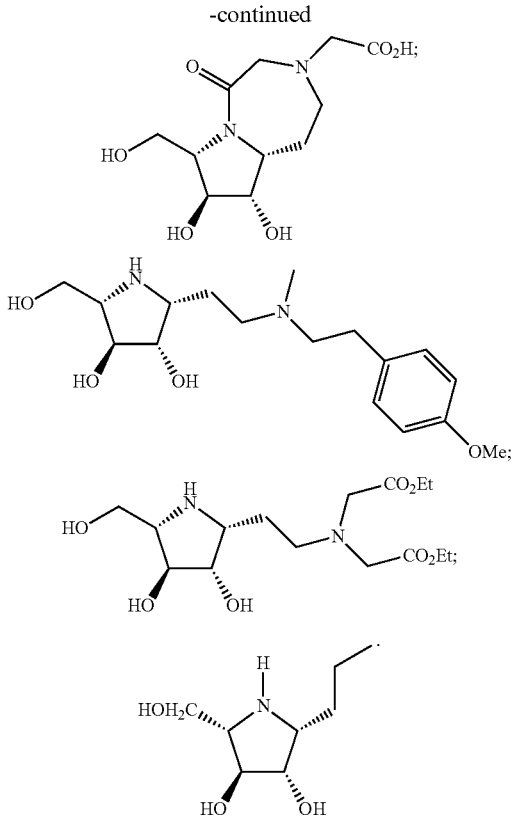

In a seventh embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, in association with one or several antibiotics.

In such compositions, iminosugars can increase the bioavailability of antibiotics, and thus reduce the amount of such antibiotics to be used and to be administered because of increased efficacy against the bacterias. Such compositions comprising at least one iminosugar, in combination with one or several antibiotics are new compositions that can be effective against sensitive and/or resistant bacterias, by lowering the level of resistance of the latter. Iminosugars of the present invention can provide a synergistic effect when used in combination with antibiotics.

In another embodiment, the present invention relates to a composition, notably a pharmaceutical composition, comprising or consisting in as active ingredient one or more of the compounds of the following formula I:

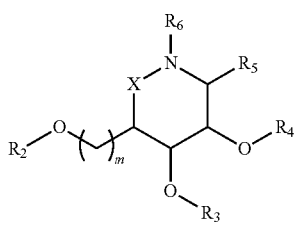

wherein:
m represents an integer being equal to 0, 1, 2, 3, 4, 5 or 6,
X represents a simple bond or a radical —$CHR_1$— wherein $R_1$ represents:
  a hydrogen atom, or
  a linear or branched, possibly interrupted by up to 3 heteroatoms selected from O, S or N and/or possibly substituted, ($C_1$-$C_{12}$)-alkyl,
$R_2$, $R_3$ and $R_4$ represent independently from each other:
  a hydrogen atom, or
  a linear or branched ($C_1$-$C_{12}$)-alkyl, or
  a linear or branched ($C_1$-$C_{12}$)-acyl,
$R_5$ represents:
  a hydrogen atom, or
  a linear or branched, possibly substituted, ($C_1$-$C_{13}$)-alkyl, or
  a linear or branched, possibly substituted ($C_1$-$C_{13}$)-alkyl interrupted by up to 3 heteroatoms selected from O, S or N,
$R_6$ represents:
  a hydrogen atom, or
  a linear or branched possibly substituted ($C_1$-$C_{12}$)-alkyl, or
  a linear or branched possibly substituted ($C_1$-$C_{12}$)-acyl, or
  a linear or branched, possibly substituted ($C_1$-$C_{12}$)-alkyl interrupted by up to 3 heteroatoms selected from O, S or N, or
  a linear or branched, possibly substituted ($C_1$-$C_{12}$)-acyl interrupted by up to 3 heteroatoms selected from O, S or N,
or $R_5$ and $R_6$ represent together with the N atom to which $R_6$ is bound and the carbon atom to which $R_5$ is bound an alkylene radical Z having 2 to 5 carbon atoms which is possibly substituted and/or possibly interrupted by up to 3 heteroatoms selected from O, S, N and/or terminated by an heteroatom selected from O, S, N,
and the pharmaceutically acceptable salts, enantiomers, diastereoisomers of same, as well as mixture of same,
and further comprising at least one antibiotic.

In another embodiment, the present invention relates to a composition, notably a pharmaceutical composition, comprising or consisting in as active ingredient one or more of the compounds of the following formula I:

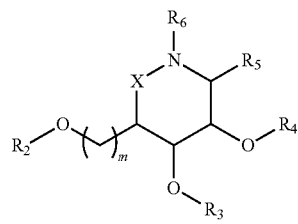

wherein:
m represents an integer being equal to 0, 1, 2, 3, 4, 5 or 6,
X represents a simple bond or a radical —$CHR_1$— wherein $R_1$ represents:
  a hydrogen atom, or
  a linear or branched ($C_1$-$C_{12}$)-alkyl, preferably a ($C_1$-$C_6$)-alkyl, possibly interrupted by up to 3 heteroatoms selected from O, S or N and/or possibly substituted by up to 3 radicals selected from:
    —OH,
    —O-linear ($C_1$-$C_{12}$)-alkyl, preferably a ($C_1$-$C_6$)-alkyl,
    —O-linear ($C_1$-$C_{12}$)-acyl, preferably a ($C_1$-$C_6$)-acyl, a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
—O-linear ($C_1$-$C_{12}$)-acyl, preferably a ($C_1$-$C_6$)-acyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, $R_2$, $R_3$ and $R_4$ represent independently from each other:
a hydrogen atom, or
a linear or branched ($C_1$-$C_{12}$)-alkyl, preferably a ($C_1$-$C_6$)-alkyl, or
a linear or branched ($C_1$-$C_{12}$)-acyl, preferably a ($C_1$-$C_6$)-acyl, $R_5$ represents:
a hydrogen atom, or
a linear or branched ($C_1$-$C_{13}$)-alkyl, preferably a ($C_1$-$C_6$)-alkyl, possibly substituted by up to 3 radicals selected from:
—OH,
—O-linear ($C_1$-$C_{12}$)-alkyl, preferably a ($C_1$-$C_6$)-alkyl, possibly substituted by an oxo group,
a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, and $R_5$ can be possibly interrupted by up to 3 heteroatoms selected from O, S or N, $R_6$ represents:
a hydrogen atom, or
a linear or branched ($C_1$-$C_{12}$)-alkyl, preferably a ($C_1$-$C_6$)-alkyl, possibly substituted by up to 3 radicals selected from:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, or
a linear or branched ($C_1$-$C_{12}$)-acyl, preferably a ($C_1$-$C_6$)-acyl, possibly substituted by up to 3 radicals selected from:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, and $R_6$ can be possibly interrupted by up to 3 heteroatoms selected from O, S or N, or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, and the pharmaceutically acceptable salts, enantiomers, diastereoisomers of same, as well as mixture of same,
and further comprising at least one antibiotic.

In another embodiment, the present invention relates to a composition, notably a pharmaceutical composition, comprising or consisting in as active ingredient one or more of the compounds of the following formula I:

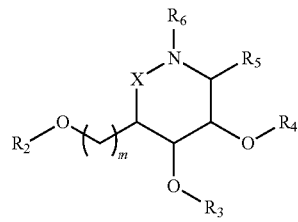

wherein:
m represents an integer being equal to 0, 1, 2,
X represents a simple bond or a radical —$CHR_1$— wherein
$R_1$ represents:
a hydrogen atom, or
a linear or branched ($C_1$-$C_{12}$)-alkyl, preferably a ($C_1$-$C_6$)-alkyl, possibly interrupted by up to 3 heteroatoms selected from O and/or possibly substituted by up to 3 radicals selected from:
—OH,
—O-linear ($C_1$-$C_{12}$)-alkyl, preferably a ($C_1$-$C_6$)-alkyl,
—O-linear ($C_1$-$C_{12}$)-acyl, preferably a ($C_1$-$C_6$)-acyl, a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably a $(C_1-C_2)$-alkyl,
a halogen atom F,
a possibly salified or esterified carboxy, $R_2$, $R_3$ and $R_4$ represent independently from each other:
a hydrogen atom, or
a linear or branched $(C_1-C_{12})$-alkyl, preferably a $(C_1-C_6)$-alkyl, more preferably a $(C_1-C_3)$-alkyl, or
a linear or branched $(C_1-C_{12})$-acyl, preferably a $(C_1-C_6)$-acyl, more preferably a $(C_1-C_3)$-acyl, $R_5$ represents:
a hydrogen atom, or
a linear or branched $(C_1-C_{13})$-alkyl, preferably a $(C_1-C_6)$-alkyl, possibly substituted by up to 3 radicals selected from:
—OH,
—O-linear $(C_1-C_{12})$-alkyl, preferably a $(C_1-C_6)$-alkyl, possibly substituted by an oxo group,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably a $(C_1-C_2)$-alkyl,
a halogen atom F,
a possibly salified or esterified carboxy,
and $R_5$ can be possibly interrupted by up to 2 heteroatoms selected from O or N, $R_6$ represents:
a hydrogen atom, or
a linear or branched $(C_1-C_{12})$-alkyl, preferably a $(C_1-C_6)$-alkyl, possibly substituted by up to 3 radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably $(C_1-C_2)$-alkyl,
a halogen atom F,
a possibly salified or esterified carboxy, or
a linear or branched $(C_1-C_{12})$-acyl, preferably a $(C_1-C_6)$-acyl, possibly substituted by up to 3 radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably $(C_1-C_2)$-alkyl,
a halogen atom F,
a possibly salified or esterified carboxy,
and $R_6$ can be possibly interrupted by up to 3 heteroatoms selected from O or N,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O and N and/or terminated by an heteroatom selected from O and N and/or possibly substituted by up to three radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably a $(C_1-C_2)$-alkyl,
a halogen atom F,
a possibly salified or esterified carboxy,
and the pharmaceutically acceptable salts, enantiomers, diastereoisomers of same, as well as mixture of same,
and further comprising at least one antibiotic.

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, and further comprising at least one antibiotic selected from the group comprising or consisting of aminoglycosides, quinolones, cephalosporins, ureidopenicillines, carbapenems, polymyxins and monobactams.

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, and further comprising at least one antibiotic selected from the group comprising or consisting of Amikacin, Ciprofloxacin, Gentamicin, Piperacilin, Tobramycin, and Ceftazidime.

In another embodiment, the present invention relates to the above-mentioned compositions comprising or consisting in one or more of the following compounds:

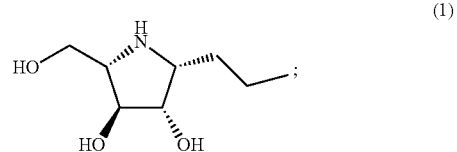
(1)

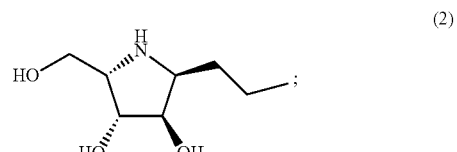
(2)

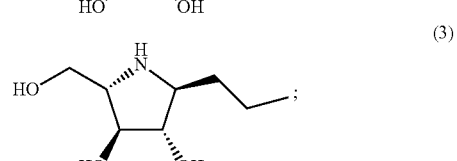
(3)

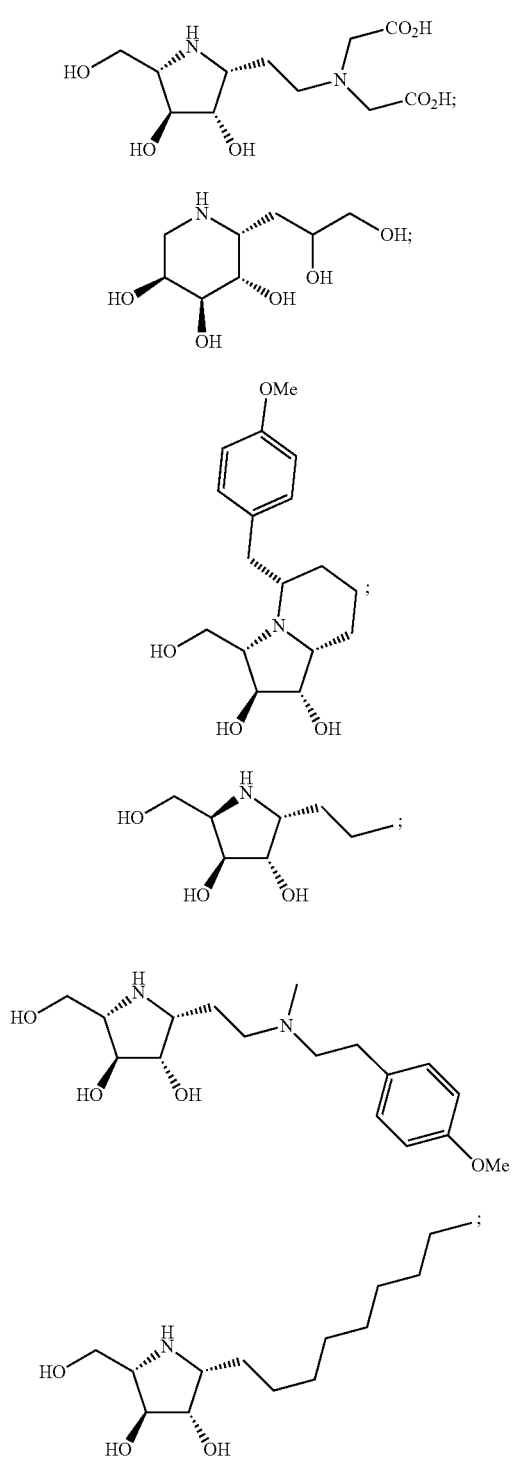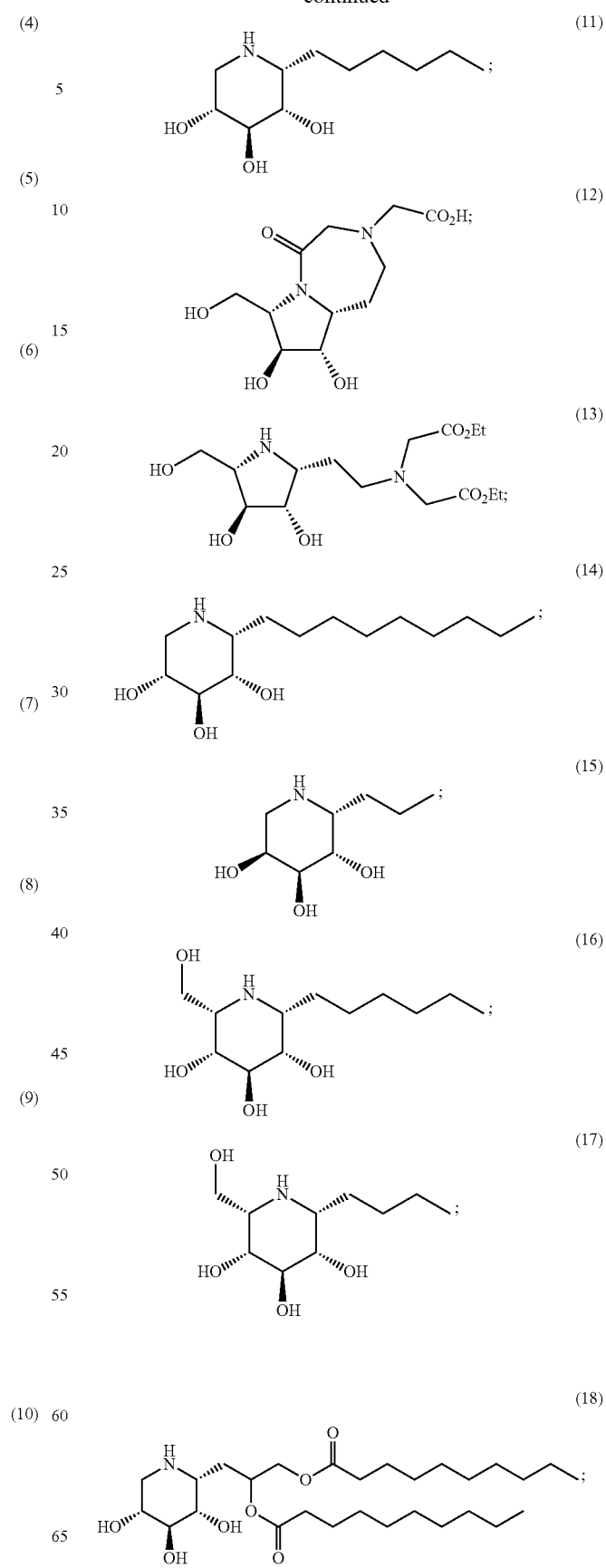

-continued

(19) 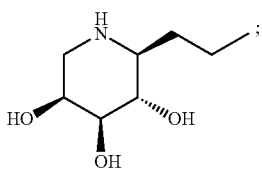

(20) 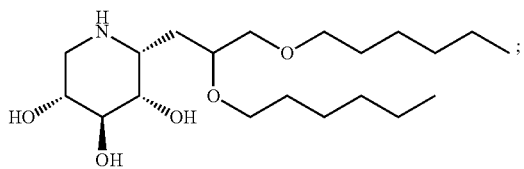

(21) 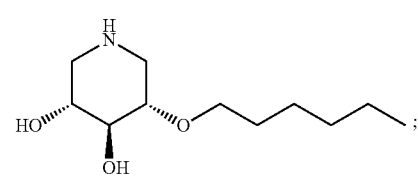

(22) 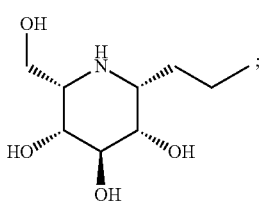

(23) 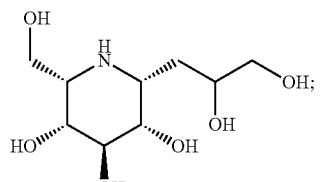

(24)

and the pharmaceutically acceptable salts, enantiomers, diastereoisomers of same, as well as mixture of same,
in association with one or several antibiotics, notably at least one antibiotic selected from the group comprising or consisting of aminoglycosides, quinolones, cephalosporins, ureidopenicillines, carbapenems, polymyxins and monobactams, more particularly selected from the group comprising or consisting of Amikacin, Ciprofloxacin, Gentamicin, Piperacilin, Tobramycin, and Ceftazidime.

In a preferred embodiment, the present invention relates to the above-mentioned compositions comprising or consisting in at least one compound chosen among:

1 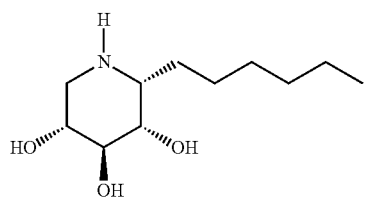

2 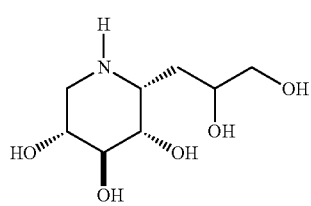

3 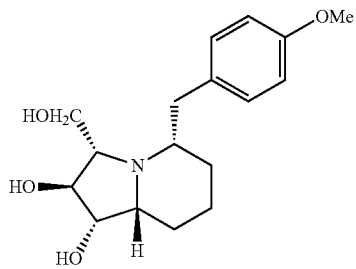

4 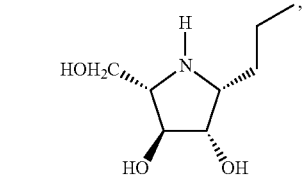

and at least one antibiotic chosen among: Amikacin, Ciprofloxacin, Gentamicin, Piperacilin, Tobramycin, and Ceftazidime.

In another embodiment, the present invention relates to a composition comprising or consisting in as active ingredient one or more of the compounds of the formula I, II, III, IV, V, VI, VII, VIII, IX, X, XI or XII as previously defined, in association with one or several disinfecting agent.

In such compositions, iminosugars can increase the efficacity of disinfecting agents and thus reduce the amount of such disinfecting agents to be used. Such compositions comprising at least one iminosugar, in combination with one or several disinfecting agents are new compositions that can be effective against sensitive and/or resistant bacterias, by lowering the level of resistance of the latter. Iminosugars of the present invention can provide a synergistic effect when used in combination with disinfecting agents.

In another embodiment, the present invention relates to a composition, notably a pharmaceutical composition, comprising or consisting in as active ingredient one or more of the compounds of the following formula I:

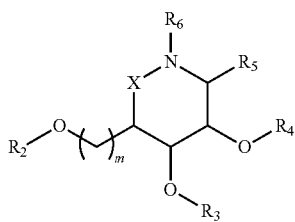

wherein:
m represents an integer being equal to 0, 1, 2, 3, 4, 5 or 6,
X represents a simple bond or a radical —CHR$_1$— wherein R$_1$ represents:
  a hydrogen atom, or
  a linear or branched, possibly interrupted by up to 3 heteroatoms selected from O, S or N and/or possibly substituted, (C$_1$-C$_{12}$)-alkyl,
R$_2$, R$_3$ and R$_4$ represent independently from each other:
  a hydrogen atom, or
  a linear or branched (C$_1$-C$_{12}$)-alkyl, or
  a linear or branched (C$_1$-C$_{12}$)-acyl,
R$_5$ represents:
  a hydrogen atom, or
  a linear or branched, possibly substituted, (C$_1$-C$_{13}$)-alkyl, or
  a linear or branched, possibly substituted (C$_1$-C$_{13}$)-alkyl interrupted by up to 3 heteroatoms selected from O, S or N,
R$_6$ represents:
  a hydrogen atom, or
  a linear or branched possibly substituted (C$_1$-C$_{12}$)-alkyl, or
  a linear or branched possibly substituted (C$_1$-C$_{12}$)-acyl, or
  a linear or branched, possibly substituted (C$_1$-C$_{12}$)-alkyl interrupted by up to 3 heteroatoms selected from O, S or N, or
  a linear or branched, possibly substituted (C$_1$-C$_{12}$)-acyl interrupted by up to 3 heteroatoms selected from O, S or N,
or R$_5$ and R$_6$ represent together with the N atom to which R$_6$ is bound and the carbon atom to which R$_5$ is bound an alkylene radical Z having 2 to 5 carbon atoms which is possibly substituted and/or possibly interrupted by up to 3 heteroatoms selected from O, S, N and/or terminated by an heteroatom selected from O, S, N,
and the pharmaceutically acceptable salts, enantiomers, diastereoisomers of same, as well as mixture of same, and further comprising at least one disinfecting agent.

In another embodiment, the present invention relates to a composition, notably a pharmaceutical composition, comprising or consisting in as active ingredient one or more of the compounds of the following formula I:

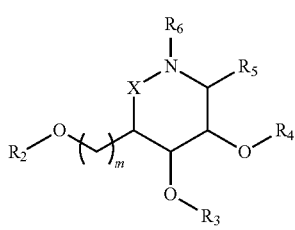

wherein:
m represents an integer being equal to 0, 1, 2, 3, 4, 5 or 6,
X represents a simple bond or a radical —CHR$_1$— wherein R$_1$ represents:
  a hydrogen atom, or
  a linear or branched (C$_1$-C$_{12}$)-alkyl, preferably a (C$_1$-C$_6$)-alkyl, possibly interrupted by up to 3 heteroatoms selected from O, S or N and/or possibly substituted by up to 3 radicals selected from:
    —OH,
    —O-linear (C$_1$-C$_{12}$)-alkyl, preferably a (C$_1$-C$_6$)-alkyl,
    —O-linear (C$_1$-C$_{12}$)-acyl, preferably a (C$_1$-C$_6$)-acyl,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear (C$_1$-C$_{12}$)-alkyl, preferably a (C$_1$-C$_6$)-alkyl,
      —O-linear (C$_1$-C$_{12}$)-acyl, preferably a (C$_1$-C$_6$)-acyl,
      a halogen atom chosen among Br, Cl, I, F, preferably F,
      a possibly salified or esterified carboxy,
      a possibly salified or esterified carboxy (C$_1$-C$_{12}$)-alkyl, preferably a (C$_1$-C$_6$)-alkyl,
R$_2$, R$_3$ and R$_4$ represent independently from each other:
  a hydrogen atom, or
  a linear or branched (C$_1$-C$_{12}$)-alkyl, preferably a (C$_1$-C$_6$)-alkyl, or
  a linear or branched (C$_1$-C$_{12}$)-acyl, preferably a (C$_1$-C$_6$)-acyl,
R$_5$ represents:
  a hydrogen atom, or
  a linear or branched (C$_1$-C$_{13}$)-alkyl, preferably a (C$_1$-C$_6$)-alkyl, possibly substituted by up to 3 radicals selected from:
    —OH,
    —O-linear (C$_1$-C$_{12}$)-alkyl, preferably a (C$_1$-C$_6$)-alkyl, possibly substituted by an oxo group,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear (C$_1$-C$_{12}$)-alkyl, preferably a (C$_1$-C$_6$)-alkyl,
      a halogen atom chosen among Br, Cl, I, F, preferably F,
      a possibly salified or esterified carboxy,
      a possibly salified or esterified carboxy (C$_1$-C$_{12}$)-alkyl, preferably a (C$_1$-C$_6$)-alkyl,
and R$_5$ can be possibly interrupted by up to 3 heteroatoms selected from O, S or N,
R$_6$ represents:
  a hydrogen atom, or
  a linear or branched (C$_1$-C$_{12}$)-alkyl, preferably a (C$_1$-C$_6$)-alkyl, possibly substituted by up to 3 radicals selected from:
    —OH,
    —O-linear (C$_1$-C$_{12}$)-alkyl, preferably a (C$_1$-C$_6$)-alkyl,
    a halogen atom chosen among Br, Cl, I, F, preferably F,
    a possibly salified or esterified carboxy,
    an oxo group,
    an aromatic or heteroaromatic aryl possibly substituted by:

—OH,
—O-linear $(C_1-C_{12})$-alkyl, preferably a $(C_1-C_6)$-alkyl,
a halogen atom chosen among Br, Cl, I, F, preferably F,
a possibly salified or esterified carboxy,
a possibly salified or esterified carboxy $(C_1-C_{12})$-alkyl, preferably a $(C_1-C_6)$-alkyl, or
a linear or branched $(C_1-C_{12})$-acyl, preferably a $(C_1-C_6)$-acyl, possibly substituted by up to 3 radicals selected from:
—OH,
—O-linear $(C_1-C_{12})$-alkyl, preferably a $(C_1-C_6)$-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl,
a halogen atom chosen among Br, Cl, I, F, preferably F,
a possibly salified or esterified carboxy,
a possibly salified or esterified carboxy $(C_1-C_{12})$-alkyl, preferably a $(C_1-C_6)$-alkyl, and $R_6$ can be possibly interrupted by up to 3 heteroatoms selected from O, S or N,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
—OH,
—O-linear $(C_1-C_{12})$-alkyl, preferably a $(C_1-C_6)$-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl,
a halogen atom chosen among Br, Cl, I, F, preferably F,
a possibly salified or esterified carboxy,
a possibly salified or esterified carboxy $(C_1-C_{12})$-alkyl, preferably a $(C_1-C_6)$-alkyl, and the pharmaceutically acceptable salts, enantiomers, diastereoisomers of same, as well as mixture of same
and further comprising at least one disinfecting agent.

In another embodiment, the present invention relates to a composition, notably a pharmaceutical composition, comprising or consisting in as active ingredient one or more of the compounds of the following formula I:

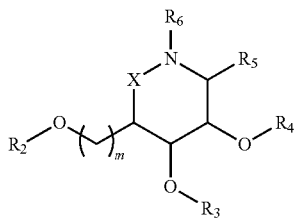

wherein:
m represents an integer being equal to 0, 1, 2,
X represents a simple bond or a radical —$CHR_1$— wherein $R_1$ represents:
a hydrogen atom, or
a linear or branched $(C_1-C_{12})$-alkyl, preferably a $(C_1-C_6)$-alkyl, possibly interrupted by up to 3 heteroatoms selected from O and/or possibly substituted by up to 3 radicals selected from:
—OH,
—O-linear $(C_1-C_{12})$-alkyl, preferably a $(C_1-C_6)$-alkyl,
—O-linear $(C_1-C_{12})$-acyl, preferably a $(C_1-C_6)$-acyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably a $(C_1-C_2)$-alkyl,
a halogen atom F,
a possibly salified or esterified carboxy,
$R_2$, $R_3$ and $R_4$ represent independently from each other:
a hydrogen atom, or
a linear or branched $(C_1-C_{12})$-alkyl, preferably a $(C_1-C_6)$-alkyl, more preferably a $(C_1-C_3)$-alkyl, or
a linear or branched $(C_1-C_{12})$-acyl, preferably a $(C_1-C_6)$-acyl, more preferably a $(C_1-C_3)$-acyl,
$R_5$ represents:
a hydrogen atom, or
a linear or branched $(C_1-C_{13})$-alkyl, preferably a $(C_1-C_6)$-alkyl, possibly substituted by up to 3 radicals selected from:
—OH,
—O-linear $(C_1-C_{12})$-alkyl, preferably a $(C_1-C_6)$-alkyl, possibly substituted by an oxo group,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably a $(C_1-C_2)$-alkyl,
a halogen atom F,
a possibly salified or esterified carboxy,
and $R_5$ can be possibly interrupted by up to 2 heteroatoms selected from O or N,
$R_6$ represents:
a hydrogen atom, or
a linear or branched $(C_1-C_{12})$-alkyl, preferably a $(C_1-C_6)$-alkyl, possibly substituted by up to 3 radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably $(C_1-C_2)$-alkyl,
a halogen atom F,
a possibly salified or esterified carboxy, or a linear or branched ($C_1$-$C_{12}$)-acyl, preferably a ($C_1$-$C_6$)-acyl, possibly substituted by up to 3 radicals selected from:
—OH,
—O-linear ($C_1$-$C_{12}$)-alkyl, preferably a ($C_1$-$C_6$)-alkyl,
a halogen atom F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl, more preferably ($C_1$-$C_2$)-alkyl,
a halogen atom F,
a possibly salified or esterified carboxy,
and $R_6$ can be possibly interrupted by up to 3 heteroatoms selected from O or N,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O and N and/or terminated by an heteroatom selected from O and N and/or possibly substituted by up to three radicals selected from:
—OH,
—O-linear ($C_1$-$C_{12}$)-alkyl, preferably a ($C_1$-$C_6$)-alkyl,
a halogen atom F,
a possibly salified or esterified carboxy,
an OXO group,
an aromatic or heteroaromatic aryl possibly substituted by:
—OH,
—O-linear ($C_1$-$C_{12}$)-alkyl, preferably a ($C_1$-$C_6$)-alkyl, more preferably a ($C_1$-$C_2$)-alkyl,
a halogen atom F,
a possibly salified or esterified carboxy,
and the pharmaceutically acceptable salts, enantiomers, diastereoisomers of same, as well as mixture of same, and further comprising at least one disinfecting agent.

In another embodiment, the present invention relates to a composition comprising or consisting in as active ingredient one or more of the compounds of the formula I, II, III, IV, V, VI, VII, VIII, IX, X, XI or XII as previously defined, and further comprising a disinfecting agent selected from the group consisting of antioxidants, phosphates, colouring agents, EDTA, or a combination thereof.

In another embodiment, the present invention relates to the above-mentioned compositions comprising or consisting in one or more of the following compounds:

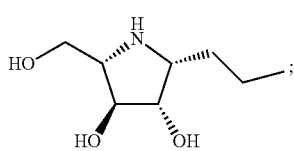
(1)

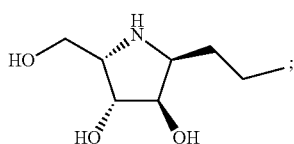
(2)

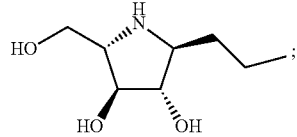
(3)

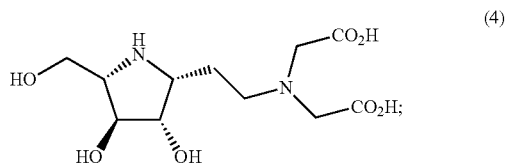
(4)

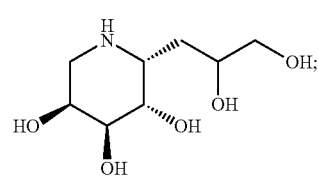
(5)

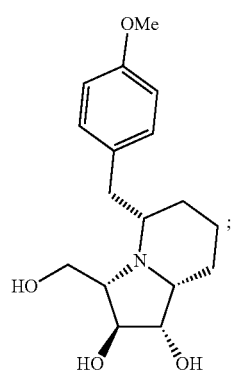
(6)

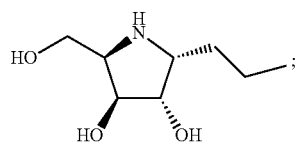
(7)

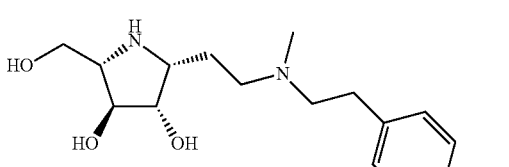
(8)

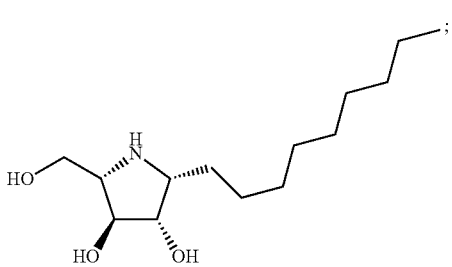
(9)

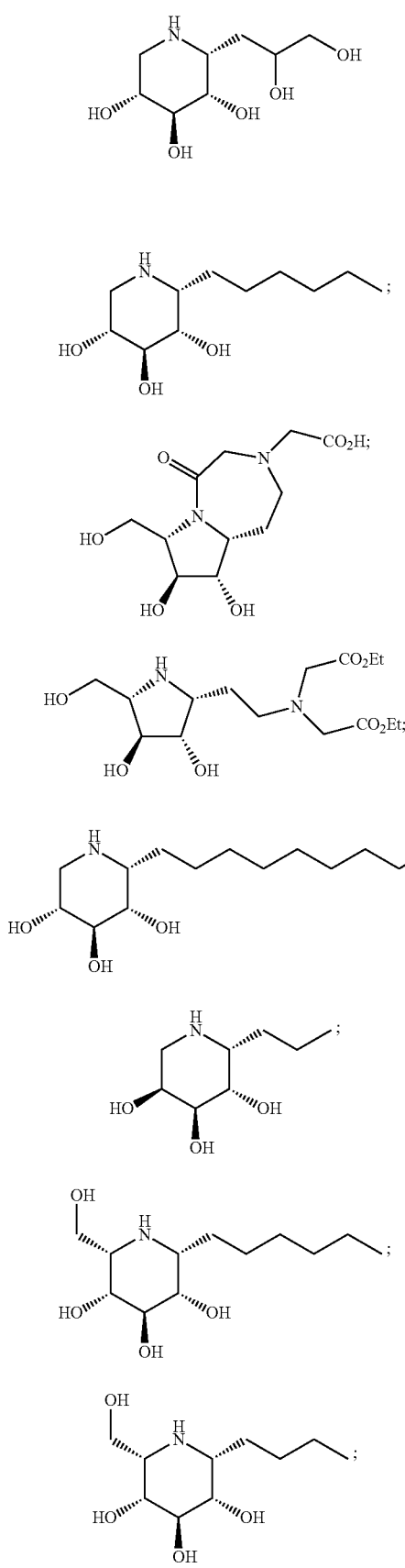
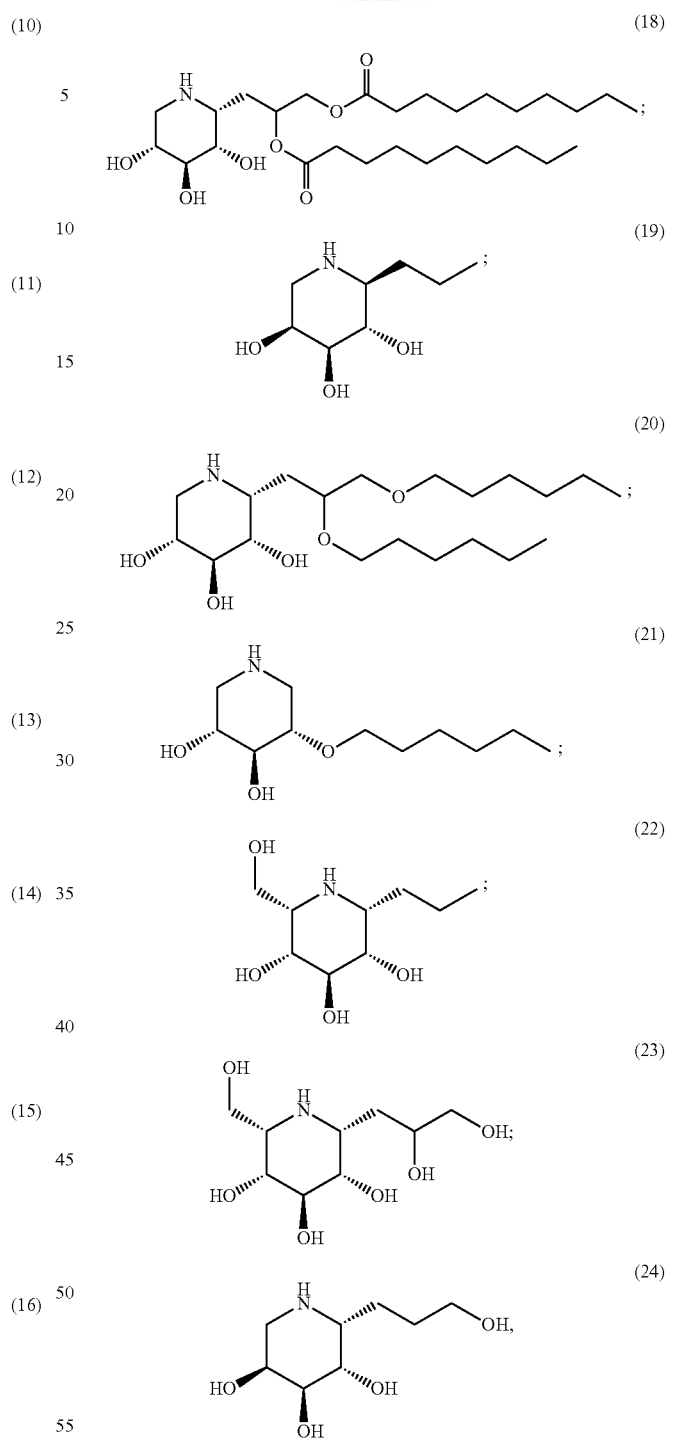

and the pharmaceutically acceptable salts, enantiomers, diastereoisomers of same, as well as mixture of same, in association with one or several disinfecting agent, notably selected from the group consisting of antioxidants, phosphates, colouring agents, EDTA, or a combination thereof.

In another embodiment, the present invention also relates to the above-mentioned compositions comprising or consisting in as active ingredient the compounds of formula I, II, III, IV, V, VI, VII, VIII, IX, X, XI or XII, wherein:

$R_5$ represents:
    a linear or branched $(C_1-C_{13})$-alkyl, preferably a $(C_1-C_6)$-alkyl, possibly substituted by up to 3 radicals selected from:
        —OH,
        —O-linear $(C_1-C_{12})$-alkyl, preferably a $(C_1-C_6)$-alkyl, possibly substituted by an oxo group,
        a possibly salified or esterified carboxy,
        an oxo group,
        an aromatic or heteroaromatic aryl possibly substituted by:
            —O-linear $(C_1-C_{12})$-alkyl, preferably a $(C_1-C_6)$-alkyl,
and $R_5$ can be possibly interrupted by up to 3 heteroatoms selected from O, S or N, notably O and N,
$R_6$ represents a hydrogen atom, or
or $R_5$ and $R_6$ represent together with the N atom to which 1% is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
    a possibly salified or esterified carboxy,
    an oxo group,
    an aromatic or heteroaromatic aryl possibly substituted by:
        O-linear $(C_1-C_{12})$-alkyl, preferably a $(C_1-C_6)$-alkyl,
and the pharmaceutically acceptable salts, enantiomers, diastereoisomers of same, as well as mixture of same.

In another embodiment, the present invention also relates to the above-mentioned compositions comprising or consisting in as active ingredient the compounds of formula I, II, III, IV, V, VI, VII, VIII, IX, X, XI or XII, wherein:
$R_5$ represents:
    a linear or branched $(C_1-C_{13})$-alkyl, preferably a $(C_1-C_6)$-alkyl, possibly substituted by up to 3 radicals selected from:
        —O-linear $(C_1-C_{12})$-alkyl, preferably a $(C_1-C_6)$-alkyl, possibly substituted by an oxo group,
        a possibly salified or esterified carboxy,
        an oxo group,
        an aromatic or heteroaromatic aryl possibly substituted by:
            —O-linear $(C_1-C_{12})$-alkyl, preferably a $(C_1-C_6)$-alkyl,
and $R_5$ can be possibly interrupted by up to 3 heteroatoms selected from O or N, notably with the proviso that $R_5$ cannot be linear $C_4$-alkyl if $R_2$, $R_3$ and $R_4$ are hydrogen atom, more particularly if m represents 1,
$R_6$ represents a hydrogen atom, or
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and substituted by up to three radicals selected from:
    a possibly salified or esterified carboxy,
    an oxo group,
    an aromatic or heteroaromatic aryl possibly substituted by:
        O-linear $(C_1-C_{12})$-alkyl, preferably a $(C_1-C_6)$-alkyl.
and the pharmaceutically acceptable salts, enantiomers, diastereoisomers of same, as well as mixture of same.

In another embodiment, the present invention also relates to the above-mentioned compositions comprising or consisting in as active ingredient the compounds of formula I, II, III, IV, V, VI, VII, VIII, IX, X, XI or XII, notably XII, wherein:
R5 represents:
    a linear or branched $(C_1-C_{13})$-alkyl, preferably a $(C_1-C_6)$-alkyl, possibly substituted by up to 3 radicals selected from:
        a possibly salified or esterified carboxy,
        an aromatic or heteroaromatic aryl possibly substituted by:
            —O-linear $(C_1-C_{12})$ alkyl, preferably a $(C_1-C_6)$-alkyl
and $R_5$ can be possibly interrupted by up to 3 heteroatoms selected from O, S or N, notably N notably, with the proviso that $R_5$ cannot be a linear $C_4$-alkyl if $R_2$, $R_3$ and $R_4$ are hydrogen atom, more particularly if $R_6$ is a hydrogen atom, and the pharmaceutically acceptable salts, enantiomers, diastereoisomers of same, as well as mixture of same.

In another embodiment, the present invention also relates to the above-mentioned compositions comprising or consisting in as active ingredient the compounds of formula I, II, III, IV, V, VI, VII, VIII, IX, X, XI or XII, notably IV, wherein:
$R_2$, $R_3$ and $R_4$ represent a hydrogen atom,
$R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N, notably N, and/or terminated by an heteroatom selected from O, S, N and/or possibly substituted by up to three radicals selected from:
    a possibly salified or esterified carboxy,
    an oxo group,
    an aromatic or heteroaromatic aryl possibly substituted by:
        O-linear $(C_1-C_{12})$-alkyl, preferably a $(C_1-C_6)$-alkyl,
and the pharmaceutically acceptable salts, enantiomers, diastereoisomers of same, as well as mixture of same.

In another embodiment, the present invention also relates to the above-mentioned compositions comprising or consisting in as active ingredient the compounds of formula I, II, III, IV, V, VI, VII, VIII, IX, X, XI or XII, notably XI, wherein:
$R_5$ represents:
    a linear or branched $(C_1-C_{13})$-alkyl, preferably a $(C_1-C_6)$-alkyl, possibly substituted by up to 3 radicals selected from:
        —OH,
        —O-linear $(C_1-C_{12})$-alkyl, preferably a $(C_1-C_6)$-alkyl, possibly substituted by an oxo group,
        an oxo group,
and the pharmaceutically acceptable salts, enantiomers, diastereoisomers of same, as well as mixture of same.

All the above-mentioned compositions can also contain excipients and/or acceptable diluents or carriers.

The above-mentioned compositions can be made up in any conventional form including a solid form for oral administration such as tablets, capsules, pills, powders, granules, and rectal suppositories. The compositions may be sterilized and/or may contain adjuvants such as preservatives, stabilizers, wetting agents, emulsifiers, salts for varying the osmotic pressure and/or buffers.

The compounds and the compositions of the invention can also be administered to a patient in accordance with the invention by topical (including transdermal, buccal or sublingual), or parenteral (including intraperitoneal, subcutaneous, intravenous, intradermal or intramuscular injection) routes.

In a eighth embodiment, the present invention relates to a composition, notably a pharmaceutical composition, comprising to the above-mentioned compositions comprising or consisting in as active ingredient the compounds of formula as active ingredient one or more of the compounds of the formula I, II, III, IV, V, VI, VII, VIII, IX, X, XI or XII as previously defined for their use as antibacterial drugs for the treatment and/or the prevention of infection(s) caused by biofilm-forming bacteria.

In another embodiment, the present invention relates to a composition, notably a pharmaceutical composition, comprising to the above-mentioned compositions comprising or consisting in as active ingredient the compounds of formula as active ingredient one or more of the compounds of the following formula I:

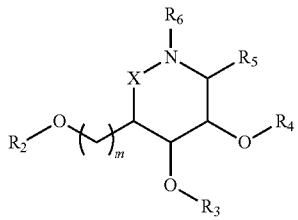

wherein:
m represents an integer being equal to 0, 1, 2, 3, 4, 5 or 6,
X represents a simple bond or a radical —CHR$_1$— wherein R$_1$ represents:
  a hydrogen atom, or
  a linear or branched, possibly interrupted by up to 3 heteroatoms selected from O, S or N and/or possibly substituted, (C$_1$-C$_{12}$)-alkyl,
R$_2$, R$_3$ and R$_4$ represent independently from each other:
  a hydrogen atom, or
  a linear or branched (C$_1$-C$_{12}$)-alkyl, or
  a linear or branched (C$_1$-C$_{12}$)-acyl,
R$_5$ represents:
  a hydrogen atom, or
  a linear or branched, possibly substituted, (C$_1$-C$_{13}$)-alkyl, or
  a linear or branched, possibly substituted (C$_1$-C$_{13}$)-alkyl interrupted by up to 3 heteroatoms selected from O, S or N,
R$_6$ represents:
  a hydrogen atom, or
  a linear or branched possibly substituted (C$_1$-C$_{12}$)-alkyl, or
  a linear or branched possibly substituted (C$_1$-C$_{12}$)-acyl, or
  a linear or branched, possibly substituted (C$_1$-C$_{12}$)-alkyl interrupted by up to 3 heteroatoms selected from O, S or N, or
  a linear or branched, possibly substituted (C$_1$-C$_{12}$)-acyl interrupted by up to 3 heteroatoms selected from O, S or N,
or R$_5$ and R$_6$ represent together with the N atom to which R$_6$ is bound and the carbon atom to which R$_5$ is bound an alkylene radical Z having 2 to 5 carbon atoms which is possibly substituted and/or possibly interrupted by up to 3 heteroatoms selected from O, S, N and/or terminated by an heteroatom selected from O, S, N, and the pharmaceutically acceptable salts, enantiomers, diastereoisomers of same, as well as mixture of same,
and further comprising at least one antibiotic,
for their use as antibacterial drugs for the treatment and/or the prevention of infection(s) caused by biofilm-forming bacteria.

In another embodiment, the present invention relates to a composition, notably a pharmaceutical composition, comprising or consisting in as active ingredient the compounds of formula as active ingredient one or more of the compounds of the following formula I:

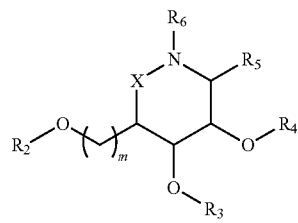

wherein:
m represents an integer being equal to 0, 1, 2, 3, 4, 5 or 6,
X represents a simple bond or a radical —CHR$_1$— wherein R$_1$ represents:
  a hydrogen atom, or
  a linear or branched (C$_1$-C$_{12}$)-alkyl, preferably a (C$_1$-C$_6$)-alkyl, possibly interrupted by up to 3 heteroatoms selected from O, S or N and/or possibly substituted by up to 3 radicals selected from:
    —OH,
    —O-linear (C$_1$-C$_{12}$)-alkyl, preferably a (C$_1$-C$_6$)-alkyl,
    —O-linear (C$_1$-C$_{12}$)-acyl, preferably a (C$_1$-C$_6$)-acyl,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear (C$_1$-C$_{12}$)-alkyl, preferably a (C$_1$-C$_6$)-alkyl,
      —O-linear (C$_1$-C$_{12}$)-acyl, preferably a (C$_1$-C$_6$)-acyl,
      a halogen atom chosen among Br, Cl, I, F, preferably F,
      a possibly salified or esterified carboxy,
      a possibly salified or esterified carboxy (C$_1$-C$_{12}$)-alkyl, preferably a (C$_1$-C$_6$)-alkyl,
R$_2$, R$_3$ and R$_4$ represent independently from each other:
  a hydrogen atom, or
  a linear or branched (C$_1$-C$_{12}$)-alkyl, preferably a (C$_1$-C$_6$)-alkyl, or
  a linear or branched (C$_1$-C$_{12}$)-acyl, preferably a (C$_1$-C$_6$)-acyl,
R$_5$ represents:
  a hydrogen atom, or
  a linear or branched (C$_1$-C$_{13}$)-alkyl, preferably a (C$_1$-C$_6$)-alkyl, possibly substituted by up to 3 radicals selected from:
    —OH,
    —O-linear (C$_1$-C$_{12}$)-alkyl, preferably a (C$_1$-C$_6$)-alkyl, possibly substituted by an oxo group,
    a halogen atom chosen among Br, Cl, I, F, preferably F,
    a possibly salified or esterified carboxy,
    an oxo group, an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, and $R_5$ can be possibly interrupted by up to 3 heteroatoms selected from O, S or N, $R_6$ represents:
a hydrogen atom, or
a linear or branched ($C_1$-$C_{12}$)-alkyl, preferably a ($C_1$-$C_6$)-alkyl, possibly substituted by up to 3 radicals selected from:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, or
a linear or branched ($C_1$-$C_{12}$)-acyl, preferably a ($C_1$-$C_6$)-acyl, possibly substituted by up to 3 radicals selected from:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, and $R_6$ can be possibly interrupted by up to 3 heteroatoms selected from O, S or N, or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, and the pharmaceutically acceptable salts, enantiomers, diastereoisomers of same, as well as mixture of same and further comprising at least one antibiotic, for their use as antibacterial drugs for the treatment and/or the prevention of infection(s) caused by biofilm-forming bacteria.

In another embodiment, the present invention relates to a composition, notably a pharmaceutical composition, comprising or consisting in as active ingredient one or more of the compounds of the following formula I:

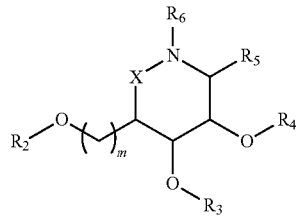

wherein:
m represents an integer being equal to 0, 1, 2,
X represents a simple bond or a radical —$CHR_1$— wherein $R_1$ represents:
a hydrogen atom, or
a linear or branched ($C_1$-$C_{12}$)-alkyl, preferably a ($C_1$-$C_6$)-alkyl, possibly interrupted by up to 3 heteroatoms selected from O and/or possibly substituted by up to 3 radicals selected from:
—OH,
—O-linear ($C_1$-$C_{12}$)-alkyl, preferably a ($C_1$-$C_6$)-alkyl,
—O-linear ($C_1$-$C_{12}$)-acyl, preferably a ($C_1$-$C_6$)-acyl,
a halogen atom F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl, more preferably a ($C_1$-$C_2$)-alkyl,
a halogen atom F,
a possibly salified or esterified carboxy, $R_2$, $R_3$ and $R_4$ represent independently from each other:
a hydrogen atom, or
a linear or branched ($C_1$-$C_{12}$)-alkyl, preferably a ($C_1$-$C_6$)-alkyl, more preferably a ($C_1$-$C_3$)-alkyl, or
a linear or branched ($C_1$-$C_{12}$)-acyl, preferably a ($C_1$-$C_6$)-acyl, more preferably a ($C_1$-$C_3$)-acyl, $R_5$ represents:
a hydrogen atom, or
a linear or branched ($C_1$-$C_{13}$)-alkyl, preferably a ($C_1$-$C_6$)-alkyl, possibly substituted by up to 3 radicals selected from:
—OH,
—O-linear ($C_1$-$C_{12}$)-alkyl, preferably a ($C_1$-$C_6$)-alkyl, possibly substituted by an oxo group,
a halogen atom F,
a possibly salified or esterified carboxy,
an oxo group, an aromatic or heteroaromatic aryl possibly substituted by:
—OH,
—O-linear $(C_1-C_{12})$-alkyl, preferably a $(C_1-C_6)$-alkyl, more preferably a $(C_1-C_2)$-alkyl,
a halogen atom F,
a possibly salified or esterified carboxy,
and $R_5$ can be possibly interrupted by up to 2 heteroatoms selected from O or N,
$R_6$ represents:
a hydrogen atom, or
a linear or branched $(C_1-C_{12})$-alkyl, preferably a $(C_1-C_6)$-alkyl, possibly substituted by up to 3 radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably $(C_1-C_2)$-alkyl,
a halogen atom F,
a possibly salified or esterified carboxy, or
a linear or branched $(C_1-C_{12})$-acyl, preferably a $(C_1-C_6)$-acyl, possibly substituted by up to 3 radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably $(C_1-C_2)$-alkyl,
a halogen atom F,
a possibly salified or esterified carboxy,
and $R_6$ can be possibly interrupted by up to 3 heteroatoms selected from O or N,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O and N and/or terminated by an heteroatom selected from O and N and/or possibly substituted by up to three radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably a $(C_1-C_2)$-alkyl,
a halogen atom F,
a possibly salified or esterified carboxy,
and the pharmaceutically acceptable salts, enantiomers, diastereoisomers of same, as well as mixture of same, and further comprising at least one antibiotic,
for their use as antibacterial drugs for the treatment and/or the prevention of infection(s) caused by biofilm-forming bacteria.

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, in association with one or several antibiotics, for their use as antibacterial drugs for the treatment and/or the prevention of infection(s) caused by biofilm-forming bacteria.

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, and further comprising at least one antibiotic selected from the group comprising or consisting of aminoglycosides, quinolones, cephalosporins, ureidopenicillines, carbapenems, polymyxins and monobactams,
for their use as antibacterial drugs for the treatment and/or the prevention of infection(s) caused by biofilm-forming bacteria.

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, and further comprising at least one antibiotic selected from the group comprising or consisting of Amikacin, Ciprofloxacin, Gentamicin, Piperacilin, Tobramycin, and Ceftazidime,
for their use as antibacterial drugs for the treatment and/or the prevention of infection(s) caused by biofilm-forming bacteria.

In another embodiment, the present invention relates to the above-mentioned compositions comprising or consisting in one or more of the following compounds:

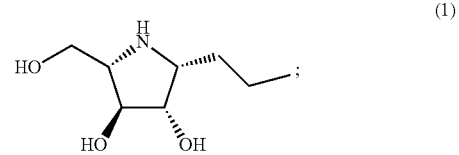

(1)

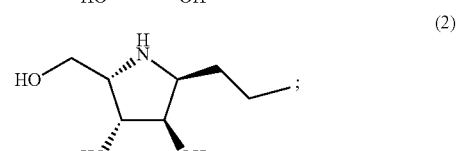

(2)

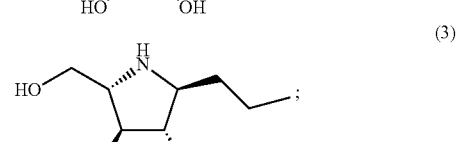

(3)

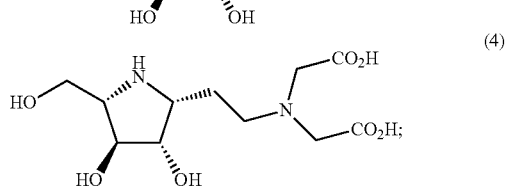

(4)

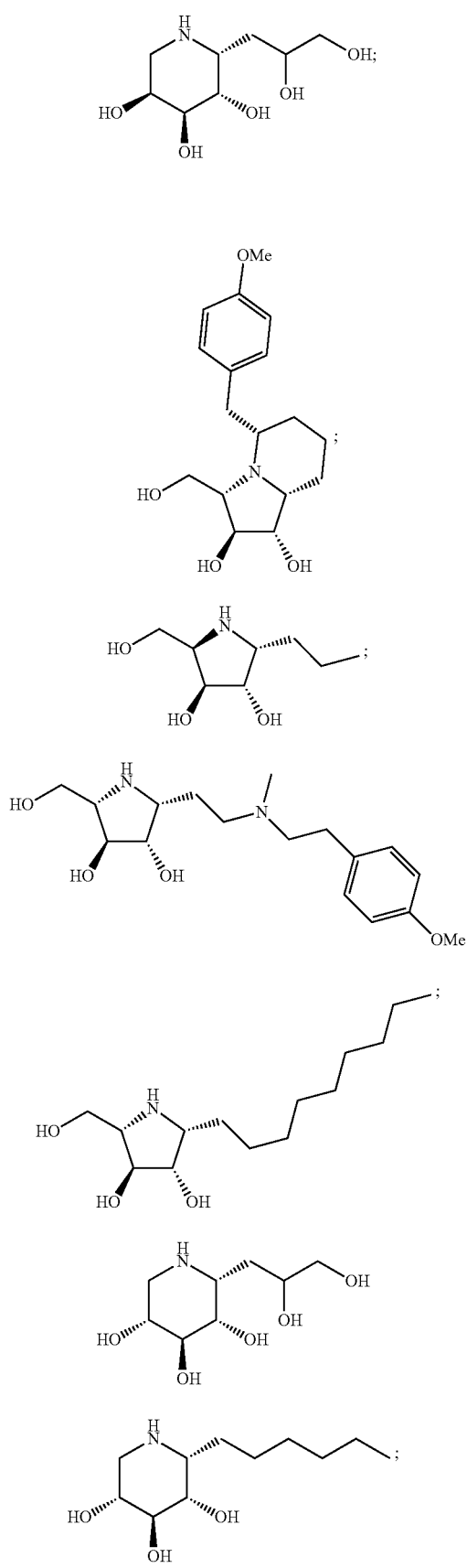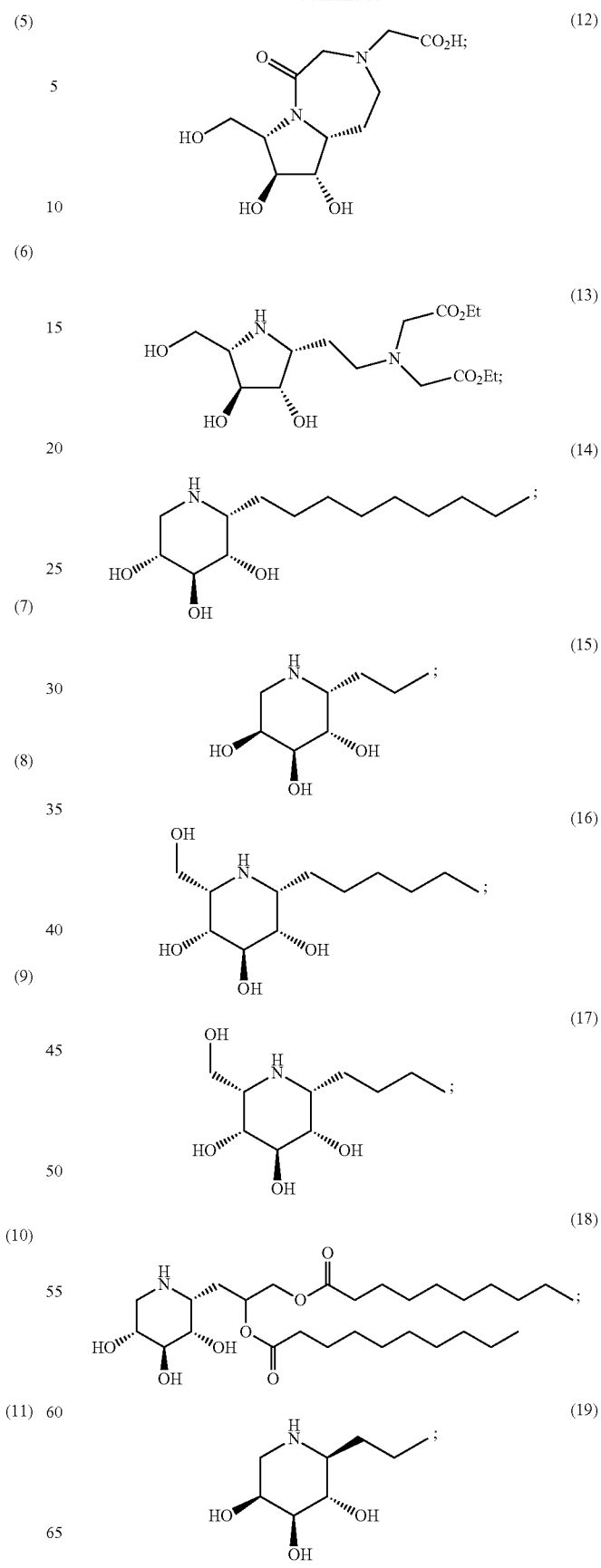

-continued

(20) 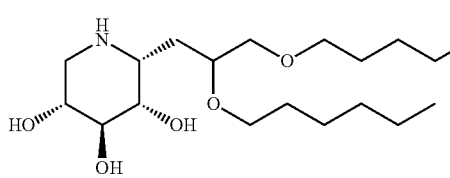

(21) 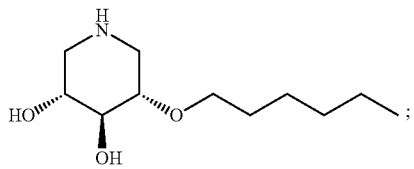

(22) 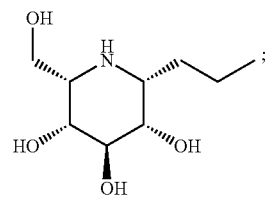

(23) 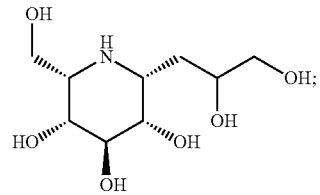

(24) 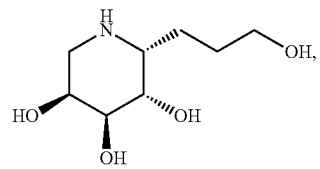

and the pharmaceutically acceptable salts, enantiomers, diastereoisomers of same, as well as mixture of same,
in association with one or several antibiotics, notably at least one antibiotic selected from the group comprising or consisting of aminoglycosides, quinolones, cephalosporins, ureidopenicillines, carbapenems, polymyxins and monobactams, more particularly selected from the group comprising or consisting of Amikacin, Ciprofloxacin, Gentamicin, Piperacilin, Tobramycin, and Ceftazidime,
for their use as antibacterial drugs for the treatment and/or the prevention of infection(s) caused by biofilm-forming bacteria.

In a preferred embodiment, the present invention relates to the above-mentioned compositions comprising or consisting in at least one compound chosen among:

1 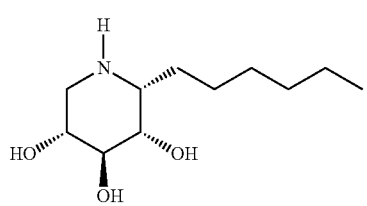

-continued

2 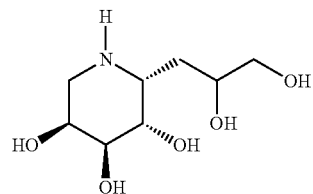

3 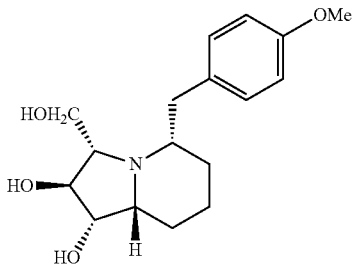

4 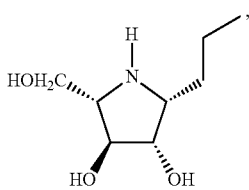

and at least one antibiotic chosen among: Amikacin, Ciprofloxacin, Gentamicin, Piperacilin, Tobramycin, and Ceftazidime,
for their use as antibacterial drugs for the treatment and/or the prevention of infection(s) caused by biofilm-forming bacteria.

The expression "for their use as antibacterial drugs for the treatment and/or the prevention of infection(s) caused by biofilm-forming bacteria" can also mean "for their use for the treatment and/or the prevention of biofilm formation by bacteria, notably bacteria of the genus *Pseudomonas*, preferably *Pseudomonas aeruginosa*".

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, for their use for the treatment and/or the prevention of biofilm formation.

The expression "for their use for the treatment and/or the prevention of biofilm formation" means also "for their use for the treatment and/or the prevention of infections involving biofilm formation by bacteria, notably bacteria of the genus *Pseudomonas*, preferably *Pseudomonas aeruginosa*".

The expression "for their use for the treatment and/or the prevention of biofilm formation" means also "for their use for the treatment and/or the prevention of infections caused by biofilm formation by bacteria, notably bacteria of the genus *Pseudomonas*, preferably *Pseudomonas aeruginosa*".

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, as antibacterial.

In another embodiment, the present invention relates to a composition, notably a pharmaceutical composition, comprising or consisting in as active ingredient one or more of the compounds of the following formula I:

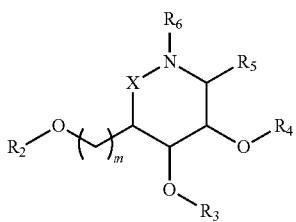

wherein:
m represents an integer being equal to 0, 1, 2, 3, 4, 5 or 6,
X represents a simple bond or a radical —CHR$_1$— wherein R$_1$ represents:
  a hydrogen atom, or
  a linear or branched, possibly interrupted by up to 3 heteroatoms selected from O, S or N and/or possibly substituted, (C$_1$-C$_{12}$)-alkyl,
R$_2$, R$_3$ and R$_4$ represent independently from each other:
  a hydrogen atom, or
  a linear or branched (C$_1$-C$_{12}$)-alkyl, or
  a linear or branched (C$_1$-C$_{12}$)-acyl,
R$_5$ represents:
  a hydrogen atom, or
  a linear or branched, possibly substituted, (C$_1$-C$_{13}$)-alkyl, or
  a linear or branched, possibly substituted (C$_1$-C$_{13}$)-alkyl interrupted by up to 3 heteroatoms selected from O, S or N,
R$_6$ represents:
  a hydrogen atom, or
  a linear or branched possibly substituted (C$_1$-C$_{12}$)-alkyl, or
  a linear or branched possibly substituted (C$_1$-C$_{12}$)-acyl, or
  a linear or branched, possibly substituted (C$_1$-C$_{12}$)-alkyl interrupted by up to 3 heteroatoms selected from O, S or N, or
  a linear or branched, possibly substituted (C$_1$-C$_{12}$)-acyl interrupted by up to 3 heteroatoms selected from O, S or N,
or R$_5$ and R$_6$ represent together with the N atom to which R$_6$ is bound and the carbon atom to which R$_5$ is bound an alkylene radical Z having 2 to 5 carbon atoms which is possibly substituted and/or possibly interrupted by up to 3 heteroatoms selected from O, S, N and/or terminated by an heteroatom selected from O, S, N,
and the pharmaceutically acceptable salts, enantiomers, diastereoisomers of same, as well as mixture of same,
and further comprising at least one antibiotic,
for their use for the treatment and/or the prevention of biofilm formation.

In another embodiment, the present invention relates to a composition, notably a pharmaceutical composition, comprising or consisting in as active ingredient one or more of the compounds of the following formula I:

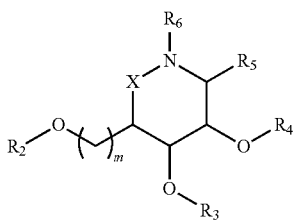

wherein:
m represents an integer being equal to 0, 1, 2, 3, 4, 5 or 6,
X represents a simple bond or a radical —CHR$_1$— wherein R$_1$ represents:
  a hydrogen atom, or
  a linear or branched (C$_1$-C$_{12}$)-alkyl, preferably a (C$_1$-C$_6$)-alkyl, possibly interrupted by up to 3 heteroatoms selected from O, S or N and/or possibly substituted by up to 3 radicals selected from:
    —OH,
    —O-linear (C$_1$-C$_{12}$)-alkyl, preferably a (C$_1$-C$_6$)-alkyl,
    —O-linear (C$_1$-C$_{12}$)-acyl, preferably a (C$_1$-C$_6$)-acyl,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear (C$_1$-C$_{12}$)-alkyl, preferably a (C$_1$-C$_6$)-alkyl,
      —O-linear (C$_1$-C$_{12}$)-acyl, preferably a (C$_1$-C$_6$)-acyl,
      a halogen atom chosen among Br, Cl, I, F, preferably F,
      a possibly salified or esterified carboxy,
      a possibly salified or esterified carboxy (C$_1$-C$_{12}$)-alkyl, preferably a (C$_1$-C$_6$)-alkyl,
R$_2$, R$_3$ and R$_4$ represent independently from each other:
  a hydrogen atom, or
  a linear or branched (C$_1$-C$_{12}$)-alkyl, preferably a (C$_1$-C$_6$)-alkyl, or
  a linear or branched (C$_1$-C$_{12}$)-acyl, preferably a (C$_1$-C$_6$)-acyl,
R$_5$ represents:
  a hydrogen atom, or
  a linear or branched (C$_1$-C$_{13}$)-alkyl, preferably a (C$_1$-C$_6$)-alkyl, possibly substituted by up to 3 radicals selected from:
    —OH,
    —O-linear (C$_1$-C$_{12}$)-alkyl, preferably a (C$_1$-C$_6$)-alkyl, possibly substituted by an oxo group,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear (C$_1$-C$_{12}$)-alkyl, preferably a (C$_1$-C$_6$)-alkyl,
      a halogen atom chosen among Br, Cl, I, F, preferably F,
      a possibly salified or esterified carboxy,
      a possibly salified or esterified carboxy (C$_1$-C$_{12}$)-alkyl, preferably a (C$_1$-C$_6$)-alkyl,
and R$_5$ can be possibly interrupted by up to 3 heteroatoms selected from O, S or N,
R$_6$ represents:
  a hydrogen atom, or
  a linear or branched (C$_1$-C$_{12}$)-alkyl, preferably a (C$_1$-C$_6$)-alkyl, possibly substituted by up to 3 radicals selected from:
    —OH,
    —O-linear (C$_1$-C$_{12}$)-alkyl, preferably a (C$_1$-C$_6$)-alkyl,
    a halogen atom chosen among Br, Cl, I, F, preferably F,
    a possibly salified or esterified carboxy,
    an oxo group,
    an aromatic or heteroaromatic aryl possibly substituted by:

—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
a possibly salified or esterified carboxy ($C_1$-$C_{12}$)-alkyl, preferably a ($C_1$-$C_6$)-alkyl, or
a linear or branched ($C_1$-$C_{12}$)-acyl, preferably a ($C_1$-$C_6$)-acyl, possibly substituted by up to 3 radicals selected from:
—OH,
—O-linear ($C_1$-$C_{12}$)-alkyl, preferably a ($C_1$-$C_6$)-alkyl,
a halogen atom chosen among Br, Cl, I, F, preferably F,
a possibly salified or esterified carboxy,
an oxo group,
an aromatic or heteroaromatic aryl possibly substituted by:
  —OH,
  —O-linear ($C_1$-$C_{12}$)-alkyl, preferably a ($C_1$-$C_6$)-alkyl,
  a halogen atom chosen among Br, Cl, I, F, preferably F,
  a possibly salified or esterified carboxy,
  a possibly salified or esterified carboxy ($C_1$-$C_{12}$)-alkyl, preferably a ($C_1$-$C_6$)-alkyl,
and $R_6$ can be possibly interrupted by up to 3 heteroatoms selected from O, S or N,
or $R_5$ and R % represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
  —OH,
  —O-linear ($C_1$-$C_{12}$)-alkyl, preferably a ($C_1$-$C_6$)-alkyl,
  a halogen atom chosen among Br, Cl, I, F, preferably F,
  a possibly salified or esterified carboxy,
  an oxo group,
  an aromatic or heteroaromatic aryl possibly substituted by:
    —OH,
    —O-linear ($C_1$-$C_{12}$)-alkyl, preferably a ($C_1$-$C_6$)-alkyl,
    a halogen atom chosen among Br, Cl, I, F, preferably F,
    a possibly salified or esterified carboxy,
    a possibly salified or esterified carboxy ($C_1$-$C_{12}$)-alkyl, preferably a ($C_1$-$C_6$)-alkyl,
and the pharmaceutically acceptable salts, enantiomers, diastereoisomers of same, as well as mixture of same
and further comprising at least one antibiotic,
for their use for the treatment and/or the prevention of biofilm formation.

In another embodiment, the present invention relates to a composition, notably a pharmaceutical composition, comprising or consisting in as active ingredient one or more of the compounds of the following formula I:

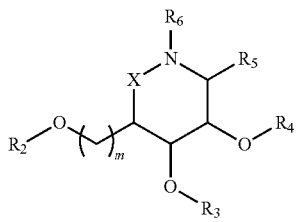

wherein:
m represents an integer being equal to 0, 1, 2,
X represents a simple bond or a radical —$CHR_1$— wherein $R_5$ represents:
  a hydrogen atom, or
  a linear or branched ($C_1$-$C_{12}$)-alkyl, preferably a ($C_1$-$C_6$)-alkyl, possibly interrupted by up to 3 heteroatoms selected from O and/or possibly substituted by up to 3 radicals selected from:
    —OH,
    —O-linear ($C_1$-$C_{12}$)-alkyl, preferably a ($C_1$-$C_6$)-alkyl,
    —O-linear ($C_1$-$C_{12}$)-acyl, preferably a ($C_1$-$C_6$)-acyl,
    a halogen atom F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl, more preferably a ($C_1$-$C_2$)-alkyl,
      a halogen atom F,
      a possibly salified or esterified carboxy,
$R_2$, $R_3$ and $R_4$ represent independently from each other:
  a hydrogen atom, or
  a linear or branched ($C_1$-$C_{12}$)-alkyl, preferably a ($C_1$-$C_6$)-alkyl, more preferably a ($C_1$-$C_3$)-alkyl, or
  a linear or branched ($C_1$-$C_{12}$)-acyl, preferably a ($C_1$-$C_6$)-acyl, more preferably a ($C_1$-$C_3$)-acyl,
$R_5$ represents:
  a hydrogen atom, or
  a linear or branched ($C_1$-$C_{13}$)-alkyl, preferably a ($C_1$-$C_6$)-alkyl, possibly substituted by up to 3 radicals selected from:
    —OH,
    —O-linear ($C_1$-$C_{12}$)-alkyl, preferably a ($C_1$-$C_6$)-alkyl, possibly substituted by an oxo group,
    a halogen atom F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl, more preferably a ($C_1$-$C_2$)-alkyl,
      a halogen atom F,
      a possibly salified or esterified carboxy,
and $R_5$ can be possibly interrupted by up to 2 heteroatoms selected from O or N,
$R_6$ represents:
  a hydrogen atom, or
  a linear or branched ($C_1$-$C_{12}$)-alkyl, preferably a ($C_1$-$C_6$)-alkyl, possibly substituted by up to 3 radicals selected from:
    —OH,
    —O-linear ($C_1$-$C_{12}$)-alkyl, preferably a ($C_1$-$C_6$)-alkyl,
    a halogen atom F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl, more preferably ($C_1$-$C_2$)-alkyl,
      a halogen atom F,
      a possibly salified or esterified carboxy, or a linear or branched ($C_1$-$C_{12}$)-acyl, preferably a ($C_1$-$C_6$)-acyl, possibly substituted by up to 3 radicals selected from:
—OH,
—O-linear ($C_1$-$C_{12}$)-alkyl, preferably a ($C_1$-$C_6$)-alkyl,
a halogen atom F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl, more preferably ($C_1$-$C_2$)-alkyl,
a halogen atom F,
a possibly salified or esterified carboxy,
and $R_6$ can be possibly interrupted by up to 3 heteroatoms selected from O or N,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O and N and/or terminated by an heteroatom selected from O and N and/or possibly substituted by up to three radicals selected from:
—OH,
—O-linear ($C_1$-$C_{12}$)-alkyl, preferably a ($C_1$-$C_6$)-alkyl,
a halogen atom F,
a possibly salified or esterified carboxy,
an oxo group,
an aromatic or heteroaromatic aryl possibly substituted by:
—OH,
—O-linear ($C_1$-$C_{12}$)-alkyl, preferably a ($C_1$-$C_6$)-alkyl, more preferably a ($C_1$-$C_2$)-alkyl,
a halogen atom F,
a possibly salified or esterified carboxy,
and the pharmaceutically acceptable salts, enantiomers, diastereoisomers of same, as well as mixture of same,
and further comprising at least one antibiotic,
for their use for the treatment and/or the prevention of biofilm formation.

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, in association with one or several antibiotics,
for their use for the treatment and/or the prevention of biofilm formation.

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, and further comprising at least one antibiotic selected from the group comprising or consisting of aminoglycosides, quinolones, cephalosporins, ureidopenicillines, carbapenems, polymyxins and monobactams,
for their use for the treatment and/or the prevention of biofilm formation.

In another embodiment, the present invention relates to a composition, notably pharmaceutical composition, comprising or consisting in as active ingredient one or more of the compounds of the formula I, II, III, IV, V, VI, VII, VIII, IX, X, XI or XII as previously defined, and further comprising at least one antibiotic selected from the group comprising or consisting of Amikacin, Ciprofloxacin, Gentamicin, Piperacilin, Tobramycin, and Ceftazidime,
for their use for the treatment and/or the prevention of biofilm formation.

In another embodiment, the present invention relates to a composition, notably a pharmaceutical composition, comprising or consisting in as active ingredient one or more of the compounds of the following formula I:

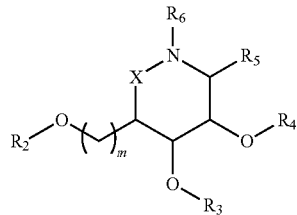

wherein:
m represents an integer being equal to 0, 1, 2, 3, 4, 5 or 6,
X represents a simple bond or a radical —$CHR_1$— wherein $R_1$ represents:
a hydrogen atom, or
a linear or branched, possibly interrupted by up to 3 heteroatoms selected from O, S or N and/or possibly substituted, ($C_1$-$C_{12}$)-alkyl,
$R_2$, $R_3$ and $R_4$ represent independently from each other:
a hydrogen atom, or
a linear or branched ($C_1$-$C_{12}$)-alkyl, or
a linear or branched ($C_1$-$C_{12}$)-acyl,
$R_5$ represents:
a hydrogen atom, or
a linear or branched, possibly substituted, ($C_1$-$C_{13}$)-alkyl, or
a linear or branched, possibly substituted ($C_1$-$C_{13}$)-alkyl interrupted by up to 3 heteroatoms selected from O, S or N,
$R_6$ represents:
a hydrogen atom, or
a linear or branched possibly substituted ($C_1$-$C_{12}$)-alkyl, or
a linear or branched possibly substituted ($C_1$-$C_{12}$)-acyl, or
a linear or branched, possibly substituted ($C_1$-$C_{12}$)-alkyl interrupted by up to 3 heteroatoms selected from O, S or N, or
a linear or branched, possibly substituted ($C_1$-$C_{12}$)-acyl interrupted by up to 3 heteroatoms selected from O, S or N,
or $R_5$ and $R_6$ represent together with the N atom to which $R_6$ is bound and the carbon atom to which $R_5$ is bound an alkylene radical Z having 2 to 5 carbon atoms which is possibly substituted and/or possibly interrupted by up to 3 heteroatoms selected from O, S, N and/or terminated by an heteroatom selected from O, S, N,
and the pharmaceutically acceptable salts, enantiomers, diastereoisomers of same, as well as mixture of same,
and further comprising at least one disinfecting agent,
for their use for the treatment and/or the prevention of biofilm formation.

In another embodiment, the present invention relates to a composition, notably a pharmaceutical composition, comprising or consisting in as active ingredient one or more of the compounds of the following formula I:

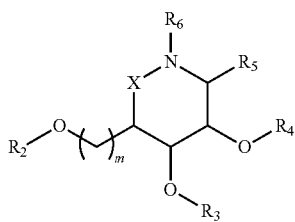

wherein:

m represents an integer being equal to 0, 1, 2, 3, 4, 5 or 6,

X represents a simple bond or a radical —$CHR_1$— wherein $R_1$ represents:
- a hydrogen atom, or
- a linear or branched $(C_1-C_{12})$-alkyl, preferably a $(C_1-C_6)$-alkyl, possibly interrupted by up to 3 heteroatoms selected from O, S or N and/or possibly substituted by up to 3 radicals selected from:
  - —OH,
  - —O-linear $(C_1-C_{12})$-alkyl, preferably a $(C_1-C_6)$-alkyl,
  - —O-linear $(C_1-C_{12})$-acyl, preferably a $(C_1-C_6)$-acyl,
  - a halogen atom chosen among Br, Cl, I, F, preferably F,
  - a possibly salified or esterified carboxy,
  - an oxo group,
  - an aromatic or heteroaromatic aryl possibly substituted by:
    - —OH,
    - —O-linear $(C_1-C_{12})$-alkyl, preferably a $(C_1-C_6)$-alkyl,
    - —O-linear $(C_1-C_{12})$-acyl, preferably a $(C_1-C_6)$-acyl,
    - a halogen atom chosen among Br, Cl, I, F, preferably F,
    - a possibly salified or esterified carboxy,
    - a possibly salified or esterified carboxy $(C_1-C_{12})$-alkyl, preferably a $(C_1-C_6)$-alkyl, $R_2$, $R_3$ and $R_4$ represent independently from each other:
- a hydrogen atom, or
- a linear or branched $(C_1-C_{12})$-alkyl, preferably a $(C_1-C_6)$-alkyl, or
- a linear or branched $(C_1-C_{12})$-acyl, preferably a $(C_1-C_6)$-acyl, $R_5$ represents:
- a hydrogen atom, or
- a linear or branched $(C_1-C_{13})$-alkyl, preferably a $(C_1-C_6)$-alkyl, possibly substituted by up to 3 radicals selected from:
  - —OH,
  - —O-linear $(C_1-C_{12})$-alkyl, preferably a $(C_1-C_6)$-alkyl, possibly substituted by an oxo group,
  - a halogen atom chosen among Br, Cl, I, F, preferably F,
  - a possibly salified or esterified carboxy,
  - an oxo group,
  - an aromatic or heteroaromatic aryl possibly substituted by:
    - —OH,
    - —O-linear $(C_1-C_{12})$-alkyl, preferably a $(C_1-C_6)$-alkyl,
    - a halogen atom chosen among Br, Cl, I, F, preferably F,
    - a possibly salified or esterified carboxy,
    - a possibly salified or esterified carboxy $(C_1-C_{12})$-alkyl, preferably a $(C_1-C_6)$-alkyl, and $R_5$ can be possibly interrupted by up to 3 heteroatoms selected from O, S or N, $R_6$ represents:
- a hydrogen atom, or
- a linear or branched $(C_1-C_{12})$-alkyl, preferably a $(C_1-C_6)$-alkyl, possibly substituted by up to 3 radicals selected from:
  - —OH,
  - —O-linear $(C_1-C_{12})$-alkyl, preferably a $(C_1-C_6)$-alkyl,
  - a halogen atom chosen among Br, Cl, I, F, preferably F,
  - a possibly salified or esterified carboxy,
  - an oxo group,
  - an aromatic or heteroaromatic aryl possibly substituted by:
    - —OH,
    - —O-linear $(C_1-C_{12})$-alkyl, preferably a $(C_1-C_6)$-alkyl,
    - a halogen atom chosen among Br, Cl, I, F, preferably F,
    - a possibly salified or esterified carboxy,
    - a possibly salified or esterified carboxy $(C_1-C_{12})$-alkyl, preferably a $(C_1-C_6)$-alkyl, or
- a linear or branched $(C_1-C_{12})$-acyl, preferably a $(C_1-C_6)$-acyl, possibly substituted by up to 3 radicals selected from:
  - —OH,
  - —O-linear $(C_1-C_{12})$-alkyl, preferably a $(C_1-C_6)$-alkyl,
  - a halogen atom chosen among Br, Cl, I, F, preferably F,
  - a possibly salified or esterified carboxy,
  - an oxo group,
  - an aromatic or heteroaromatic aryl possibly substituted by:
    - —OH,
    - —O-linear $(C_1-C_{12})$-alkyl, preferably a $(C_1-C_6)$-alkyl,
    - a halogen atom chosen among Br, Cl, I, F, preferably F,
    - a possibly salified or esterified carboxy,
    - a possibly salified or esterified carboxy $(C_1-C_{12})$-alkyl, preferably a $(C_1-C_6)$-alkyl, and $R_6$ can be possibly interrupted by up to 3 heteroatoms selected from O, S or N, or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
- —OH,
- —O-linear $(C_1-C_{12})$-alkyl, preferably a $(C_1-C_6)$-alkyl,
- a halogen atom chosen among Br, Cl, I, F, preferably F,
- a possibly salified or esterified carboxy,
- an oxo group,
- an aromatic or heteroaromatic aryl possibly substituted by:
  - —OH,
  - —O-linear $(C_1-C_{12})$-alkyl, preferably a $(C_1-C_6)$-alkyl,
  - a halogen atom chosen among Br, Cl, I, F, preferably F,
  - a possibly salified or esterified carboxy,
  - a possibly salified or esterified carboxy $(C_1-C_{12})$-alkyl, preferably a $(C_1-C_6)$-alkyl, and the pharmaceutically acceptable salts, enantiomers, diastereoisomers of same, as well as mixture of same and further comprising at least one disinfecting agent, for their use for the treatment and/or the prevention of biofilm formation.

In another embodiment, the present invention relates to a composition, notably a pharmaceutical composition, comprising or consisting in as active ingredient one or more of the compounds of the following formula I:

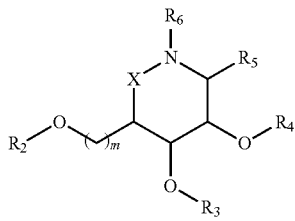

wherein:
m represents an integer being equal to 0, 1, 2,
X represents a simple bond or a radical —CHR$_1$— wherein R$_1$ represents:
 a hydrogen atom, or
 a linear or branched ($C_1$-$C_{12}$)-alkyl, preferably a ($C_1$-$C_6$)-alkyl, possibly interrupted by up to 3 heteroatoms selected from O and/or possibly substituted by up to 3 radicals selected from:
  —OH,
  —O-linear ($C_1$-$C_{12}$)-alkyl, preferably a ($C_1$-$C_6$)-alkyl,
  —O-linear ($C_1$-$C_{12}$)-acyl, preferably a ($C_1$-$C_6$)-acyl,
  a halogen atom F,
  a possibly salified or esterified carboxy,
  an oxo group,
  an aromatic or heteroaromatic aryl possibly substituted by:
   —OH,
   —O-linear ($C_1$-$C_{12}$)-alkyl, preferably a ($C_1$-$C_6$)-alkyl, more preferably a ($C_1$-$C_2$)-alkyl,
   a halogen atom F,
   a possibly salified or esterified carboxy,
R$_2$, R$_3$ and R$_4$ represent independently from each other:
 a hydrogen atom, or
 a linear or branched ($C_1$-$C_{12}$)-alkyl, preferably a ($C_1$-$C_6$)-alkyl, more preferably a ($C_1$-$C_3$)-alkyl, or
 a linear or branched ($C_1$-$C_{12}$)-acyl, preferably a ($C_1$-$C_6$)-acyl, more preferably a ($C_1$-$C_3$)-acyl,
R$_5$ represents:
 a hydrogen atom, or
 a linear or branched ($C_1$-$C_{13}$)-alkyl, preferably a ($C_1$-$C_6$)-alkyl, possibly substituted by up to 3 radicals selected from:
  —OH,
  —O-linear ($C_1$-$C_{12}$)-alkyl, preferably a ($C_1$-$C_6$)-alkyl, possibly substituted by an oxo group,
  a halogen atom F,
  a possibly salified or esterified carboxy,
  an oxo group,
  an aromatic or heteroaromatic aryl possibly substituted by:
   —OH,
   —O-linear ($C_1$-$C_{12}$)-alkyl, preferably a ($C_1$-$C_6$)-alkyl, more preferably a ($C_1$-$C_2$)-alkyl,
   a halogen atom F,
   a possibly salified or esterified carboxy,
and R$_5$ can be possibly interrupted by up to 2 heteroatoms selected from O or N,
R$_6$ represents:
 a hydrogen atom, or
 a linear or branched ($C_1$-$C_{12}$)-alkyl, preferably a ($C_1$-$C_6$)-alkyl, possibly substituted by up to 3 radicals selected from:
  —OH,
  —O-linear ($C_1$-$C_{12}$)-alkyl, preferably a ($C_1$-$C_6$)-alkyl,
  a halogen atom F,
  a possibly salified or esterified carboxy,
  an oxo group,
  an aromatic or heteroaromatic aryl possibly substituted by:
   —OH,
   —O-linear ($C_1$-$C_{12}$)-alkyl, preferably a ($C_1$-$C_6$)-alkyl, more preferably ($C_1$-$C_2$)-alkyl,
   a halogen atom F,
   a possibly salified or esterified carboxy, or
 a linear or branched ($C_1$-$C_{12}$)-acyl, preferably a ($C_1$-$C_6$)-acyl, possibly substituted by up to 3 radicals selected from:
  —OH,
  —O-linear ($C_1$-$C_{12}$)-alkyl, preferably a ($C_1$-$C_6$)-alkyl,
  a halogen atom F,
  a possibly salified or esterified carboxy,
  an oxo group,
  an aromatic or heteroaromatic aryl possibly substituted by:
   —OH,
   —O-linear ($C_1$-$C_{12}$)-alkyl, preferably a ($C_1$-$C_6$)-alkyl, more preferably ($C_1$-$C_2$)-alkyl,
   a halogen atom F,
   a possibly salified or esterified carboxy,
and R$_6$ can be possibly interrupted by up to 3 heteroatoms selected from O or N,
or R$_5$ and R$_6$ represent together with the N atom to which R$_6$ is bound and the carbon atom to which R$_5$ is bound an alkylene radical Z having 2 to 5 carbon atoms which is possibly interrupted by 1 or 2 heteroatoms selected from O and N and/or terminated by an heteroatom selected from O and N and/or possibly substituted by up to three radicals selected from:
 —OH,
 —O-linear ($C_1$-$C_{12}$)-alkyl, preferably a ($C_1$-$C_6$)-alkyl,
 a halogen atom F,
 a possibly salified or esterified carboxy,
 an oxo group,
 an aromatic or heteroaromatic aryl possibly substituted by:
  —OH,
  —O-linear ($C_1$-$C_{12}$)-alkyl, preferably a ($C_1$-$C_6$)-alkyl, more preferably a ($C_1$-$C_2$)-alkyl,
  a halogen atom F,
  a possibly salified or esterified carboxy,
and the pharmaceutically acceptable salts, enantiomers, diastereoisomers of same, as well as mixture of same,
and further comprising at least one disinfecting agent,
for their use for the treatment and/or the prevention of biofilm formation.

In another embodiment, the present invention relates to a composition comprising or consisting in as active ingredient one or more of the compounds of the formula I, II, III, IV, V, VI, VII, VIII, IX, X, XI or XII as previously defined, in association with one or several disinfecting agent,
for their use for the treatment and/or the prevention of biofilm formation.

In another embodiment, the present invention relates to a composition comprising or consisting in as active ingredient one or more of the compounds of the formula I, II, III, IV, V, VI, VII, VIII, IX, X, XI or XII as previously defined, and further comprising a disinfecting agent selected from the group consisting of antioxidants, phosphates, colouring agents, EDTA, or a combination thereof, for their use for the treatment and/or the prevention of biofilm formation.
In another embodiment, the present invention relates to the above-mentioned compositions comprising or consisting in one or more of the following compounds:
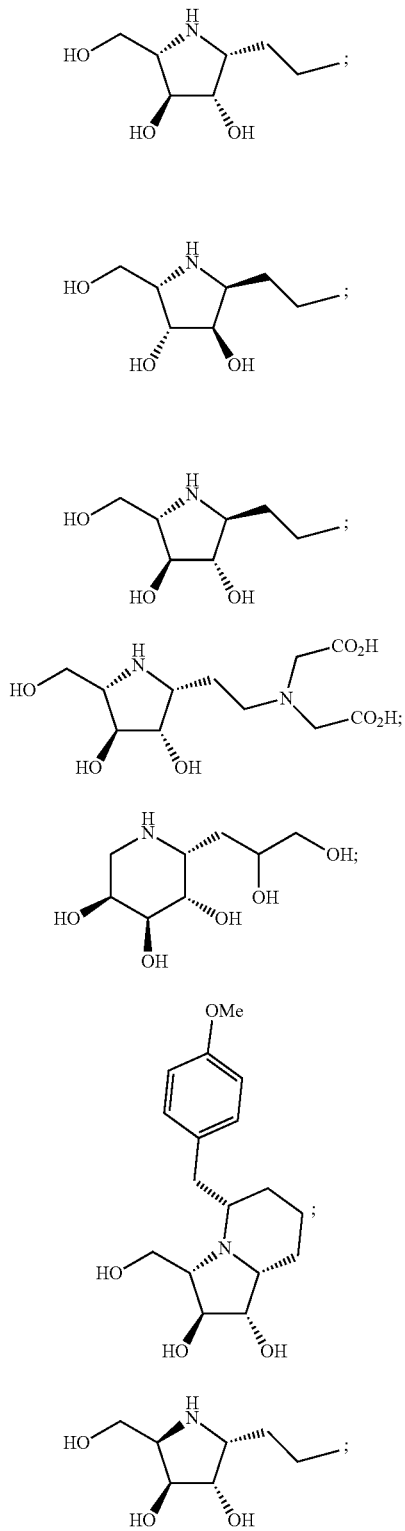
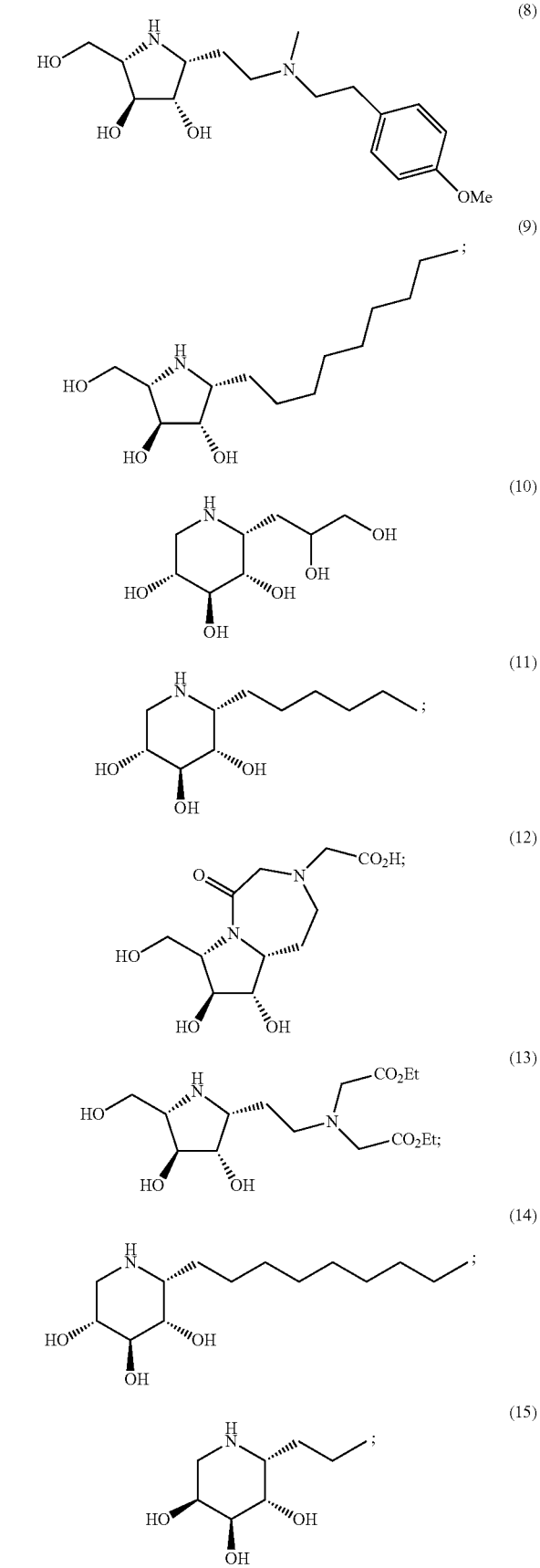

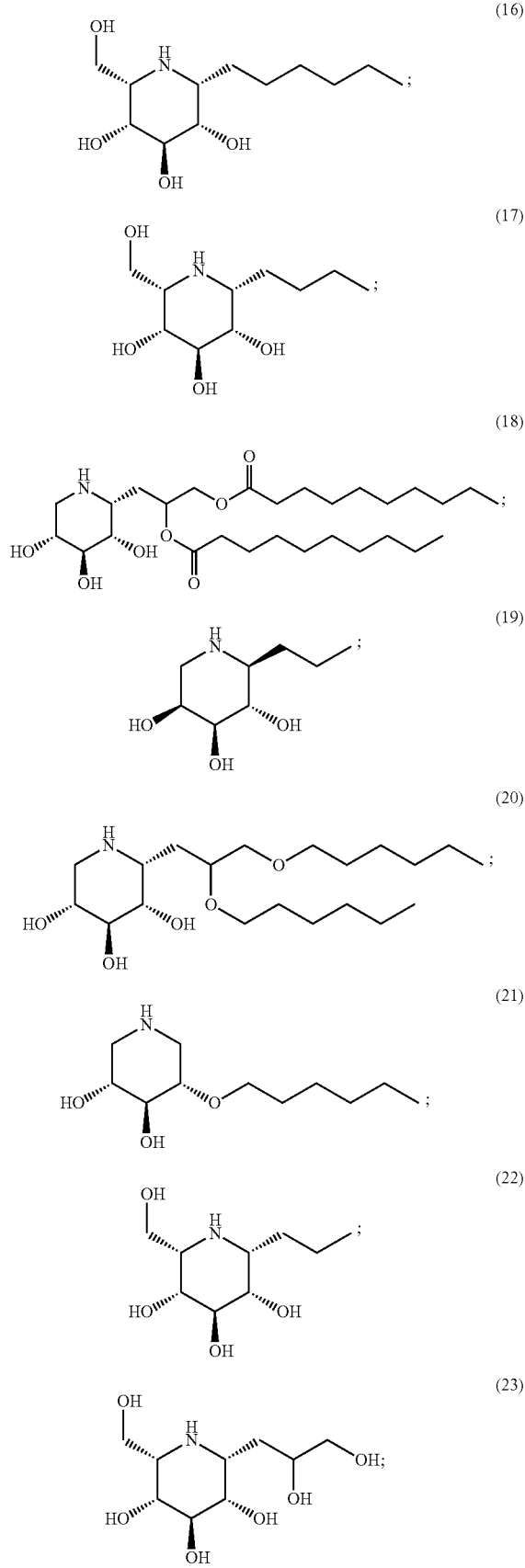

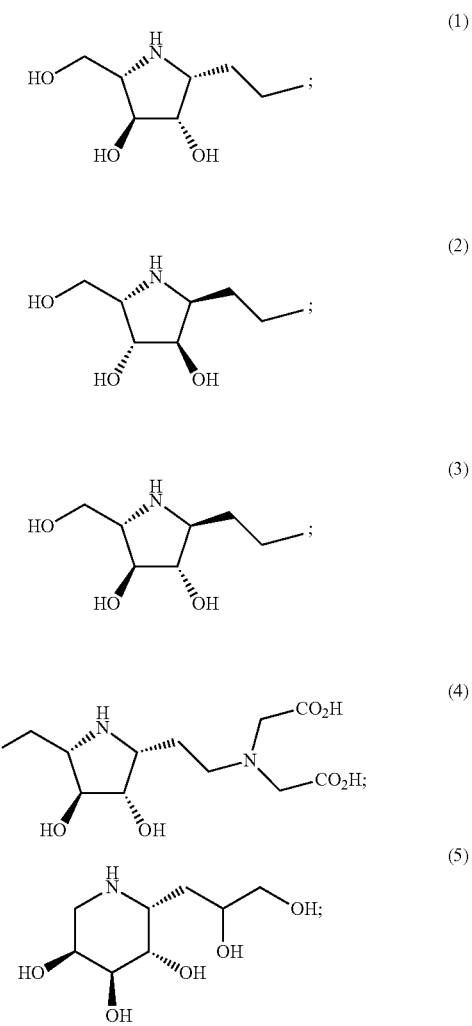

and the pharmaceutically acceptable salts, enantiomers, diastereoisomers of same, as well as mixture of same, in association with one or several antibiotics, notably at least one antibiotic selected from the group comprising or consisting of aminoglycosides, quinolones, cephalosporins, ureidopenicillines, carbapenems, polymyxins and monobactams, more particularly selected from the group comprising or consisting of Amikacin, Ciprofloxacin, Gentamicin, Piperacilin, Tobramycin, and Ceftazidime, for their use for the treatment and/or the prevention of biofilm formation.

In another embodiment, the present invention relates to the above-mentioned compositions comprising or consisting in one or more of the following compounds:

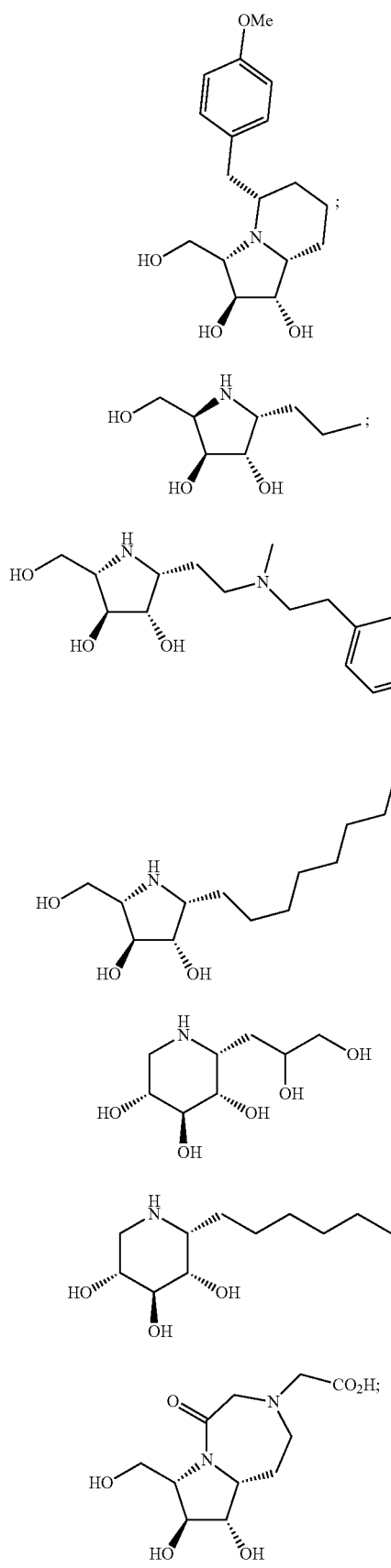
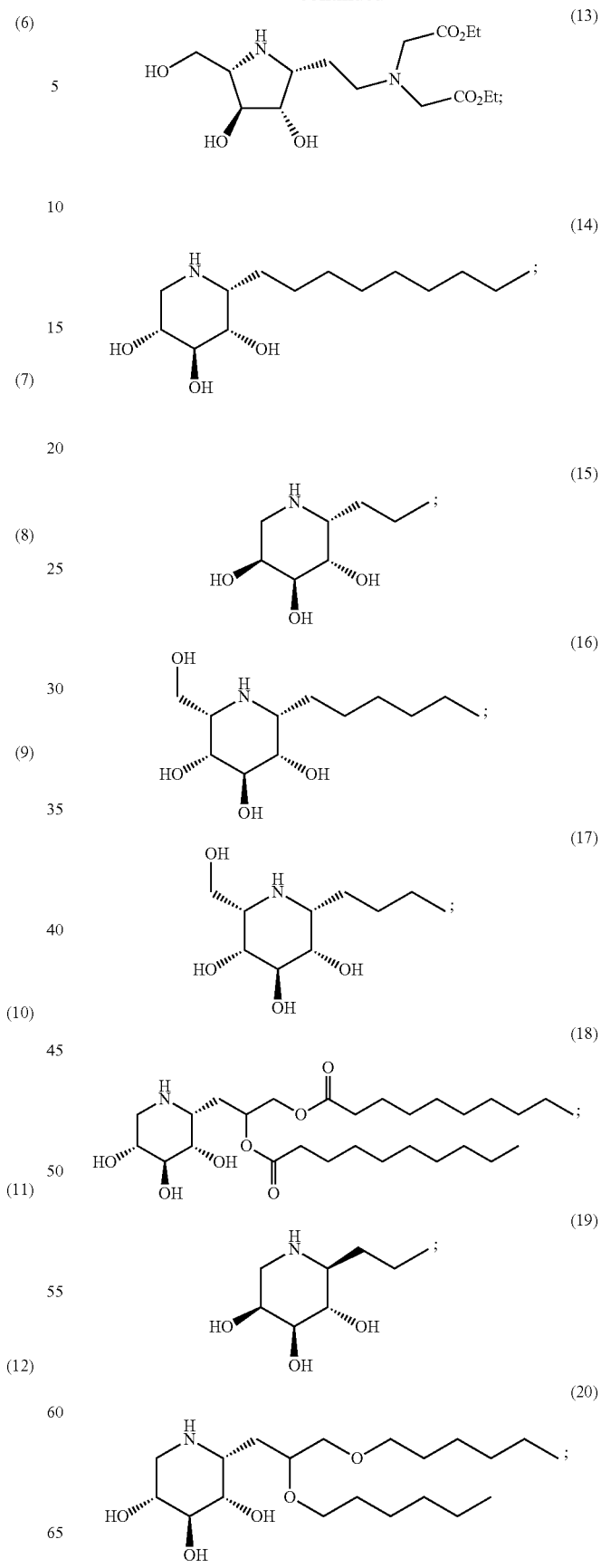

-continued

(21)
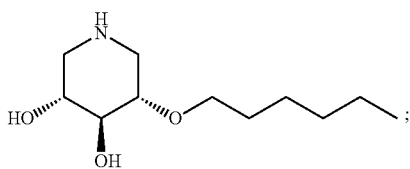

(22)
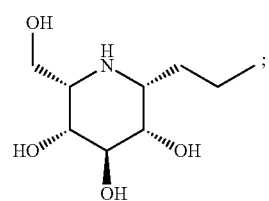

(23)
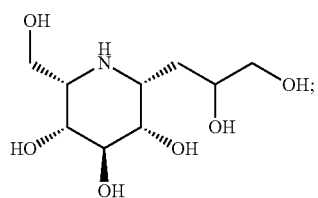

(24)
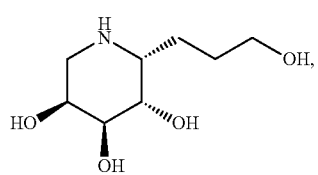

and the pharmaceutically acceptable salts, enantiomers, diastereoisomers of same, as well as mixture of same, in association with one or several disinfecting agent, notably selected from the group consisting of antioxidants, phosphates, colouring agents, EDTA, or a combination thereof, for their use for the treatment and/or the prevention of biofilm formation.

In a preferred embodiment, the present invention relates to the above-mentioned compositions comprising or consisting in at least one compound chosen among:

1
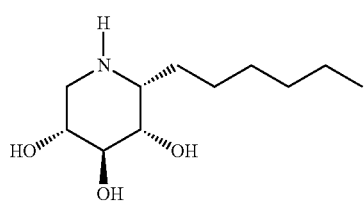

2
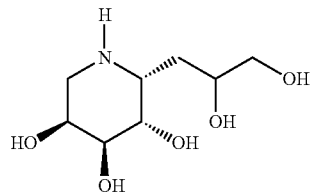

-continued

3
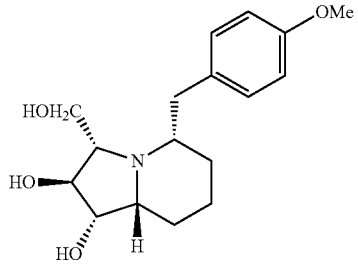

4
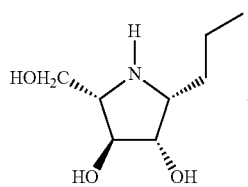

and at least one antibiotic chosen among: Amikacin, Ciprofloxacin, Gentamicin, Piperacilin, Tobramycin, and Ceftazidime, for their use for the treatment and/or the prevention of biofilm formation.

In another embodiment, the present invention also relates to the above-mentioned compositions for their above-mentioned uses comprising or consisting in as active ingredient the compounds of formula I, II, III, IV, V, VI, VII, VIII, IX, X, XI or XII, wherein:

$R_5$ represents:
  a linear or branched $(C_1-C_{13})$-alkyl, preferably a $(C_1-C_6)$-alkyl, possibly substituted by up to 3 radicals selected from:
    —OH,
    —O-linear $(C_1-C_{12})$-alkyl, preferably a $(C_1-C_6)$-alkyl, possibly substituted by an oxo group,
    a possibly salified or esterified carboxy,
    an oxo group,
    an aromatic or heteroaromatic aryl possibly substituted by:
      —O-linear $(C_1-C_{12})$-alkyl, preferably a $(C_1-C_6)$-alkyl, and $R_5$ can be possibly interrupted by up to 3 heteroatoms selected from O, S or N, notably O and N, $R_6$ represents a hydrogen atom, or or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
  a possibly salified or esterified carboxy,
  an oxo group,
  an aromatic or heteroaromatic aryl possibly substituted by:
    O-linear $(C_1-C_{12})$-alkyl, preferably a $(C_1-C_6)$-alkyl, and the pharmaceutically acceptable salts, enantiomers, diastereoisomers of same, as well as mixture of same.

In another embodiment, the present invention also relates to the above-mentioned compositions for their above-mentioned uses comprising or consisting in as active ingredient the compounds of formula I, II, III, IV, V, VI, VII, VIII, IX, X, XI or XII, wherein:

$R_5$ represents:
  a linear or branched $(C_1-C_{13})$-alkyl, preferably a $(C_1-C_6)$-alkyl, possibly substituted by up to 3 radicals selected from:
    —O-linear $(C_1-C_{12})$-alkyl, preferably a $(C_1-C_6)$-alkyl, possibly substituted by an oxo group,
    a possibly salified or esterified carboxy,
    an oxo group,
    an aromatic or heteroaromatic aryl possibly substituted by:
      —O-linear $(C_1-C_{12})$-alkyl, preferably a $(C_1-C_6)$-alkyl,
and $R_5$ can be possibly interrupted by up to 3 heteroatoms selected from O or N, notably with the proviso that $R_5$ cannot be linear $C_4$-alkyl if $R_2$, $R_3$ and $R_4$ are hydrogen atom, more particularly if m represents 1,
$R_6$ represents a hydrogen atom, or
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and substituted by up to three radicals selected from:
  a possibly salified or esterified carboxy,
  an oxo group,
  an aromatic or heteroaromatic aryl possibly substituted by:
    O-linear $(C_1-C_{12})$-alkyl, preferably a $(C_1-C_6)$-alkyl.
and the pharmaceutically acceptable salts, enantiomers, diastereoisomers of same, as well as mixture of same.

In another embodiment, the present invention also relates to the above-mentioned compositions for their above-mentioned uses comprising or consisting in as active ingredient the compounds of formula I, II, III, IV, V, VI, VII, VIII, IX, X, XI or XII, notably XII, wherein:
R5 represents:
  a linear or branched $(C_1-C_{13})$-alkyl, preferably a $(C_1-C_6)$-alkyl, possibly substituted by up to 3 radicals selected from:
    a possibly salified or esterified carboxy,
    an aromatic or heteroaromatic aryl possibly substituted by:
      —O-linear $(C_1-C_{12})$ alkyl, preferably a $(C_1-C_6)$-alkyl
and $R_5$ can be possibly interrupted by up to 3 heteroatoms selected from O, S or N, notably N preferably, with the proviso that $R_5$ cannot be a linear $C_4$-alkyl if $R_2$, $R_3$ and $R_4$ are hydrogen atom, more particularly if $R_6$ is a hydrogen atom,
and the pharmaceutically acceptable salts, enantiomers, diastereoisomers of same, as well as mixture of same.

In another embodiment, the present invention also relates to the above-mentioned compositions for their above-mentioned uses comprising or consisting in as active ingredient the compounds of formula I, II, III, IV, V, VI, VII, VIII, IX, X, XI or XII, notably IV, wherein:
$R_2$, $R_3$ and $R_4$ represent a hydrogen atom,
$R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N, notably N, and/or terminated by an heteroatom selected from O, S, N and/or possibly substituted by up to three radicals selected from:
  a possibly salified or esterified carboxy,
  an oxo group,
  an aromatic or heteroaromatic aryl possibly substituted by:
    O-linear $(C_1-C_{12})$-alkyl, preferably a $(C_1-C_6)$-alkyl,
and the pharmaceutically acceptable salts, enantiomers, diastereoisomers of same, as well as mixture of same.

In another embodiment, the present invention also relates to the above-mentioned compositions for their above-mentioned uses comprising or consisting in as active ingredient the compounds of formula I, II, III, IV, V, VI, VII, VIII, IX, X, XI or XII, notably XI, for their above-mentioned uses, wherein:
$R_5$ represents:
  a linear or branched $(C_1-C_{13})$-alkyl, preferably a $(C_1-C_6)$-alkyl, possibly substituted by up to 3 radicals selected from:
    —OH,
    —O-linear $(C_1-C_{12})$-alkyl, preferably a $(C_1-C_6)$-alkyl, possibly substituted by an oxo group,
    an oxo group,
and the pharmaceutically acceptable salts, enantiomers, diastereoisomers of same, as well as mixture of same.

In a ninth embodiment, the present invention relates to the use of at least one compound of the following formula I:

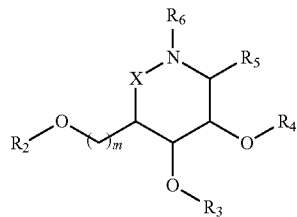

wherein X, m, R2, R3, R4, R5 and R6 are as defined previously, as disinfectant.

In another embodiment, the present invention relates to the use of at least one compound of the following formula II:

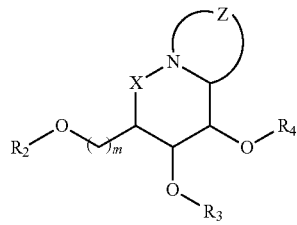

wherein X, m, R2, R3, R4 and Z are as defined previously, as disinfectant.

In another embodiment, the present invention relates to the use of at least one compound of formula III, IV, V, VI, VII, VIII, IX, X, XI or XII as defined previously, as disinfectant.

In another embodiment, the present invention relates to the use of a composition, as disinfectant, comprising as active ingredient one or more of the compounds of the formula I, II, III, IV, V, VI, VII, VIII, IX, XI or XII as previously defined, in association with one or several disinfecting agents, notably an agent selected from the group consisting of antioxidants, phosphates, colouring agents, EDTA, or a combination thereof.

In another embodiment, the present invention relates to the use of a composition, as disinfectant, comprising or consisting in as active ingredient one or more of the compounds of the following formula I:

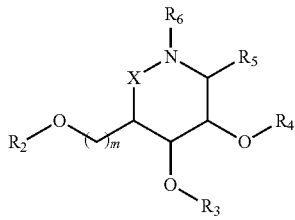

wherein:

m represents an integer being equal to 0, 1, 2, 3, 4, 5 or 6,

X represents a simple bond or a radical —$CHR_1$— wherein $R_1$ represents:
  a hydrogen atom, or
  a linear or branched, possibly interrupted by up to 3 heteroatoms selected from O, S or N and/or possibly substituted, ($C_1$-$C_{12}$)-alkyl, $R_2$, $R_3$ and $R_4$ represent independently from each other:
  a hydrogen atom, or
  a linear or branched ($C_1$-$C_{12}$)-alkyl, or
  a linear or branched ($C_1$-$C_{12}$)-acyl, $R_5$ represents:
  a hydrogen atom, or
  a linear or branched, possibly substituted, ($C_1$-$C_{13}$)-alkyl, or
  a linear or branched, possibly substituted ($C_1$-$C_{13}$)-alkyl interrupted by up to 3 heteroatoms selected from O, S or N, $R_6$ represents:
  a hydrogen atom, or
  a linear or branched possibly substituted ($C_1$-$C_{12}$)-alkyl, or
  a linear or branched possibly substituted ($C_1$-$C_{12}$)-acyl, or
  a linear or branched, possibly substituted ($C_1$-$C_{12}$)-alkyl interrupted by up to 3 heteroatoms selected from O, S or N, or
  a linear or branched, possibly substituted ($C_1$-$C_{12}$)-acyl interrupted by up to 3 heteroatoms selected from O, S or N, or $R_5$ and $R_6$ represent together with the N atom to which $R_6$ is bound and the carbon atom to which $R_5$ is bound an alkylene radical Z having 2 to 5 carbon atoms which is possibly substituted and/or possibly interrupted by up to 3 heteroatoms selected from O, S, N and/or terminated by an heteroatom selected from O, S, N, and the acceptable salts, enantiomers, diastereoisomers of same, as well as mixture of same, and further comprising at least one disinfecting agent.

In another embodiment, the present invention relates to the use of a composition, as disinfectant, comprising or consisting in as active ingredient one or more of the compounds of the following formula I:

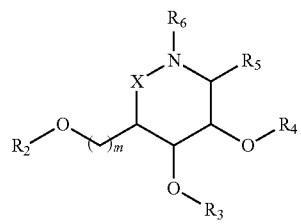

wherein:

m represents an integer being equal to 0, 1, 2, 3, 4, 5 or 6,

X represents a simple bond or a radical —$CHR_1$— wherein $R_1$ represents:
  a hydrogen atom, or
  a linear or branched ($C_1$-$C_{12}$)-alkyl, preferably a ($C_1$-$C_6$)-alkyl, possibly interrupted by up to 3 heteroatoms selected from O, S or N and/or possibly substituted by up to 3 radicals selected from:
    —OH,
    —O-linear ($C_1$-$C_{12}$)-alkyl, preferably a ($C_1$-$C_6$)-alkyl,
    —O-linear ($C_1$-$C_{12}$)-acyl, preferably a ($C_1$-$C_6$)-acyl,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl,
      —O-linear ($C_1$-$C_{12}$)-acyl, preferably a ($C_1$-$C_6$)-acyl,
      a halogen atom chosen among Br, Cl, I, F, preferably F,
      a possibly salified or esterified carboxy,
    a possibly salified or esterified carboxy ($C_1$-$C_{12}$)-alkyl, preferably a ($C_1$-$C_6$)-alkyl, $R_2$, $R_3$ and $R_4$ represent independently from each other:
  a hydrogen atom, or
  a linear or branched ($C_1$-$C_{12}$)-alkyl, preferably a ($C_1$-$C_6$)-alkyl, or
  a linear or branched ($C_1$-$C_{12}$)-acyl, preferably a ($C_1$-$C_6$)-acyl, $R_5$ represents:
  a hydrogen atom, or
  a linear or branched ($C_1$-$C_{13}$)-alkyl, preferably a ($C_1$-$C_6$)-alkyl, possibly substituted by up to 3 radicals selected from:
    —OH,
    —O-linear ($C_1$-$C_{12}$)-alkyl, preferably a ($C_1$-$C_6$)-alkyl, possibly substituted by an oxo group,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear ($C_1$-$C_{12}$)-alkyl, preferably a ($C_1$-$C_6$)-alkyl,
      a halogen atom chosen among Br, Cl, I, F, preferably F,
      a possibly salified or esterified carboxy,
    a possibly salified or esterified carboxy ($C_1$-$C_{12}$)-alkyl, preferably a ($C_1$-$C_6$)-alkyl, and $R_5$ can be possibly interrupted by up to 3 heteroatoms selected from O, S or N, $R_6$ represents:
  a hydrogen atom, or
  a linear or branched $(C_1\text{-}C_{12})$-alkyl, preferably a $(C_1\text{-}C_6)$-alkyl, possibly substituted by up to 3 radicals selected from:
    —OH,
    —O-linear $(C_1\text{-}C_{12})$-alkyl, preferably a $(C_1\text{-}C_6)$-alkyl,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear $(C_1\text{-}C_{12})$-alkyl, preferably a $(C_1\text{-}C_6)$-alkyl,
      a halogen atom chosen among Br, Cl, I, F, preferably F,
      a possibly salified or esterified carboxy,
      a possibly salified or esterified carboxy $(C_1\text{-}C_{12})$-alkyl, preferably a $(C_1\text{-}C_6)$-alkyl, or
  a linear or branched $(C_1\text{-}C_{12})$-acyl, preferably a $(C_1\text{-}C_6)$-acyl, possibly substituted by up to 3 radicals selected from:
    —OH,
    —O-linear $(C_1\text{-}C_{12})$-alkyl, preferably a $(C_1\text{-}C_6)$-alkyl,
    a halogen atom chosen among Br, Cl, I, F, preferably F,
    a possibly salified or esterified carboxy,
    an oxo group,
    an aromatic or heteroaromatic aryl possibly substituted by:
      —OH,
      —O-linear $(C_1\text{-}C_{12})$-alkyl, preferably a $(C_1\text{-}C_6)$-alkyl,
      a halogen atom chosen among Br, Cl, I, F, preferably F,
      a possibly salified or esterified carboxy,
      a possibly salified or esterified carboxy $(C_1\text{-}C_{12})$-alkyl, preferably a $(C_1\text{-}C_6)$-alkyl,
and $R_6$ can be possibly interrupted by up to 3 heteroatoms selected from O, S or N,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
  —OH,
  —O-linear $(C_1\text{-}C_{12})$-alkyl, preferably a $(C_1\text{-}C_6)$-alkyl,
  a halogen atom chosen among Br, Cl, I, F, preferably F,
  a possibly salified or esterified carboxy,
  an oxo group,
  an aromatic or heteroaromatic aryl possibly substituted by:
    —OH,
    —O-linear $(C_1\text{-}C_{12})$-alkyl, preferably a $(C_1\text{-}C_6)$-alkyl,
    a halogen atom chosen among Br, Cl, I, F, preferably F,
    a possibly salified or esterified carboxy,
    a possibly salified or esterified carboxy $(C_1\text{-}C_{12})$-alkyl, preferably a $(C_1\text{-}C_6)$-alkyl,
and the acceptable salts, enantiomers, diastereoisomers of same, as well as mixture of same and further comprising at least one disinfecting agent.

In another embodiment, the present invention relates to the use of a composition, as disinfectant, comprising or consisting in as active ingredient one or more of the compounds of the following formula I:

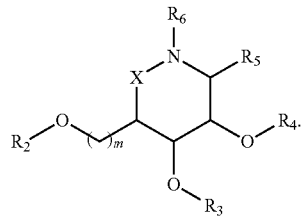

wherein:
m represents an integer being equal to 0, 1, 2,
X represents a simple bond or a radical —$CHR_1$— wherein $R_1$ represents:
  a hydrogen atom, or
  a linear or branched $(C_1\text{-}C_{12})$-alkyl, preferably a $(C_1\text{-}C_6)$-alkyl, possibly interrupted by up to 3 heteroatoms selected from O and/or possibly substituted by up to 3 radicals selected from:
    —OH,
    —O-linear $(C_1\text{-}C_{12})$-alkyl, preferably a $(C_1\text{-}C_6)$-alkyl,
    —O-linear $(C_1\text{-}C_{12})$-acyl, preferably a $(C_1\text{-}C_6)$-acyl,
    a halogen atom F,
    a possibly salified or esterified carboxy,
    an oxo group,
    an aromatic or heteroaromatic aryl possibly substituted by:
      —OH,
      —O-linear $(C_1\text{-}C_{12})$-alkyl, preferably a $(C_1\text{-}C_6)$-alkyl, more preferably a $(C_1\text{-}C_2)$-alkyl,
      a halogen atom F,
      a possibly salified or esterified carboxy,
$R_2$, $R_3$ and $R_4$ represent independently from each other:
  a hydrogen atom, or
  a linear or branched $(C_1\text{-}C_{12})$-alkyl, preferably a $(C_1\text{-}C_6)$-alkyl, more preferably a $(C_1\text{-}C_3)$-alkyl, or
  a linear or branched $(C_1\text{-}C_{12})$-acyl, preferably a $(C_1\text{-}C_6)$-acyl, more preferably a $(C_1\text{-}C_3)$-acyl,
$R_5$ represents:
  a hydrogen atom, or
  a linear or branched $(C_1\text{-}C_{13})$-alkyl, preferably a $(C_1\text{-}C_6)$-alkyl, possibly substituted by up to 3 radicals selected from:
    —OH,
    —O-linear $(C_1\text{-}C_{12})$-alkyl, preferably a $(C_1\text{-}C_6)$-alkyl, possibly substituted by an oxo group,
    a halogen atom F,
    a possibly salified or esterified carboxy,
    an oxo group,
    an aromatic or heteroaromatic aryl possibly substituted by:
      —OH,
      —O-linear $(C_1\text{-}C_{12})$-alkyl, preferably a $(C_1\text{-}C_6)$-alkyl, more preferably a $(C_1\text{-}C_2)$-alkyl,
      a halogen atom F,
      a possibly salified or esterified carboxy,
and $R_5$ can be possibly interrupted by up to 2 heteroatoms selected from O or N,
$R_6$ represents:
  a hydrogen atom, or
  a linear or branched $(C_1\text{-}C_{12})$-alkyl, preferably a $(C_1\text{-}C_6)$-alkyl, possibly substituted by up to 3 radicals selected from:
    —OH,
    —O-linear $(C_1\text{-}C_{12})$-alkyl, preferably a $(C_1\text{-}C_6)$-alkyl,
    a halogen atom F, a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably $(C_1-C_2)$-alkyl,
a halogen atom F,
a possibly salified or esterified carboxy, or
a linear or branched $(C_1-C_{12})$-acyl, preferably a $(C_1-C_6)$-acyl, possibly substituted by up to 3 radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably $(C_1-C_2)$-alkyl,
a halogen atom F,
a possibly salified or esterified carboxy,
and $R_6$ can be possibly interrupted by up to 3 heteroatoms selected from O or N,
or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O and N and/or terminated by an heteroatom selected from O and N and/or possibly substituted by up to three radicals selected from:
—OH,
—O-linear $(C_1-C_{12})$-alkyl, preferably a $(C_1-C_6)$-alkyl,
a halogen atom F,
a possibly salified or esterified carboxy,
an oxo group,
an aromatic or heteroaromatic aryl possibly substituted by:
—OH,
—O-linear $(C_1-C_{12})$-alkyl, preferably a $(C_1-C_6)$-alkyl, more preferably a $(C_1-C_2)$-alkyl,
a halogen atom F,
a possibly salified or esterified carboxy,
and the acceptable salts, enantiomers, diastereoisomers of same, as well as mixture of same, and further comprising at least one disinfecting agent.

In another embodiment, the present invention relates to the use of a composition, as disinfectant, comprising or consisting in as active ingredient one or more of the compounds of the formula I, II, III, IV, V, VI, VII, VIII, IX, X, XI or XII as previously defined, in association with one or several disinfecting agent.

In another embodiment, the present invention relates to the use of a composition, as disinfectant, comprising or consisting in as active ingredient one or more of the compounds of the formula I, II, III, IV, V, VI, VII, VIII, IX, X, XI or XII as previously defined, and further comprising a disinfecting agent selected from the group consisting of antioxidants, phosphates, colouring agents, EDTA, or a combination thereof.

In another embodiment, the present invention relates to the use of the above-mentioned compositions, as disinfectant, comprising or consisting in one or more of the following compounds:

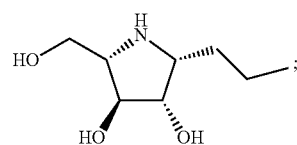
(1)

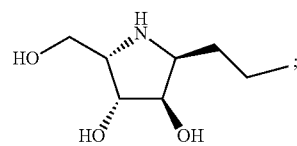
(2)

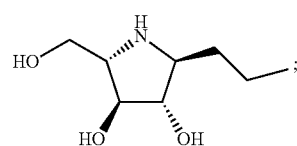
(3)

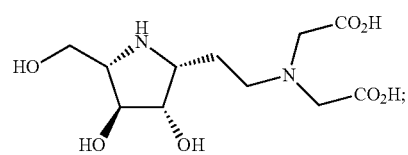
(4)

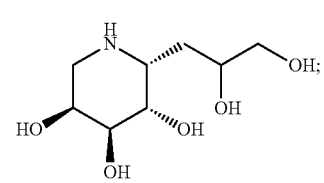
(5)

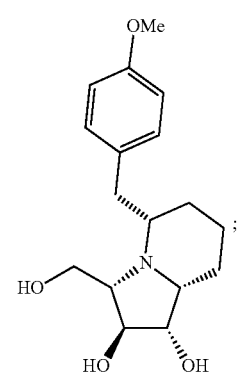
(6)

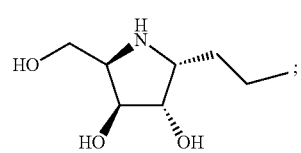
(7)

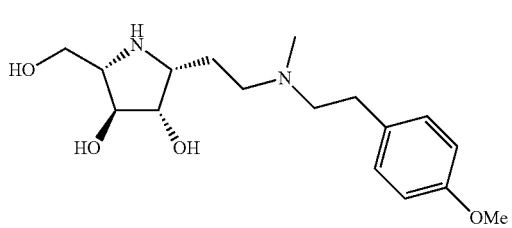
(8)

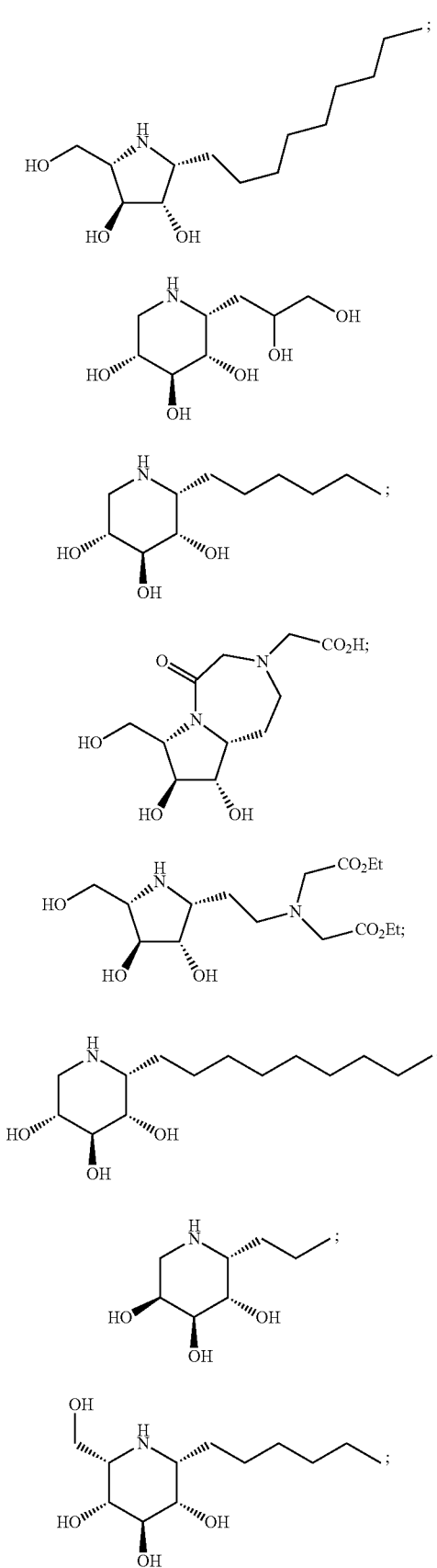
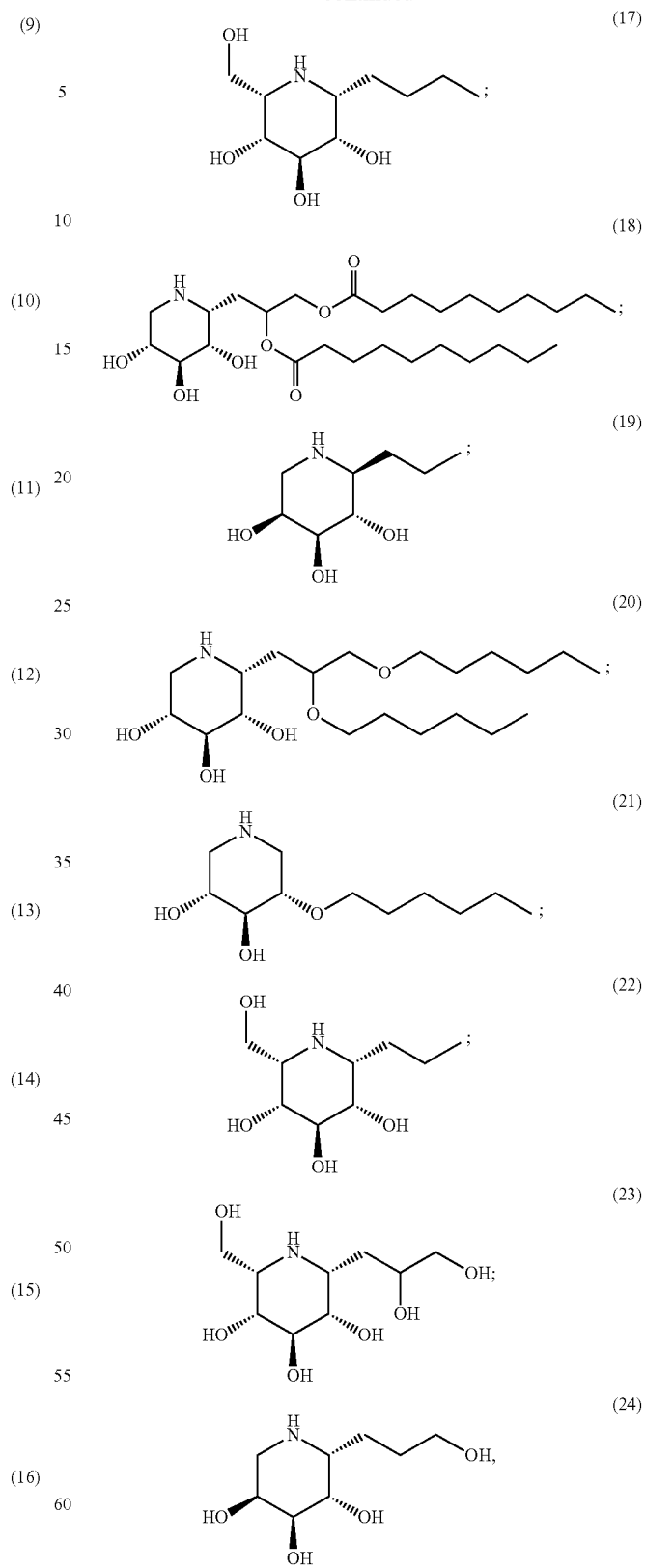
and the acceptable salts, enantiomers, diastereoisomers of same, as well as mixture of same, in association with one or several disinfecting agent, notably selected from the group consisting of antioxidants, phosphates, colouring agents, EDTA, or a combination thereof.

In another embodiment, the present invention also relates to the use of the above-mentioned compositions, as disinfectant, comprising or consisting in as active ingredient the compounds of formula I, II, III, IV, V, VI, VII, VII, IX, X, XI or XII, wherein:

$R_5$ represents:
- a linear or branched $(C_1-C_{13})$-alkyl, preferably a $(C_1-C_6)$-alkyl, possibly substituted by up to 3 radicals selected from:
  - —OH,
  - —O-linear $(C_1-C_{12})$-alkyl, preferably a $(C_1-C_6)$-alkyl, possibly substituted by an oxo group,
  - a possibly salified or esterified carboxy,
  - an oxo group,
  - an aromatic or heteroaromatic aryl possibly substituted by:
    - —O-linear $(C_1-C_{12})$-alkyl, preferably a $(C_1-C_6)$-alkyl, and $R_5$ can be possibly interrupted by up to 3 heteroatoms selected from O, S or N, notably O and N, $R_6$ represents a hydrogen atom, or or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and/or possibly substituted by up to three radicals selected from:
- a possibly salified or esterified carboxy,
- an oxo group,
- an aromatic or heteroaromatic aryl possibly substituted by:
  - O-linear $(C_1-C_{12})$-alkyl, preferably a $(C_1-C_6)$-alkyl, and the acceptable salts, enantiomers, diastereoisomers of same, as well as mixture of same.

In another embodiment, the present invention also relates to the use of the above-mentioned compositions, as disinfectant, comprising or consisting in as active ingredient the compounds of formula I, II, III, IV, V, VI, VII, VIII, IX, X, XI or XII, wherein:

$R_5$ represents:
- a linear or branched $(C_1-C_{13})$-alkyl, preferably a $(C_1-C_6)$-alkyl, possibly substituted by up to 3 radicals selected from:
  - —O-linear $(C_1-C_{12})$-alkyl, preferably a $(C_1-C_6)$-alkyl, possibly substituted by an oxo group,
  - a possibly salified or esterified carboxy,
  - an oxo group,
  - an aromatic or heteroaromatic aryl possibly substituted by:
    - —O-linear $(C_1-C_{12})$-alkyl, preferably a $(C_1-C_6)$-alkyl, and $R_5$ can be possibly interrupted by up to 3 heteroatoms selected from O or N, with the proviso that $R_5$ cannot be linear $C_4$-alkyl if $R_2$, $R_3$ and $R_4$ are hydrogen atom, more particularly if m represents 1, $R_6$ represents a hydrogen atom, or or $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N and/or terminated by an heteroatom selected from O, S, N and substituted by up to three radicals selected from:
- a possibly salified or esterified carboxy,
- an oxo group,
- an aromatic or heteroaromatic aryl possibly substituted by:
  - O-linear $(C_1-C_{12})$-alkyl, preferably a $(C_1-C_6)$-alkyl.

and the acceptable salts, enantiomers, diastereoisomers of same, as well as mixture of same.

In another embodiment, the present invention also relates to the use of the above-mentioned compositions, as disinfectant, comprising or consisting in as active ingredient the compounds of formula I, II, III, IV, V, VI, VII, VIII, IX, X, XI or XII, notably XII, wherein:

R5 represents:
- a linear or branched $(C_1-C_{13})$-alkyl, preferably a $(C_1-C_6)$-alkyl, possibly substituted by up to 3 radicals selected from:
  - a possibly salified or esterified carboxy,
  - an aromatic or heteroaromatic aryl possibly substituted by:
    - —O-linear $(C_1-C_{12})$ alkyl, preferably a $(C_1-C_6)$-alkyl and $R_5$ can be possibly interrupted by up to 3 heteroatoms selected from O, S or N, notably N preferably, with the proviso that $R_5$ cannot be a linear $C_4$-alkyl if $R_2$, $R_3$ and $R_4$ are hydrogen atom, more particularly if R6 is a hydrogen atom, and the acceptable salts, enantiomers, diastereoisomers of same, as well as mixture of same.

In another embodiment, the present invention also relates to the use of the above-mentioned compositions, as disinfectant, comprising or consisting in as active ingredient the compounds of formula I, II, III, IV, V, VI, VII, VIII, IX, X, XI or XII, notably IV, wherein:

$R_2$, $R_3$ and $R_4$ represent a hydrogen atom, $R_5$ and $R_6$ represent together with the N atom to which $R_6$ is bound and the carbon atom to which $R_5$ is bound an alkylene radical Z having 2 to 5 carbon atoms which is possibly interrupted by 1 or 2 heteroatoms selected from O, S, N, notably N, and/or terminated by an heteroatom selected from O, S, N and/or possibly substituted by up to three radicals selected from:
- a possibly salified or esterified carboxy,
- an oxo group,
- an aromatic or heteroaromatic aryl possibly substituted by:
  - O-linear $(C_1-C_{12})$-alkyl, preferably a $(C_1-C_6)$-alkyl, and the acceptable salts, enantiomers, diastereoisomers of same, as well as mixture of same.

In another embodiment, the present invention also relates to the use of the above-mentioned compositions, as disinfectant, comprising or consisting in as active ingredient the compounds of formula I, II, III, IV, V, VI, VII, VIII, IX, X, XI or XII, notably XI, wherein:

$R_5$ represents:
- a linear or branched $(C_1-C_{13})$-alkyl, preferably a $(C_1-C_6)$-alkyl, possibly substituted by up to 3 radicals selected from:
  - —OH,
  - —O-linear $(C_1-C_{12})$-alkyl, preferably a $(C_1-C_6)$-alkyl, possibly substituted by an oxo group,
  - an oxo group, and the acceptable salts, enantiomers, diastereoisomers of same, as well as mixture of same.

In a twelfth embodiment, the present invention relates to the use of at least one compound of formula I:

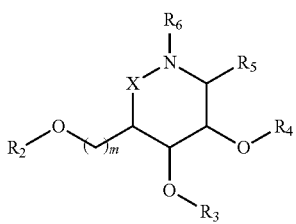

wherein X, m, R2, R3, R4, R5 and R6 are as defined previously, for the preparation of polymers.

The term "polymer" means a large molecule or macromolecule, composed of many repeated subunits.

In another embodiment, the present invention relates to the use of at least one compound of the following formula II:

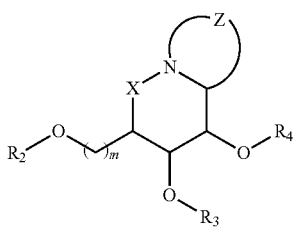

wherein X, m, R2, R3, R4 and Z are as defined previously, for the preparation of polymers.

In another embodiment, the present invention relates to the use of at least one compound of formula III, IV, V, VI, VII, VIII, IX, X, XI or XII as defined previously, for the preparation of polymers.

In a thirteenth embodiment, the present invention relates to a polymer comprising one or more compounds of the following formula I:

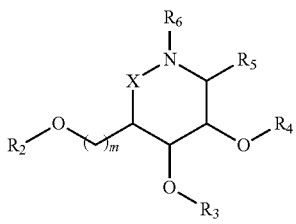

wherein X, m, R2, R3, R4, R5 and R6 are as defined previously.

In another embodiment, the present invention relates to a polymer comprising one or more compounds of the following formula II:

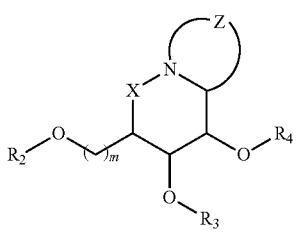

wherein X, m, R2, R3, R4 and Z are as defined previously.

In another embodiment, the present invention relates to a polymer comprising one or more compounds of formula V, VII, IX, X, XI or XII as defined previously.

The compounds of the present invention can be prepared according to the methods described in:

Biela A, Oulaïdi F, Gallienne E, Górecki M, Frelek J, Martin O R. An improved methodology for the synthesis of 1-C-allyl imino-D-xylitol and -L-arabinitol and their rapid functionalization. Tetrahedron 69, 3348-3354 (2013), or Chronowska A, Gallienne E, Nicolas C, Kato A, Adachi I, Martin O R. An expeditious synthesis of an analogue of (−)-steviamine by way of the 1,3-dipolar cycloaddition of a nitrile oxide with a 1-C-allyl iminosugar. Tetrahedron Lett. 52, 6399-6402 (2011).

"1-C-Alkyl imino-D-xylitol and -L-arabinitol derivatives by nucleophilic addition to pentose-derived N-tert-butanesulfinylimines: sugar- vs. chiral auxiliary-induced stereoselectivity" F. Oulaïdi, E. Gallienne, P. Compain, O. R. Martin, Tetrahedron Asymmetry 22, 609-612 (2011).

These documents are incorporated herein by reference in their entirety.

The present invention is illustrated by the following Figures and Examples, which do not limit the scope of the invention.

Congo red staining was used for measuring biofilm formation. Plot depicts mean values±SD of absorbance [λ=492 nm]. The average was calculated on the basis of three replicates (n=3). A high amount of biofilm was observed after 24 hours, followed by plateau and a typical breakdown of biofilm growth after 72 hours of the culture.

Figure 2A:
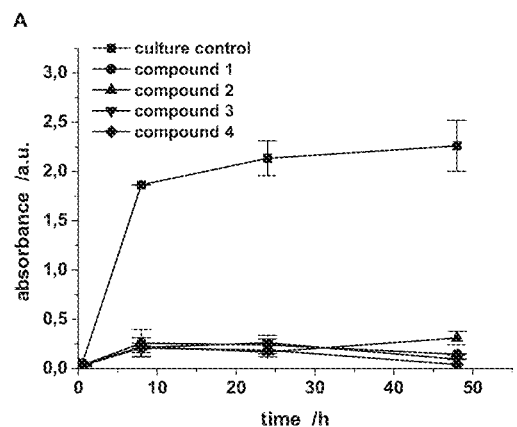

FIG. 2A represents the effect of the tested compounds (1, 2, 3 and 4) on exopolysaccharide biosynthesis in the early stages of P. aeruginosa biofilm formation, on strain PAR 5. The abscissa represents the time (in hours), and the ordinate represents the value of absorbance (in a.u.).

Biofilm formation measured by Red Congo staining at different time points. Results depict mean values±SD calculated from three replicates (n=3). In both experiments P. aeruginosa in TSB broth alone was used as a culture control.

Figure 2B:
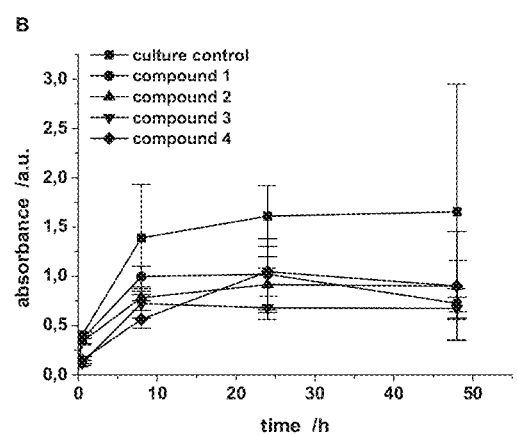

FIG. 2B represents the effect of the tested compounds (1, 2, 3 and 4) on exopolysaccharide biosynthesis in the early stages of P. aeruginosa biofilm formation, on strain PAR 20. The abscissa represents the time (in hours), and the ordinate represents the value of absorbance (in a.u.).

Biofilm formation measured by Red Congo staining at different time points. Results depict mean values±SD calculated from three replicates (n=3). In both experiments P. aeruginosa in TSB broth alone was used as a culture control.

Figure 2C:
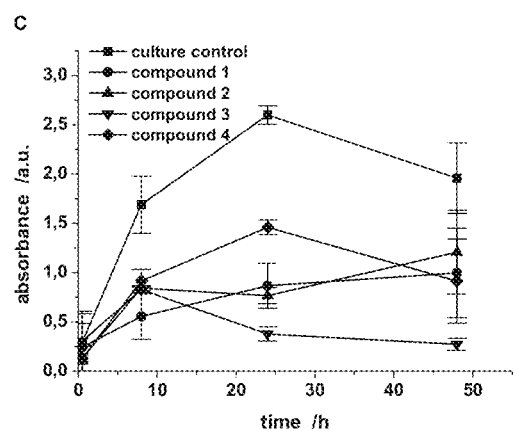

FIG. 2C represents the effect of the tested compounds (1, 2, 3 and 4) on exopolysaccharide biosynthesis in the early stages of P. aeruginosa biofilm formation, on strain PAR 50. The abscissa represents the time (in hours), and the ordinate represents the value of absorbance (in a.u.).

Biofilm formation measured by Red Congo staining at different time points. Results depict mean values±SD calculated from three replicates (n=3). In both experiments P. aeruginosa in TSB broth alone was used as a culture control.

Figure 3A:
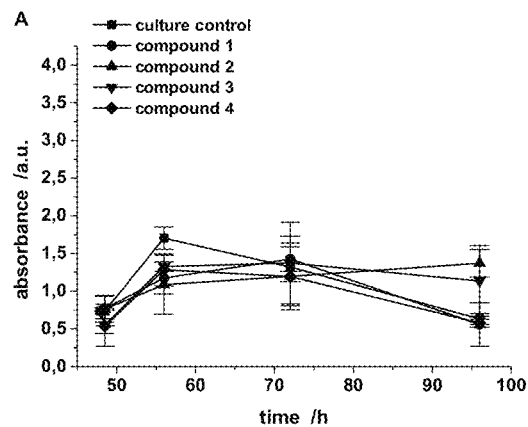

FIG. 3A represents the effect of the tested compounds (1, 2, 3 and 4) on exopolysaccharide biosynthesis on the mature *P. aeruginosa* biofilm, on strain P AR 5. The abscissa represents the time (in hours), and the ordinate represents the value of absorbance (in a.u.).

Figure 3B:
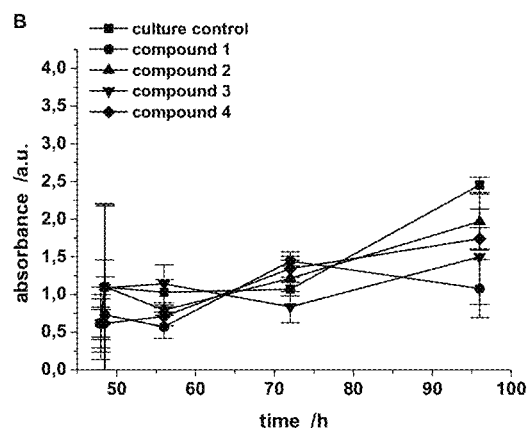

Compounds were added to the bacteria culture 48 h after induction of biofilm. Biofilm development monitored by Red Congo staining at different time points. Results depict mean values±SD calculated from three replicates (n=3). In both experiments *P. aeruginosa* in TSB broth alone was used as a culture control FIG. 3B represents the effect of the tested compounds (1, 2, 3 and 4) on exopolysaccharide biosynthesis on the mature *P. aeruginosa* biofilm, on strain P AR 20. The abscissa represents the time (in hours), and the ordinate represents the value of absorbance (in a.u.).

Figure 3C:
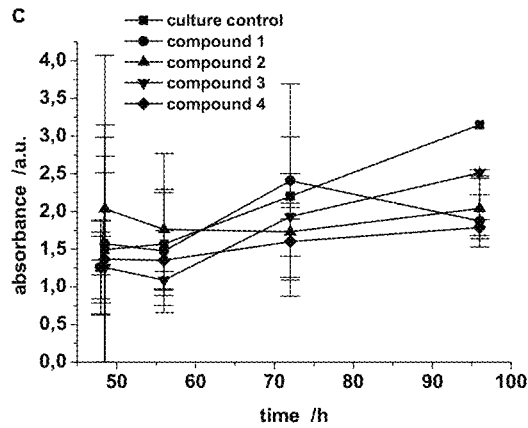

Compounds were added to the bacteria culture 48 h after induction of biofilm. Biofilm development monitored by Red Congo staining at different time points. Results depict mean values±SD calculated from three replicates (n=3). In both experiments *P. aeruginosa* in TSB broth alone was used as a culture control FIG. 3C represents the effect of the tested compounds (1, 2, 3 and 4) on exopolysaccharide biosynthesis on the mature *P. aeruginosa* biofilm, on strain P AR 50. The abscissa represents the time (in hours), and the ordinate represents the value of absorbance (in a.u.).

Figure 4A:
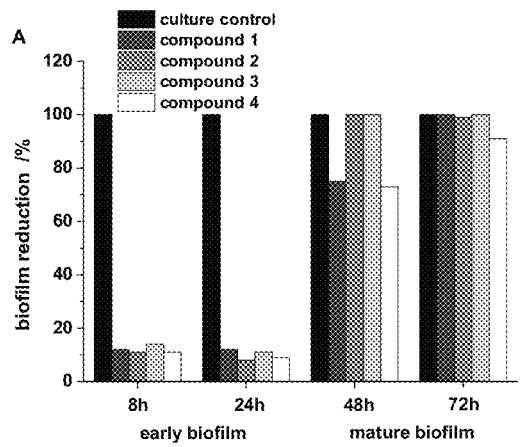

Compounds were added to the bacteria culture 48 h after induction of biofilm. Biofilm development monitored by Red Congo staining at different time points. Results depict mean values±SD calculated from three replicates (n=3). In both experiments *P. aeruginosa* in TSB broth alone was used as a culture control FIG. 4A represents the effect of the tested compounds (1, 2, 3 and 4) on exopolysaccharide biosynthesis in the early stages and mature *P. aeruginosa* biofilm formation, strain PAR 5. The abscissa represents the time (in hours) in order to differentiate early biofilm and mature biofilm, and the ordinate represents the percentage of the biofilm reduction.

The percentage of the reduction in biofilm formation by *P. aeruginosa* is showed after 8 hours, 24 hours, 48 hours and 72 hours of incubation.

Figure 4B:
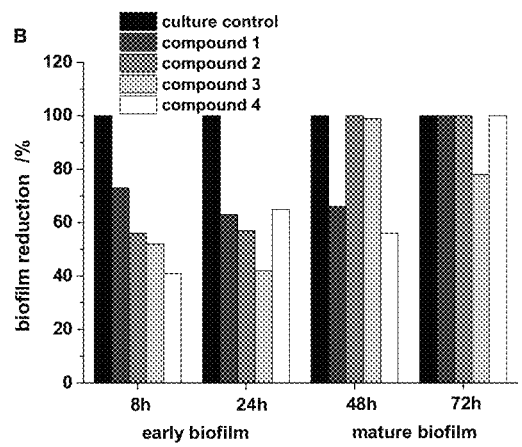

FIG. 4B represents the effect of the tested compounds (1, 2, 3 and 4) on exopolysaccharide biosynthesis in the early stages and mature *P. aeruginosa* biofilm formation, strain PAR 20. The abscissa represents the time (in hours) in order to differentiate early biofilm and mature biofilm, and the ordinate represents the percentage of the biofilm reduction.

The percentage of the reduction in biofilm formation by *P. aeruginosa* is showed after 8 hours, 24 hours, 48 hours and 72 hours of incubation.

Figure 4C:
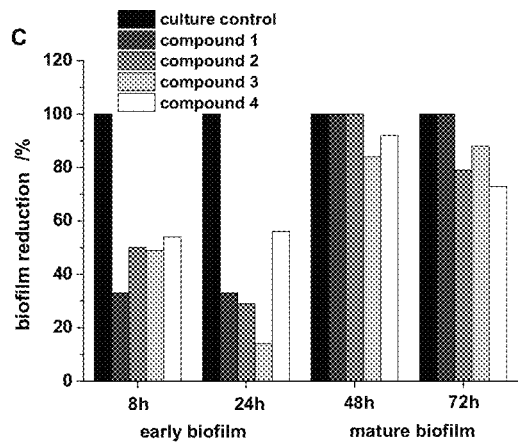

FIG. 4C represents the effect of the tested compounds (1, 2, 3 and 4) on exopolysaccharide biosynthesis in the early stages and mature *P. aeruginosa* biofilm formation, strain PAR 50. The abscissa represents the time (in hours) in order to differentiate early biofilm and mature biofilm, and the ordinate represents the percentage of the biofilm reduction.

The percentage of the reduction in biofilm formation by *P. aeruginosa* is showed after 8 hours, 24 hours, 48 hours and 72 hours of incubation.

EXAMPLES

Example 1: Preparation of α-1-C-hexyl-1,5-dideoxy-1,5-imino-D-xylitol (Compound 1) and β-1-C-(2,3-dihydroxypropyl)-1,5-dideoxy-1,5-imino-L-arabinitol (Compound 2)

Compounds 1 and 2 are two compounds of formulas I, with the following structure:

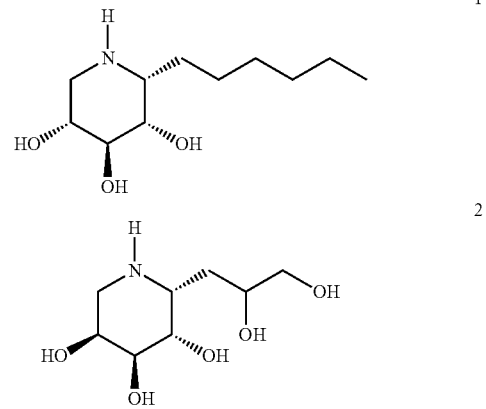

This synthesis of compounds 1 and 2 has been published under the following reference: Biela A, Oulaïdi F, Gallienne E, Górecki M, Frelek J, Martin O R. An improved methodology for the synthesis of 1-C-allyl imino-D-xylitol and -L-arabinitol and their rapid functionalization. *Tetrahedron* 69, 3348-3354 (2013). This document is incorporated herein by reference in its entirety.

Example 2: Preparation of β-1-C-propyl-1,4-dideoxy-1,4-imino-L-arabinitol (Compound 4)

Compound 4 is a compound of formula III, with the following structure:

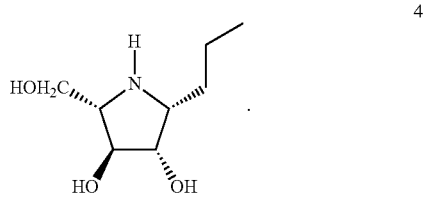

Compound 4 is obtained by hydrogenation of the precursor of compound 3: the compound 5, as showed below:

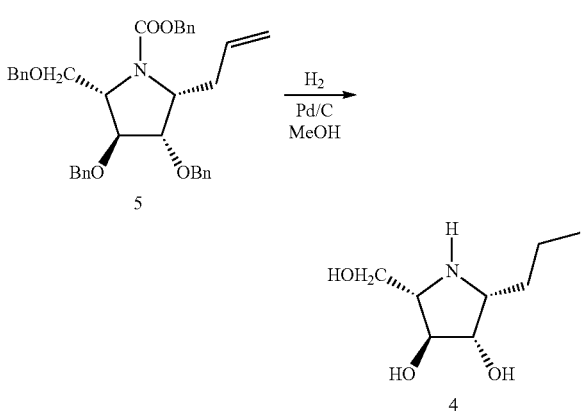

Compound 4 ((1R)-1-C-propyl-1,4-dideoxy-1,4-imino-L-arabinitol) can be obtained as follows:

To a solution of compound 5 (302 mg, 0.52 mmol) in iPrOH (5 mL) was added 1M HCl (2 mL) and 10% Pd on charcoal (78 mg).

The mixture was placed under an atmosphere of hydrogen and vigorously stirred for 18 h; the catalyst was then removed by filtration through a membrane, washed with iPrOH, and the solution was concentrated under reduced pressure.

The crude product was dissolved in water (5 mL), treated with Amberlite IRA-400 (OH⁻) ion exchange resin, the resin was filtered and the solvent evaporated to provide homogeneous 4 (79 mg, 86%).

Data for 4: $R_f$=0.12 (pet. ether:ethyl acetate 7:3); $[\alpha]_D$ −30.1 (c 0.92, MeOH). $^1$H NMR (400 MHz, CD$_3$OD): δ 3.84 (d, J=3.3 Hz, 1H, H3), 3.77 (d, J=3.6 Hz, 1H, H2), 3.67 (d, J=4.8 Hz, 2H, H5), 3.08 (dt, J=3.6 Hz, 6.8 Hz, 1H, H), 2.94-2.91 (m, 1H, H4), 1.62-1.39 (m, 4H, H6, H7), 0.97 (t, 1=7.2, 3H, H8). $^{13}$C NMR (100 MHz, CD$_3$OD): δ 81.53 (C3), 79.27 (C2), 68.68 (C4), 63.30 (C5), 62.65 (C1), 31.67 (C6), 21.36 (C7), 14.66 (C8). ESI-HRMS: calculated for $C_8H_{18}NO_3$ [M+H]⁺: 176.12812; found: 176.12819.

Compound 5 was obtained as described in the following reference: A. Chronowska, E. Gallienne, C. Nicolas, A. Kato, I. Adachi, O. R. Martin, An expeditious synthesis of an analogue of (−)-steviamine by way of the 1,3-dipolar cycloaddition of a nitrile oxide with a 1-C-allyl iminosugar" Tetrahedron Lett. 52, 2011, 6399-6402. This document is incorporated herein by reference in its entirety.

Example 3: Preparation of (1S,2S,3S,5S,9R)-1,2-dihydroxy-3-hydroxymethyl-5-p-methoxybenzylindolizidine (Compound 3)

Compound 3 is a compound of formula IV, with the following structure:

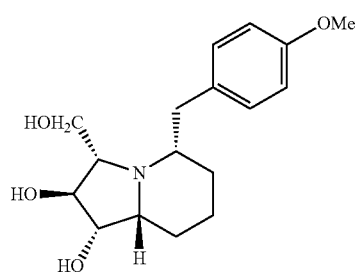

3

Compound 3 can be obtained by a catalytic hydrogenolysis under aqueous acidic conditions of the compound A.

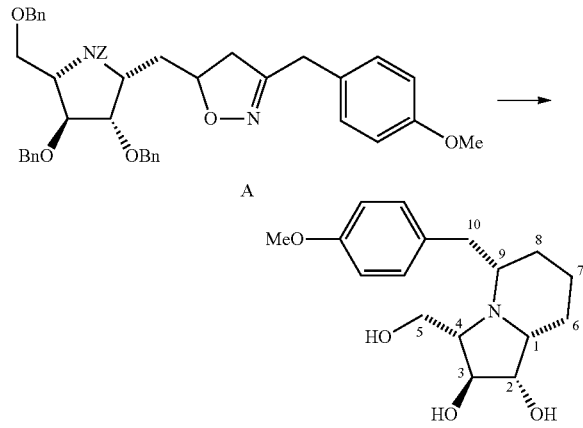

This synthesis has been described in the following reference: A. Chronowska, E. Gallienne, C. Nicolas, A. Kato, I. Adachi, O. R. Martin, An expeditious synthesis of an analogue of (−)-steviamine by way of the 1,3-dipolar cycloaddition of a nitrile oxide with a 1-C-allyl iminosugar" Tetrahedron Lett. 52, 2011, 6399-6402. This document is incorporated herein by reference in its entirety.

Example 4: Effects of the Iminosugars on Biofilm Formation and on the Number of Viable Bacteria Materials and Methods 1. Tested Compounds The above-mentioned compounds 1, 2, 3 and 4 have been used for the tests.

2. Bacterial Cultures

All tests were performed on Pseudomonas aeruginosa strains coded: PAR 5, PAR 20, PAR 50, isolated from suppurated wounds of three male patients with chronic diabetic foot infections.

The strains were propagated in 10 ml of Trypticase-Soy Broth (TSB, Difco) at 37° C. for 24 hours in aerobic conditions. Then the cultures were centrifuged (2000 rpm; 10 min) and washed with 10 ml of saline. Stock suspensions of the strains (1×10⁹ CFU/ml) were prepared by serial diluting of bacteria in saline using MacFarland's scale.

Drug resistance of the P. aeruginosa strains were tested using the disk diffusion method. Interpretation of the drug resistance of the Pseudomonas aeruginosa strains was done in accordance with the EUCAST standards (see the reference below for more information): http://www.eucast.org/fileadmin/src/media/PDFs/EUCAST_files/Breakpoint tables/Breakpoint_table_v_3.1.pdf.

To determine the drug resistance of the strains, the following antibiotics were used: amikacin, ciprofloxacin, gentamicin, piperacillin, tobramycin, ceftazidime (Oxoid, Basingstoke, UK). The results are provided in the Table 1 below. R means resistant to the antibiotic and S means sensitive to the antibiotic.

TABLE 1

Susceptibility of the tested P. aeruginosa strains: PAR 5, PAR 20, PAR 50 to selected antibiotics
Antibiotic susceptibility tests (according to EUCAST)

| Strain number | PAR 5 | PAR 20 | PAR 50 |
| --- | --- | --- | --- |
| Amikacin [30 µg] | S | S | R |
| Ciprofloxacin [5 µg] | S | S | S |
| Gentamicin [10 µg] | S | S | R |
| Piperacillin [100 µg] | S | S | R |
| Tobramycin [10 µg] | S | S | R |
| Ceftazidime [30 µg] | R | S | S |

3. Growth Conditions and Measurement of Biofilm Formation by P. aeruginosa

P. aeruginosa biofilm was set-up in sterile plastic 96-well plates with adherent surface (Greiner Bio-One, USA).

Twenty microliter quantities of the bacterial stock suspensions, prepared as described above, were added to each well followed with 180 µl of sterile TSB. Final concentration of the bacteria was 1×10⁸ CFU/ml.

The plates were centrifuged for 10 minutes at 2000 rpm to sediment bacteria on the bottom of each well and then incubated for 72 hours (37° C., aerobic conditions).

Biofilm quantity was determined using Congo red dye according to a modified procedure described by Allison et al. (Allison G C, Sutherland I W. A staining technique for bacteria and its correlation to extracellular carbohydrate production. *J Microbiol Meth* 2, 93-99 (1984)).

Briefly, at different time points (0, 6, 18, 24, 48 and 72 hours), the culture medium was gently removed from wells by using the pipette and immediately 200 µl of 0.1% Congo red solution was added. The plates were left for 30 minutes at room temperature and then 10 minutes before the end of staining, the plate was centrifuged for 10 minutes at 2000 rpm and then washed twice with buffered saline to remove unbound dye. Absorbance was measured at $\lambda$=492 nm wavelength using spectrophotometer (Awarness Technology Inc., Palm City, Fla., USA). All measurements were performed in triplicates and mean values±SD are given.

Figure 1:
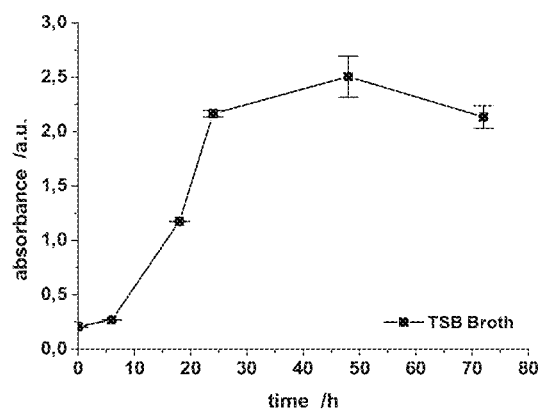
FIG. 1 represents the kinetic representation of biofilm formation by P. aeruginosa cultured in the trypticase soy broth (TSB). The abscissa represents the time (in hours), and the ordinate represents the value of absorbance (in au.).

Results are provided in FIG. 1. A high amount of biofilm was observed after 24 hours, followed by plateau and a typical breakdown of biofilm growth after 72 hours of the culture.

4. Biofilm Formation

The experiments on biofilm were performed in two different stages of the biofilm formation: early and late (mature).

Early biofilm model: formation of early biofilm under influence of the tested substances was observed by filling wells of a 96-well plate with 20 µl of *P. aeruginosa* suspension and 180 µl of TSB, as described above. Tested iminosugars (compounds 1, 2, 3 and 4) were added immediately after setting-up the bacteria at a final concentration of 0.9 mM. Then, the plate was gently mixed and incubated for 48 hours at 37° C.

Biofilm formation and the number of viable bacteria were checked in parallel in the following time intervals: 0, 0.5, 8, 24, 48 hours, in accordance with the procedure described above. Biofilm thickness was estimated by staining it with Cango Red and measuring optical density while number of viable bacteria was performed using the standard viable count method. (Allison G C, Sutherland I W. A staining technique for bacteria and its correlation to extracellular carbohydrate production. *J Microbiol Meth* 2, 93-99 (1984)).

*P. aeruginosa* suspension cultures in TSB broth alone were used as a control.

Mature biofilm model: the tested substances were added 48 hours after adherence of bacteria to the wells in a 96-well plate. The growth conditions of *P. aeruginosa* were exactly the same, as described above for the early biofilm model.

After the addition of iminosugars (compounds 1, 2, 3 and 4), the biofilm formation and the number of viable bacteria were checked in the following time intervals: 48, 48.5, 56, 72, 96 hours.

5. Number of Viable Bacteria

Numbers of viable bacteria contained in the early and mature biofilm were estimated on separate plates with wells filled with tested *P. aeruginosa* strains as described above (PAR 5, PAR 20, PAR 50).

At the same time intervals, biofilm content in each well was removed and mixed by multiple pippeting and transferred to sterile tubes. Then decimal dilutions of the bacterial suspension were made in TSB broth, plated on McConkey Agar (Oxoid), and incubated at 37° C. for 24 hours.

Numbers of colonies grown on platter were counted and total numbers of the viable bacteria calculated as colony forming units (CFU) per ml.

Results

1. Early Biofilm

Tests have been achieved on the three *P. aeruginosa* strains PAR 5, PAR 20, PAR 50, at an early stage of the biofilm formation (from 0 hours to 48 hours).

Results are as follows:

Results of PAR 5 are provided in FIG. 2A.

With the culture control, the absorbance is about 1.9 a.u. at 8 hours; about 2.1 a.u. at 24 hours and about 2.25 a.u. at 48 hours.

On the contrary, at 8 hours, 24 hours and 48 hours, the absorbance is always about 0.25 a.u. for compounds 1, 2, 3 and 4.

Thus, there is no significative difference between the compounds 1, 2, 3 and 4 on strain PAR 5.

Moreover, there is also no biofilm formation at 8 hours, 24 hours and 48 hours with compounds 1, 2, 3 and 4.

This proves that compounds 1, 2, 3 and 4 inhibit the formation of an early biofilm, in comparison with culture control. Thus, compounds 1, 2, 3 and 4 can prevent the biofilm formation.

Results of PAR 20 are provided in FIG. 2B.

With the culture control, the absorbance is about 1.4 a.u. at 8 hours; about 1.6 a.u. at 24 hours and about 1.6 a.u. at 48 hours.

On the contrary, with the compound 1, the absorbance is about 1.0 a.u. at 8 hours; about 1.0 a.u. at 24 hours and about 0.75 a.u. at 48 hours.

With the compound 2, the absorbance is about 0.75 a.u. at 8 hours; about 0.9 a.u. at 24 hours and about 0.9 a.u. at 48 hours.

With the compound 3, the absorbance is about 0.75 a.u. at 8 hours; about 0.7 a.u. at 24 hours and about 0.7 a.u. at 48 hours.

With the compound 4, the absorbance is about 0.6 a.u. at 8 hours; about 1.0 a.u. at 24 hours and about 0.75 a.u. at 48 hours.

This proves that compounds 1, 2, 3 and 4 inhibit the formation of an early biofilm, in comparison with culture control. Thus, compounds 1, 2, 3 and 4 can prevent the biofilm formation.

Results of PAR 50 are provided in FIG. 2C.

With the culture control, the absorbance is about 1.6 a.u. at 8 hours; about 2.6 a.u. at 24 hours and about 2.0 a.u. at 48 hours.

On the contrary, with the compound 1, the absorbance is about 0.5 a.u. at 8 hours; about 0.8 a.u. at 24 hours and about 0.9 a.u. at 48 hours.

With the compound 2, the absorbance is about 0.8 a.u. at 8 hours; about 0.7 a.u. at 24 hours and about 1.1 a.u. at 48 hours.

With the compound 3, the absorbance is about 0.8 a.u. at 8 hours; about 0.25 a.u. at 24 hours and about 0.25 a.u. at 48 hours.

With the compound 4, the absorbance is about 0.8 a.u. at 8 hours; about 1.4 a.u. at 24 hours and about 0.9 a.u. at 48 hours.

This proves that compounds 1, 2, 3 and 4 inhibit the formation of an early biofilm, in comparison with culture control. Thus, compounds 1, 2, 3 and 4 can prevent the biofilm formation.

2. Mature Biofilm

Tests have been achieved on the three *P. aeruginosa* strains PAR 5, PAR 20, PAR 50, at a mature stage of the biofilm formation (from 48 hours to 96 hours).

Results are as follows:

Results of PAR 5 are provided in FIG. 3A.

With the culture control, the absorbance is about 0.7 a.u. at 48 hours; about 1.75 a.u. at 56 hours, about 1.25 a.u. at 72 hours and about 0.5 a.u. at 96 hours.

With the compound 1, the absorbance is about 0.7 a.u. at 48 hours; about 1.1 a.u. at 56 hours, about 1.25 a.u. at 72 hours and about 0.5 a.u. at 96 hours.

With the compound 2, the absorbance is about 0.75 a.u. at 48 hours; about 1.0 a.u. at 56 hours, about 1.25 a.u. at 72 hours and about 1.5 a.u. at 96 hours.

With the compound 3, the absorbance is about 0.75 a.u. at 48 hours; about 1.25 a.u. at 56 hours, about 1.25 a.u. at 72 hours and about 1.25 a.u. at 96 hours.

With the compound 4, the absorbance is about 0.5 a.u. at 48 hours; about 1.25 a.u. at 56 hours, about 1.25 a.u. at 72 hours and about 0.5 a.u. at 96 hours.

This shows a weak influence of compounds 1, 2, 3 and 4 on mature biofilm formation.

Results of PAR 20 are provided in FIG. 3B.

With the culture control, the absorbance is about 0.6 a.u. at 48 hours; about 1.0 a.u. at 56 hours, about 1.1 a.u. at 72 hours and about 2.5 a.u. at 96 hours.

With the compound 1, the absorbance is about 0.75 a.u. at 48 hours; about 0.6 a.u. at 56 hours, about 1.5 a.u. at 72 hours and about 1.0 a.u. at 96 hours.

With the compound 2, the absorbance is about 0.6 a.u. at 48 hours; about 0.7 a.u. at 56 hours, about 1.1 a.u. at 72 hours and about 2.0 a.u. at 96 hours.

With the compound 3, the absorbance is about 0.6 a.u. at 48 hours; about 1.1 a.u. at 56 hours, about 0.75 a.u. at 72 hours and about 1.5 a.u. at 96 hours.

With the compound 4, the absorbance is about 0.5 a.u. at 48 hours; about 0.75 a.u. at 56 hours, about 1.25 a.u. at 72 hours and about 1.75 a.u. at 96 hours.

This shows a weak influence of compounds 1, 2, 3 and 4 on mature biofilm formation.

Results of PAR 50 are provided in FIG. 3C.

With the culture control, the absorbance is about 1.5 a.u. at 48 hours; about 1.5 a.u. at 56 hours, about 2.4 a.u. at 72 hours and about 3.2 a.u. at 96 hours.

With the compound 1, the absorbance is about 1.6 a.u. at 48 hours; about 1.5 a.u. at 56 hours, about 2.4 a.u. at 72 hours and about 1.9 a.u. at 96 hours.

With the compound 2, the absorbance is about 2.0 a.u. at 48 hours; about 1.75 a.u. at 56 hours, about 1.75 a.u. at 72 hours and about 2.0 a.u. at 96 hours.

With the compound 3, the absorbance is about 1.25 a.u. at 48 hours; about 1.0 a.u. at 56 hours, about 2.0 a.u. at 72 hours and about 2.5 a.u. at 96 hours.

With the compound 4, the absorbance is about 1.4 a.u. at 48 hours; about 1.4 a.u. at 56 hours, about 1.5 a.u. at 72 hours and about 1.75 a.u. at 96 hours.

This shows a weak influence of compounds 1, 2, 3 and 4 on mature biofilm formation.

3. Number of Viable Bacteria

The effect of the tested compounds (1, 2, 3 and 4) on the number of viable *P. aeruginosa* populations in early (A) and mature (B) biofilm has also been studied.

Early biofilm stage ends at 48 hours and mature biofilm stage starts at 48 hours. The measures for the mature biofilm began 8 hours after the beginning of this stage (at 56 hours).

The results depict logs of CFU/ml for three *P. aeruginosa* strains: PAR 5, PAR 20 and PAR 50 measured at different time intervals (0 hours, 8 hours, 24 hours, 48 hours, 56 hours, 72 hours and 96 hours). The detection limit is 100 CFU/ml.

The results are provided in Table 2 below.

TABLE 2

Effect of the tested compounds on the number of viable *P. aeruginosa* populations in early (A) and mature (B) biofilm

|  | Early biofilm | | | | Mature biofilm | | |
|---|---|---|---|---|---|---|---|
|  | 0 h | 8 h | 24 h | 48 h | 56 h | 72 h | 96 h |
|  | PAR 5 | | | | PAR 5 | | |
| Culture control | $2 \times 10^7$ | $3 \times 10^8$ | $2 \times 10^8$ | $3 \times 10^8$ | $3 \times 10^9$ | $5 \times 10^9$ | $3 \times 10^9$ |
|  | PAR 20 | | | | PAR 20 | | |
|  | $3 \times 10^6$ | $3 \times 10^8$ | $1 \times 10^9$ | $2 \times 10^9$ | $1 \times 10^8$ | $1 \times 10^8$ | $1 \times 10^9$ |
|  | PAR 50 | | | | PAR 50 | | |
|  | $5 \times 10^7$ | $2 \times 10^8$ | $2 \times 10^9$ | $3 \times 10^8$ | $7 \times 10^9$ | $9 \times 10^9$ | $2 \times 10^9$ |
|  | PAR 5 | | | | PAR 5 | | |
| Compound 1 | $2 \times 10^6$ | $3 \times 10^7$ | $9 \times 10^7$ | $1 \times 10^8$ | $3 \times 10^8$ | $2 \times 10^8$ | $3 \times 10^8$ |
|  | PAR 20 | | | | PAR 20 | | |
|  | $4 \times 10^6$ | $7 \times 10^7$ | $1 \times 10^8$ | $4 \times 10^8$ | $6 \times 10^7$ | $5 \times 10^7$ | $1 \times 10^8$ |
|  | PAR 50 | | | | PAR 50 | | |
|  | $8 \times 10^7$ | $2 \times 10^8$ | $4 \times 10^8$ | $3 \times 10^8$ | $2 \times 10^9$ | $1 \times 10^9$ | $1 \times 10^9$ |
|  | PAR 5 | | | | PAR 5 | | |
| Compound 2 | $8 \times 10^6$ | $2 \times 10^7$ | $1 \times 10^7$ | $1 \times 10^7$ | $4 \times 10^8$ | $2 \times 10^8$ | $5 \times 10^8$ |
|  | PAR 20 | | | | PAR 20 | | |
|  | $2 \times 10^6$ | $4 \times 10^7$ | $3 \times 10^8$ | $1 \times 10^9$ | $4 \times 10^8$ | $3 \times 10^7$ | $3 \times 10^8$ |
|  | PAR 50 | | | | PAR 50 | | |
|  | $3 \times 10^7$ | $2 \times 10^8$ | $7 \times 10^8$ | $1 \times 10^8$ | $6 \times 10^9$ | $1 \times 10^9$ | $9 \times 10^9$ |
|  | PAR 5 | | | | PAR 5 | | |
| Compound 3 | $6 \times 10^6$ | $4 \times 10^7$ | $1 \times 10^7$ | $2 \times 10^6$ | $3 \times 10^8$ | $2 \times 10^8$ | $1 \times 10^9$ |

TABLE 2-continued

Effect of the tested compounds on the number of viable *P. aeruginosa* populations in early (A) and mature (B) biofilm

| | Early biofilm | | | | Mature biofilm | | |
|---|---|---|---|---|---|---|---|
| | 0 h | 8 h | 24 h | 48 h | 56 h | 72 h | 96 h |
| | PAR 20 | | | | PAR 20 | | |
| | $5 \times 10^6$ | $3 \times 10^7$ | $5 \times 10^8$ | $3 \times 10^9$ | $3 \times 10^8$ | $7 \times 10^7$ | $7 \times 10^7$ |
| | PAR 50 | | | | PAR 50 | | |
| | $4 \times 10^7$ | $1 \times 10^8$ | $6 \times 10^8$ | $6 \times 10^8$ | $4 \times 10^8$ | $5 \times 10^9$ | $8 \times 10^9$ |
| | PAR 5 | | | | PAR 5 | | |
| Compound 4 | $9 \times 10^6$ | $3 \times 10^6$ | $9 \times 10^7$ | $3 \times 10^7$ | $4 \times 10^8$ | $3 \times 10^8$ | $2 \times 10^9$ |
| | PAR 20 | | | | PAR 20 | | |
| | $5 \times 10^6$ | $2 \times 10^7$ | $4 \times 10^8$ | $3 \times 10^9$ | $9 \times 10^8$ | $8 \times 10^7$ | $4 \times 10^8$ |
| | PAR 50 | | | | PAR 50 | | |
| | $1 \times 10^7$ | $2 \times 10^8$ | $7 \times 10^8$ | $1 \times 10^8$ | $3 \times 10^9$ | $9 \times 10^9$ | $1 \times 10^9$ |

There is no significant effect of the tested compounds on the viable bacterial number.

4. Reduction of Biofilm Growth

The effect of the tested compounds (1, 2, 3 and 4) on the reduction of biofilm growth has also been studied on the three *P. aeruginosa* strains PAR 5, PAR 20, PAR 50.

Results of PAR 5 are provided in FIG. 4A.

With the culture control, there is no modification of the biofilm growth at 8 hours, 24 hours, 48 hours and 72 hours.

With the compound 1, the reduction of biofilm growth is about 90% at 8 hours; about 90% at 24 hours; about 25% at 48 hours and about 10% at 72 hours.

With the compound 2, the reduction of biofilm growth is about 90% at 8 hours; about 90% at 24 hours; about 25% at 48 hours and about 10% at 72 hours.

With the compound 3, the reduction of biofilm growth is about 90% at 8 hours; about 90% at 24 hours; about 25% at 48 hours and about 10% at 72 hours.

With the compound 4, the reduction of biofilm growth is about 90% at 8 hours; about 90% at 24 hours; about 25% at 48 hours and about 10% at 72 hours.

This proves that the compounds 1, 2, 3 and 4 can reduce the biofilm growth, notably an early biofilm.

Results of PAR 20 are provided in FIG. 4B.

With the culture control, there is no modification of the biofilm growth at 8 hours, 24 hours, 48 hours and 72 hours.

With the compound 1, the reduction of biofilm growth is about 30% at 8 hours; about 40% at 24 hours; about 40% at 48 hours and about 0% at 72 hours.

With the compound 2, the reduction of biofilm growth is about 45% at 8 hours; about 45% at 24 hours; about 0% at 48 hours and about 0% at 72 hours.

With the compound 3, the reduction of biofilm growth is about 50% at 8 hours; about 60% at 24 hours; about 0% at 48 hours and about 20% at 72 hours.

With the compound 4, the reduction of biofilm growth is about 60% at 8 hours; about 35% at 24 hours; about 45% at 48 hours and about 0% at 72 hours.

This proves that the compounds 1, 2, 3 and 4 can reduce the biofilm growth, notably an early biofilm.

Results of PAR 50 are provided in FIG. 4C.

With the culture control, there is no modification of the biofilm growth at 8 hours, 24 hours, 48 hours and 72 hours.

With the compound 1, the reduction of biofilm growth is about 30% at 8 hours; about 30% at 24 hours; about 0% at 48 hours and about 0% at 72 hours.

With the compound 2, the reduction of biofilm growth is about 50% at 8 hours; about 70% at 24 hours; about 0% at 48 hours and about 20% at 72 hours.

With the compound 3, the reduction of biofilm growth is about 45% at 8 hours; about 45% at 24 hours; about 5% at 48 hours and about 20% at 72 hours.

With the compound 4, the reduction of biofilm growth is about 60% at 8 hours; about 35% at 24 hours; about 45% at 48 hours and about 30% at 72 hours.

This proves that the compounds 1, 2, 3 and 4 can reduce the biofilm growth, notably an early biofilm.

5. Conclusion

When iminosugars (compounds 1, 2, 3 and 4) were added at the early stage of biofilm formation, an inhibition of the biofilm development was observed. This result has been observed with all *P. aeruginosa* strains PAR 5, PAR 20 and PAR 50.

This effect was observed already in 8 hours after starting the experiments and persisted for the next 24 and 48 hours.

Thus, compounds 1, 2, 3 and 4 can prevent the biofilm formation.

However, weak influence on biofilm formation was observed when the imminosugars were added to the already formed, mature biofilm of *P. aeruginosa* strains.

Besides, no significant effect on the viable bacterial number was observed, when the biofilm is early and when the biofilm is mature.

In early biofilm model, average reduction of biofilm formation compared to control culture (expressed in %), for strains PAR 5, PAR 20 and PAR 50 were: 89%, 43.5% and 60%, respectively, while in mature biofilm model reduction rate was much lower and was for PAR 5—7.7%, PAR 20—12.8% and for PAR 50—12.5%. (Percent decrease in biofilm thickness was obtained as a mean value from 3 consecutive measurements of the Congo Red stained biofilm using spectrophotometer after addition of the tested iminosugars in comparison to control regarded as 100%).

Thus, compounds 1, 2, 3 and 4 can inhibit the growth of the biofilm, notably the growth of an early biofilm.

The invention claimed is:

1. A method of treatment and/or of prevention of biofilm formation, comprising the administration of at least one compound of the following formula I:

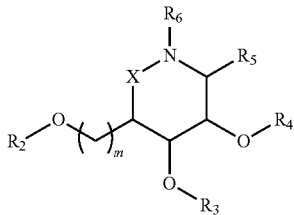

wherein:
m represents an integer being equal to 0, 1, 2, 3, 4, 5 or 6,
X represents a simple bond,
$R_2$, $R_3$ and $R_4$ represent independently from each other:
  a hydrogen atom, or
  a linear or branched ($C_1$-$C_{12}$)-alkyl, or
  a linear or branched ($C_1$-$C_{12}$)-acyl,
$R_5$ represents:
  a hydrogen atom, or
  a linear or branched ($C_1$-$C_{13}$)-alkyl, or
$R_6$ represents:
  a hydrogen atom, or
  a linear or branched optionally substituted ($C_1$-$C_{12}$)-alkyl, or
  a linear or branched optionally substituted ($C_1$-$C_{12}$)-acyl, or
  a linear or branched, optionally substituted ($C_1$-$C_{12}$)-alkyl interrupted by up to 3 heteroatoms selected from O, S or N, or
  a linear or branched, optionally substituted ($C_1$-$C_{12}$)-acyl interrupted by up to 3 heteroatoms selected from O, S or N, or $R_5$ and $R_6$ represent together with the N atom to which $R_6$ is bound and the carbon atom to which $R_5$ is bound an alkylene radical Z having 2 to 5 carbon atoms which is optionally substituted and/or optionally interrupted by up to 3 heteroatoms selected from O, S, N and/or terminated by an heteroatom selected from O, S, N,
and the pharmaceutically acceptable salts, enantiomers, diastereoisomers of same, as well as mixture of same.

2. The method of treatment and/or of prevention of biofilm formation according to claim 1, wherein the said compound corresponds to a compound of the following formula I:

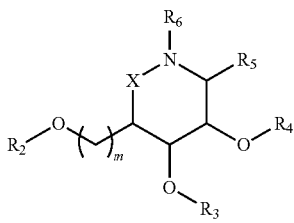

wherein:
m represents an integer being equal to 0, 1, 2, 3, 4, 5 or 6,
X represents a simple bond,
$R_2$, $R_3$ and $R_4$ represent independently from each other:
  a hydrogen atom, or
  a linear or branched ($C_1$-$C_{12}$)-alkyl, or
  a linear or branched ($C_1$-$C_{12}$)-acyl,
$R_5$ represents:
  a hydrogen atom, or
  a linear or branched ($C_1$-$C_{13}$)-alkyl,
$R_6$ represents:
  a hydrogen atom, or
  a linear or branched ($C_1$-$C_{12}$)-alkyl, optionally substituted by up to 3 radicals selected from:
    —OH,
    —O-linear ($C_1$-$C_{12}$)-alkyl,—a halogen atom chosen among Br, Cl, I, F,
    optionally salified or esterified carboxy,
    an oxo group,
    an aromatic or heteroaromatic aryl optionally substituted by:
      —OH,
      —O-linear ($C_1$-$C_{12}$)-alkyl,
      a halogen atom chosen among Br, Cl, I, F,
      optionally salified or esterified carboxy,
      optionally salified or esterified carboxy ($C_1$-$C_{12}$)-alkyl, or
  a linear or branched ($C_1$-$C_{12}$)-acyl, optionally substituted by up to 3 radicals selected from:
    —OH,
    —O-linear ($C_1$-$C_{12}$)-alkyl,
    a halogen atom chosen among Br, Cl, I, F,
    optionally salified or esterified carboxy,
    an oxo group,
    an aromatic or heteroaromatic aryl optionally substituted by:
      —OH,
      —O-linear ($C_1$-$C_{12}$)-alkyl,
      a halogen atom chosen among Br, Cl, I, F, optionally salified or esterified carboxy,
      optionally salified or esterified carboxy ($C_1$-$C_{12}$)-alkyl,
and $R_6$ can be optionally interrupted by up to 3 heteroatoms selected from O, S or N,
or $R_5$ and $R_6$ represent together with the N atom to which $R_6$ is bound and the carbon atom to which $R_5$ is bound an alkylene radical Z having 2 to 5 carbon atoms which is optionally interrupted by 1 or 2 heteroatoms selected from O, S, N and/or terminated by an heteroatom selected from O, S, N and/or optionally substituted by up to three radicals selected from:
  —OH,
  —O-linear ($C_1$-$C_{12}$)-alkyl,
  a halogen atom chosen among Br, Cl, I, F,
  optionally salified or esterified carboxy,
  an oxo group,
  an aromatic or heteroaromatic aryl optionally substituted by:
    —OH,
    —O-linear ($C_1$-$C_{12}$)-alkyl,
    a halogen atom chosen among Br, Cl, I, F,
    optionally salified or esterified carboxy,
    optionally salified or esterified carboxy ($C_1$-$C_{12}$)-alkyl,
and the pharmaceutically acceptable salts, enantiomers, diastereoisomers of same, as well as mixtures of same.

3. The method of treatment and/or of prevention of biofilm formation according to claim 1, wherein the said compound corresponds to a compound of the following formula I:

119

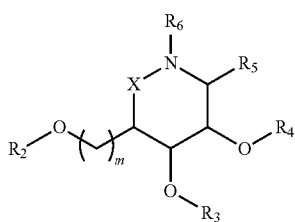

wherein:
m represents an integer being equal to 0, 1, 2,
X represents a simple bond,
$R_2$, $R_3$ and $R_4$ represent independently from each other:
  a hydrogen atom, or
  a linear or branched ($C_1$-$C_{12}$)-alkyl, or
  a linear or branched ($C_1$-$C_{12}$)-acyl,
$R_5$ represents:
  a hydrogen atom, or
  a linear or branched ($C_1$-$C_{13}$)-alkyl,
$R_6$ represents:
  a hydrogen atom, or
  a linear or branched ($C_1$-$C_{12}$)-alkyl, optionally substituted by up to 3 radicals selected from:
    —OH,
    —O-linear ($C_1$-$C_{12}$)-alkyl,—a halogen atom F,
    optionally salified or esterified carboxy,
    an oxo group,
    an aromatic or heteroaromatic aryl optionally substituted by:
      —OH,
      —O-linear ($C_1$-$C_{12}$)-alkyl,
      a halogen atom F,
      optionally salified or esterified carboxy, or
  a linear or branched ($C_1$-$C_{12}$)-acyl, optionally substituted by up to 3 radicals selected from:
    —OH,
    —O-linear ($C_1$-$C_{12}$)-alkyl,—a halogen atom F,
    optionally salified or esterified carboxy,
    an oxo group,
    an aromatic or heteroaromatic aryl optionally substituted by:
      —OH,
      —O-linear ($C_1$-$C_{12}$)-alkyl,
      a halogen atom F,
      optionally salified or esterified carboxy, or $R_5$ and $R_6$ represent together with the N atom to which $R_6$ is bound and the carbon atom to which $R_5$ is bound an alkylene radical Z having 2 to 5 carbon atoms which is optionally interrupted by 1 or 2 heteroatoms selected from 0 and N and/or terminated by an heteroatom selected from 0 and N and/or optionally substituted by up to three radicals selected from:
      —OH,
      —O-linear ($C_1$-$C_{12}$)-alkyl,
      a halogen atom F,
      optionally salified or esterified carboxy,
      an oxo group,
      an aromatic or heteroaromatic aryl optionally substituted by:
        —OH,
        —O-linear ($C_1$-$C_{12}$)-alkyl,
        a halogen atom F,
        optionally salified or esterified carboxy,

120 and the pharmaceutically acceptable salts, enantiomers, diastereoisomers of same, as well as mixtures of same.

4. The method of treatment and/or of prevention of biofilm formation according to claim 1, wherein the said compound corresponds to a compound of the following formula II:

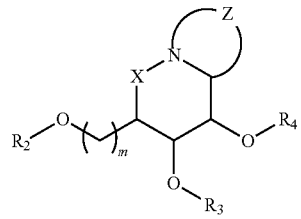

wherein:
m represents an integer being equal to 0, 1, 2, 3, 4, 5 or 6,
X represents a simple bond,
$R_2$, $R_3$ and $R_4$ represent independently from each other:
  a hydrogen atom, or
  a linear or branched ($C_1$-$C_{12}$)-alkyl, or
  a linear or branched ($C_1$-$C_{12}$)-acyl,
Z represents an alkylene radical having 2 to 5 carbon atoms which is optionally substituted and/or optionally interrupted by up to 3 heteroatoms selected from O, S, N and/or terminated by an heteroatom selected from O, S, N,
and the pharmaceutically acceptable salts, enantiomers, diastereoisomers of same, as well as mixtures of same.

5. The method of treatment and/or of prevention of biofilm formation according to claim 1, wherein the said compound corresponds to a compound of the following formula XII:

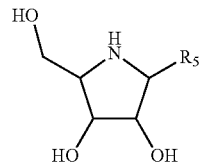

wherein R5 represents:
  a linear or branched ($C_1$-$C_{13}$)-alkyl, and the pharmaceutically acceptable salts, enantiomers, diastereoisomers of same, as well as mixtures of same.

6. The method of treatment and/or of prevention of biofilm formation according to claim 1, wherein the said compound corresponds to a compound of the following formula II:

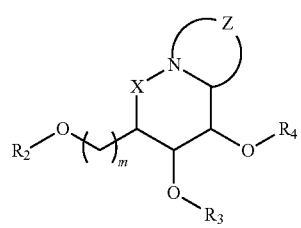

wherein:
  m represents 1,
  X represents a simple bond,
  $R_2$, $R_3$ and $R_4$ represent a hydrogen atom,
  $R_5$ and $R_6$ represent together with the N atom to which $R_6$ is bound and the carbon atom to which $R_5$ is bound an alkylene radical Z having 2 to 5 carbon atoms which is optionally interrupted by 1 or 2 heteroatoms selected from O, S, N, and/or terminated by an heteroatom selected from O, S, N and/or optionally substituted by up to three radicals selected from:
  optionally salified or esterified carboxy,
  an oxo group,
    an aromatic or heteroaromatic aryl possibly substituted by:
  O-linear ($C_1$-$C_{12}$)-alkyl,
and the pharmaceutically acceptable salts, enantiomers, diastereoisomers of same, as well as mixtures of same.

7. The method of treatment and/or of prevention of biofilm formation according to claim 1, wherein the said compound corresponds to a compound having the following formula:

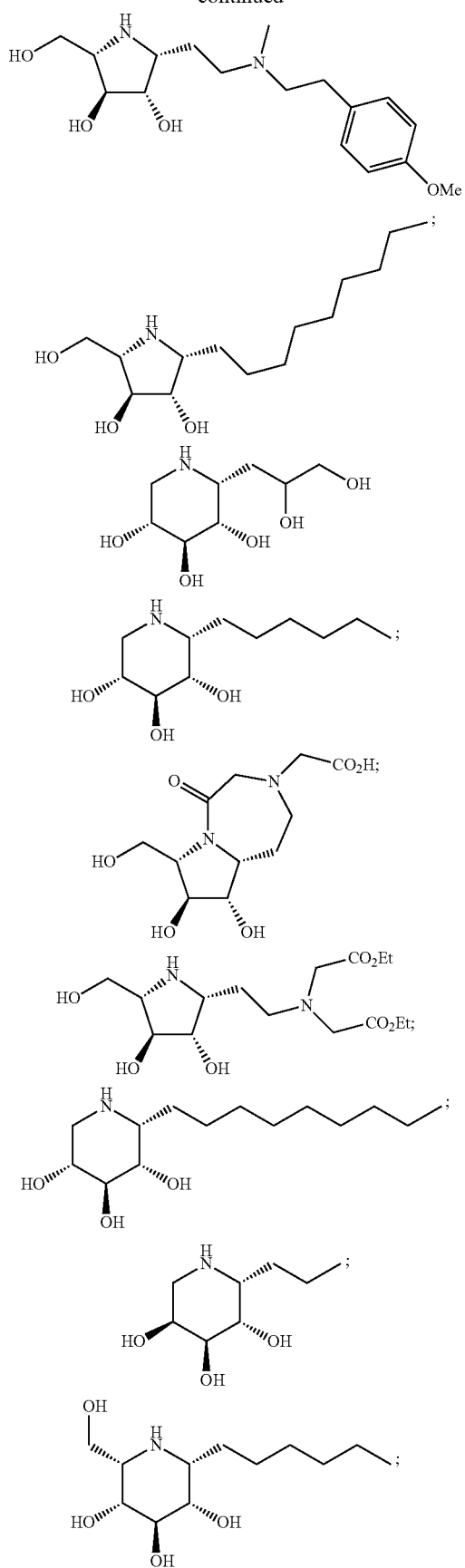

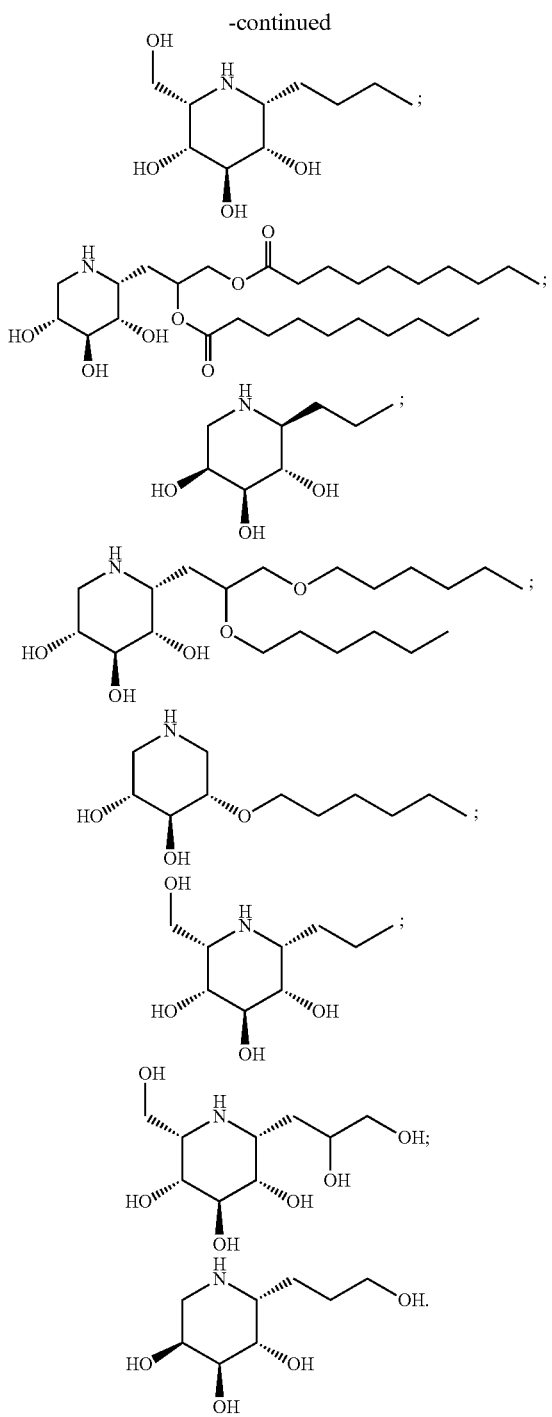

8. Compounds of the following formula III:

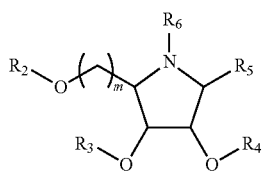

wherein:
m represents an integer being equal to 1,
$R_2$, $R_3$ and $R_4$ represent independently from each other:
  a hydrogen atom, or
  a linear or branched ($C_1$-$C_{12}$)-alkyl, or
  a linear or branched ($C_1$-$C_{12}$)-acyl,
$R_5$ represents:
  a linear or branched ($C_1$-$C_{13}$)-alkyl, optionally substituted by up to 3 radicals selected from:
    —O-linear ($C_1$-$C_{12}$)-alkyl, optionally substituted by an oxo group,
    optionally salified or esterified carboxy,
    an oxo group,
    an aromatic or heteroaromatic aryl optionally substituted by:
      —O-linear ($C_1$-$C_{12}$)-alkyl,
and $R_5$ can be optionally interrupted by up to 3 heteroatoms selected from 0 or N,
with the proviso that $R_5$ cannot be a linear $C_4$-alkyl if $R_2$, $R_3$ and $R_4$ are hydrogen atom,
$R_6$ represents a hydrogen atom,
or $R_5$ and $R_6$ represent together with the N atom to which $R_6$ is bound and the carbon atom to which $R_5$ is bound an alkylene radical Z having 2 to 5 carbon atoms which is optionally interrupted by 1 or 2 heteroatoms selected from O, S, N and/or terminated by an heteroatom selected from O, S, N and substituted by up to three radicals selected from:
  optionally salified or esterified carboxy,
  an oxo group,
  an aromatic or heteroaromatic aryl optionally substituted by:
    —O-linear ($C_1$-$C_{12}$)-alkyl,
and the pharmaceutically acceptable salts, enantiomers, diastereoisomers of same, as well as mixtures of same, with the proviso that the following compounds is excluded:

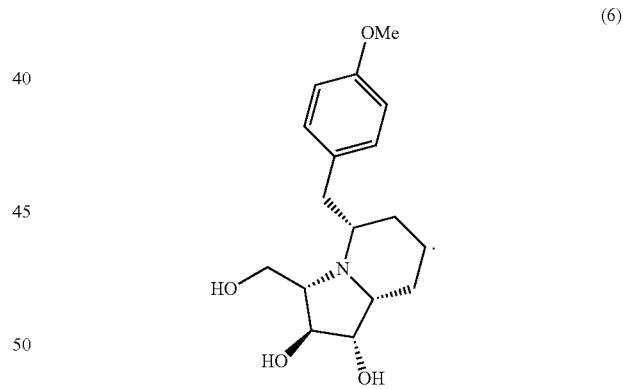

(6)

9. Compounds according to claim 8, the said compounds having the following formula:

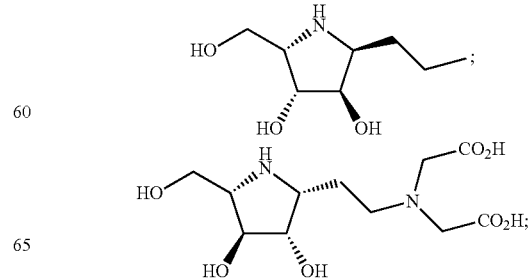

-continued

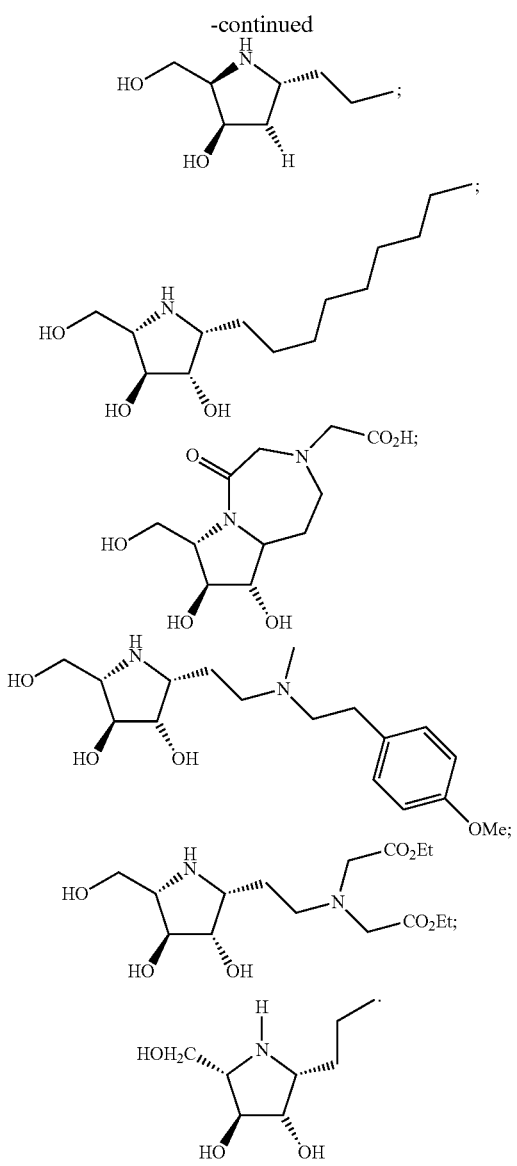

10. Composition comprising as active ingredient one or more of the compounds of the following formula I:

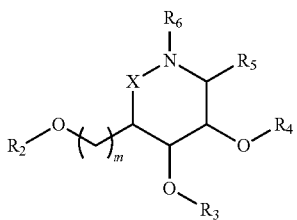

wherein:
  m represents an integer being equal to 0, 1, 2, 3, 4, 5 or 6,
  X represents a simple bond,
  $R_2$, $R_3$ and $R_4$ represent independently from each other:
    a hydrogen atom, or
    a linear or branched ($C_1$-$C_{12}$)-alkyl, or
    a linear or branched ($C_1$-$C_{12}$)-acyl,
  $R_5$ represents:
    a hydrogen atom, or
    a linear or branched ($C_1$-$C_{13}$)-alkyl, or
    a linear or branched, optionally substituted ($C_1$-$C_{13}$)-alkyl interrupted by up to 3 heteroatoms selected from O, S or N,
  $R_6$ represents:
    a hydrogen atom, or
    a linear or branched optionally substituted ($C_1$-$C_{12}$)-alkyl, or
    a linear or branched optionally substituted ($C_1$-$C_{12}$)-acyl, or
    a linear or branched, optionally substituted ($C_1$-$C_{12}$)-alkyl interrupted by up to 3 heteroatoms selected from O, S or N, or
    a linear or branched, optionally substituted ($C_1$-$C_{12}$)-acyl interrupted by up to 3 heteroatoms selected from O, S or N,
  or $R_5$ and $R_6$ represent together with the N atom to which $R_6$ is bound and the carbon atom to which $R_5$ is bound an alkylene radical Z having 2 to 5 carbon atoms which is optionally substituted and/or optionally interrupted by up to 3 heteroatoms selected from O, S, N and/or terminated by an heteroatom selected from O, S, N,
and the pharmaceutically acceptable salts, enantiomers, diastereoisomers of same, as well as mixtures of same, and further comprising at least one antibiotic.

11. Composition comprising as active ingredient one or more of the compounds of the following formula I:

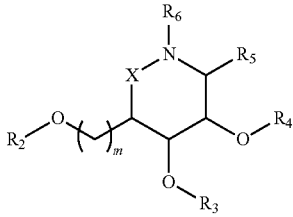

wherein:
  m represents an integer being equal to 0, 1, 2, 3, 4, 5 or 6,
  X represents a simple bond,
  $R_2$, $R_3$ and $R_4$ represent independently from each other:
    a hydrogen atom, or
    a linear or branched ($C_1$-$C_{12}$)-alkyl, or
    a linear or branched ($C_1$-$C_{12}$)-acyl,
  $R_5$ represents:
    a hydrogen atom, or
    a linear or branched ($C_1$-$C_{13}$)-alkyl, or
  $R_6$ represents:
    a hydrogen atom, or
    a linear or branched optionally substituted ($C_1$-$C_{12}$)-alkyl, or
    a linear or branched optionally substituted ($C_1$-$C_{12}$)-acyl, or
    a linear or branched, optionally substituted ($C_1$-$C_{12}$)-alkyl interrupted by up to 3 heteroatoms selected from O, S or N, or
    a linear or branched, optionally substituted ($C_1$-$C_{12}$)-acyl interrupted by up to 3 heteroatoms selected from O, S or N, or $R_5$ and $R_6$ represent together with the N atom to which $R_6$ is bound and the carbon atom to which $R_5$ is bound an alkylene radical Z having 2 to 5 carbon atoms which is optionally substituted and/ or optionally interrupted by up to 3 heteroatoms selected from O, S, N and/or terminated by an heteroatom selected from O, S, N, and the pharmaceutically acceptable salts, enantiomers, diastereoisomers of same, as well as mixtures of same, and further comprising at least one disinfecting agent.

12. A method of treatment and/or of prevention of infection(s) caused by biofilm-forming bacteria, comprising the administration of at least one composition according to claim 10.

13. A method of treatment and/or of prevention of biofilm formation, comprising the administration of at least one composition according to claim 10.

14. A method of treatment and/or of prevention of biofilm formation, comprising the administration of at least one composition according to claim 11.

15. A method for disinfecting comprising the use of a composition comprising as active ingredient one or more of the compounds according to claim 11.

16. The composition according to claim 10, wherein said at least one antibiotic is selected from the group consisting of aminoglycosides, quinolones, cephalosporins, ureidopenicillines, carbapenems, polymyxins and monobactams.

17. The composition according to claim 10, wherein said at least one antibiotic is selected from the group consisting of Amikacin, Ciprofloxacin, Gentamicin, Piperacilin, Tobramycin, and Ceftazidime.

18. The composition according to claim 11, wherein said at least one disinfecting agent is selected from the group consisting of antioxidants, phosphates, colouring agents, EDTA, and combinations thereof.

* * * * *